United States Patent
Posner et al.

(10) Patent No.: US 6,586,464 B2
(45) Date of Patent: Jul. 1, 2003

(54) ARTEMISININ ANALOGS HAVING ANTIMALARIAL, ANTIPROLIFERATIVE, AND ANTITUMOR ACTIVITIES AND CHEMOSELECTIVE METHODS OF MAKING THE SAME

(75) Inventors: Gary H. Posner, Baltimore, MD (US); Hardwin O'Dowd, Somerville, MA (US); Suji Xie, Baltimore; Theresa A. Shapiro, Towson, both of MD (US); Christopher Murray, Longmont, CO (US)

(73) Assignees: Johns Hopkins University, Baltimore, MD (US); Hauser, Inc.; a part interest ( * ) Notice: Subject to any disclaimer, the term of this patent is extended or adjusted under 35 U.S.C. 154(b) by 0 days.

(21) Appl. No.: 09/887,922

(22) Filed: Jun. 22, 2001

(65) Prior Publication Data

US 2002/0055528 A1 May 9, 2002

Related U.S. Application Data

(62) Division of application No. 09/228,668, filed on Jan. 12, 1999.

(51) Int. Cl.[7] .................... C07D 519/00; A61K 31/357
(52) U.S. Cl. .................. 514/450; 514/365; 514/367; 548/203; 548/179; 549/348
(58) Field of Search ................. 548/179, 203; 549/348; 514/365, 367, 450

(56) References Cited

U.S. PATENT DOCUMENTS

| 5,225,437 A | 7/1993 | Posner et al. ............... 514/450 |
| 5,225,562 A | 7/1993 | McChesney et al. ........ 549/348 |
| 5,677,468 A | 10/1997 | Zheng et al. ............... 549/348 |

FOREIGN PATENT DOCUMENTS

| WO | WO 93/08195 | 4/1993 | ............... 549/348 |

OTHER PUBLICATIONS

"Conversion of Glycosyl Fluorides into C–Glycosides Using Organoaluminum Reagents. Sterospecific Alkylation at C–6 of a Pyranose Sugar," Gary H. Posner, et al., *Tetrahedron Letters*, vol. 26, No. 15 (1985), pp. 1823–1826.

"A Convenient, One–Step, High Yield Replacement of an Anomeric Hydroxyl Group by a Fluorine Atom Using DAST. Preparation of Glycosyl Fluorides," Gary H. Posner, et. al. *Tetrahedron Letters*, vol. 26, No. 1 (1985), pp. 5–8.

"Synthesis and Antimalarial Activity of Heteroatom–Containing Bicyclic Endoperoxides," Gary H. Posner, et al., *Tetrahedron*, vol. 53, No. 1 (1997), pp. 37–50.

"Synthesis and Antimalarial Activities of 12β–Allyldexoartemisinin and Its Derivatives," Yu Ming Pu, et. al. *J. Med. Chem.*, vol. 38 (1995), pp. 613–616.

"Synthesis and Cytotoxicity of Novel Artemisinin Analogs," Mankil Jung, *Bioorganic and Medicinal Chemistry Letters*, vol. 7, No. 8 (1997), pp. 1091–1094.

Trioxane Dimers Have Potent Antimalarial, Antiproliferative and Antitumor Activities in Vitro, Gary H. Posner, et. al. *Bioorganic & Medicinal Chemistry*, vol. 5, No. 7, (1997), pp. 1257–1265.

"A Concise and Steroselective Synthesis of (+)-12-n-Butyldeoxoartemisinin," Mankil Jung. et. al., *Synlett*, (1990), pp. 743–744.

Phosphonate Analogs of Carbocyclic Nucleotides, 'Robert D. Elliott, et. al., *J. Med. Chem.*, vol. 37, (1994), pp. 739–744.

"Carbocyclic Arabinofuranosyladenine (Cyclaradine): Efficacy Against Genital Herpes in Guinea Pigs," Robert Vince, et. al., *Science*, vol. 221 (1983), pp. 1405–1406.

"An Unusual Acid–Catalyzed Rearrangement of 1,2,4–Trioxanes," Yu–Ming Pu et. al., *Heterocycles*, vol. 36, No. 9, (1993), pp. 2099–2107.

"Efficient Preparation of Novel Qinghaosu (Artemisinin) Derivatives: Conversation of Qinghaosu (Artemisinin) Acid into Deoxoqinghaosu Derivatives and 5–Carba–4–deoxoartesunic Acid," Richard K. Haynes, et. al., *Synlett*, (1992), pp. 481–483.

"Artemisinin and the Antimalarial Endoperoxides: from Herbal Remedy to Targeted Chemotherapy," S.R. Meshnick, et. al., *Microbiological Reviews*, vol. 60, No. 2, (1996), pp. 301–315.

(List continued on next page.)

Primary Examiner—Robert Gerstl
(74) Attorney, Agent, or Firm—Steven C. Petersen; Sarah S. O'Rourke; Hogan & Hartson LLP

(57) ABSTRACT

Methods for producing novel artemisinin analogs and artemisinin dimers having antimalarial, antiproliferative and antitumor activities are described herein. These novel artemisinin analogs and artemisinin dimers have the following structure

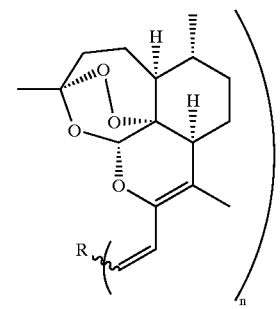

or diastereomers thereof, having antimalarial, and antiproliferative and antitumor activities wherein, the monomers of the present invention are formed when n is I and R is alkyl, cycloalkyl, heteroalkyl, heterocycloalkyl, alkenyl, alkynyl, aryl or heteroaryl. The dimers of the present invention are formed when n is 2 and R is a linker including, but not limited to, alkyl, cycloalkyl, heteroalkyl, heterocycloalkyl, alkenyl, alkynyl, aryl or heteroaryl.

16 Claims, 23 Drawing Sheets

OTHER PUBLICATIONS

"Some Aspects of the Chemistry and Biological Activity of Artemisinin and Related Antimalarials," Syed S. Zaman, et. al., *Heterocycles*, vol. 32, No. 8, (1991), pp. 1593–1638.

Artemisinin, Transactions of the Royal Society of Tropical Medicine and Hygiene, vol. 88:1, (Jun. 1994), pp. S1/1–S1/65.

"Extraordinarily Potent Antimalarial Compounds: New, Structurally, Simple, Easily Synthesized, Tricyclic, 1,2,4–Trioxanes," Gary H. Posner, et. al., *J. Med. Chem.*, vol. 35, No. 13, (1992), pp. 2459–2467.

"Artemisinin (Qinghaosu): A New Type of Antimalarial Drug," Anthony r. Butler, et. al., (1992), pp. 85–90.

"Cytotoxicity of Artemisinin–Related Endoperoxides to Ehrlich Ascites Tumor Cells," Herman J. Woerdenbag, et. al., *Journey of Natural Products*, vol. 56, No. 6, (1993), pp. 849–856.

"Qinghaosu (Artemisinin): An Antimalarial Drug from China," Daniel L. Klayman.

"Synthesis of a Novel Ring Contracted Artemisinin Derivative," B. Venugopalan, et. al., *Bioorganic & Medicinal Chemistry Letters*, vol. 4, No. 5 (1994), pp. 751–752.

"A Concise Synthesis of Novel Aromatic Analogs of Artemisinin," Jung, et. al., *Heterocycles*, vol. 45, No. 6, pp. 1055–1058 (Jun. 1997).

Ie  VII

VII-a, R=H; m=1, n=1 77%

VII-b, R=Me; m=1, n=1 83%

VII-c, R=Ph, m=1, n=1 76%

VII-d, R=p-NO$_2$Ph; m=1, n=1 69%

VII-e, R=p-ClPh, m=1, n=1 58%

VII-f, R=m-Ph [E,E]; m=2, n=2

VII-g, R=m-Ph [E,Z]; m=2, n=2

VII-h, R=m-Ph [Z,Z]; m=2, n=2

VII-i, R=p-Ph([E,E], [E,Z], [Z,Z]); m=2, n=2

ARTEMISININ ANALOGS HAVING ANTIMALARIAL, ANTIPROLIFERATIVE, AND ANTITUMOR ACTIVITIES AND CHEMOSELECTIVE METHODS OF MAKING THE SAME

RELATED APPLICATIONS

This is a divisional application of U.S. patent application Ser. No. 09/228,668, filed Jan. 12, 1999, which is incorporated herein by reference.

CONTRACTUAL ORIGIN OF THE INVENTION

This study was supported in-part by National Institutes of Health grant AI 34885 (to G.H.P.) and NCRR OPTD-GCRC RR00722 (to T.A.S.) and joint inventors G.H.P., H.O.D., S.X. and T.A.S., have assigned their rights to the Johns Hopkins University.

BACKGROUND OF THE INVENTION

1. Field of the Invention

The present invention relates to a procedure for the production of enantiomerically pure monomeric and dimeric C-10 non-acetal derivatives of natural trioxane artemisinin having high in vitro antimalarial, antiproliferative and antitumor activities. The present invention further relates to the formation of a novel trioxane aldehyde compound produced via a chemoselective C—C bond formation at the C-10 position upon reaction of artemisinin trioxane lactone with lithiothiazole or lithiobenzothiazole. This trioxane aldehyde may then be reacted with organolithium, Grignard, and phosphorus ylide nucleophiles exclusively via carbonyl addition.

2. Description of the State of Art

Each year approximately 200–300 million people experience a malarial illness and over 1 million individuals die. In patients with severe and complicated disease, the mortality rate is between 20 and 50%.

Plasmodium is the genus of protozoan parasites which is responsible for all cases of malaria and *Plasmodium falciparum* is the species of parasite that is responsible for the vast majority of fatal malaria infections. Malaria has traditionally been treated with quinolines such as chloroquine, quinine, mefloquine, and primaquine and with antifolates such as sulfadoxine-pyrimethamine. Unfortunately, most *P. falciparum* strains have now become resistant to chloroquine, and some, such as those in Southeast Asia, have also developed resistance to mefloquine and halofantrine; multidrug resistance is developing in Africa also.

The endoperoxides are a promising class of antimalarial drugs which may meet the dual challenges posed by drug-resistant parasites and the rapid progression of malarial illness. The first generation endoperoxides include artemisinin and several synthetic derivatives, discussed in further detail below.

*Artemisia annua* L., also known as qinghao or sweet wormwood, is a pervasive weed that has been used for many centuries in Chinese traditional medicine as a treatment for fever and malaria. Its earliest mention, for use in hemorrhoids, occurs in the *Recipes for 52 Kinds of Diseases* found in the Mawangdui Han dynasty tomb dating from 168 B.C. Nearly five hundred years later Ge Hong wrote the *Zhou Hou Bei Ji Fang* (Handbook of Prescriptions for Emergency Treatments) in which he advised that a water extract of qinghao was effective at reducing fevers. In 1596, Li Shizhen, the famous herbalist, wrote that chills and fever of malaria can be combated by qinghao preparations. Finally, in 1972, Chinese chemists isolated from the leafy portions of the plant the substance responsible for its reputed medicinal action. This crystalline compound, called qinghaosu, also referred to as QHS or artemisinin, is a sesquiterpene lactone with an internal peroxide linkage.

Artemisinin is a member of the amorphane subgroup of cadinenes and has the following structure (I).

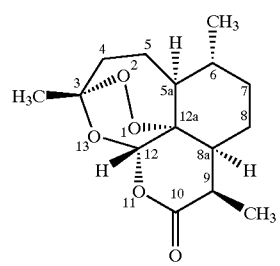

Artemisinin or QHS was the subject of a 1979 study conducted by the Qinghaosu Antimalarial Coordinating Research Group involving the treatment of 2099 cases of malaria (*P. vivax* and *P. falciparum* in a ratio of about 3:1) with different dosage forms of QHS, leading to the clinical cure of all patients. See, Qinghaosu Antimalarial Coordinating Research Group, *Chin. Med. J.*, 92:811 (1979). Since that time artemisinin has been used successfully in many thousand malaria patients throughout the world including those infected with both chloroquine-sensitive and chloroquine-resistant strains of *P. falciparum*. Assay of artemisinin against *P. falciparum* in vitro revealed that its potency is comparable to that of chloroquine in two Hanian strains (Z. Ye, et al., *J. Trad. Chin. Med.*, 3:95 (1983)) and of mefloquine in the Camp (chloroquine-susceptible) and Smith (chloroquine-resistant) strains, D. L. Klayman, et al., *J. Nat. Prod.*, 47:715 (1984).

Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage which is believed to be an essential moiety for antimalarial activity.

Reduction of artemisinin in the presence of sodium borohydride results in the production of dihydroartemisinin (II-1) or DHQHS, (illustrated in structure II below), in which the lactone group is converted to a lactol (hemiacetal) function, with properties similar to artemisinin. Artemisinin in methanol is reduced with sodium borohydride to an equilibrium mixture of Δ-and E-isomers of dihydroartemisinin. The yield under controlled conditions is 79% (artemisinin, 0.85M with NaBH$_4$ 6:34M, 7:5 equivalents in methanol, 12 L at 0–5° C. for about 3 hours followed by quenching with acetic acid to neutrality at 0–5° C. and dilution with water to precipitate dihydroartemisinin), A. Brossi, et al., *Journal of Medicinal Chemistry*, 31:645–650 (1988). Using dihydroartemisinin as a starting compound a large number of other derivatives, such as,

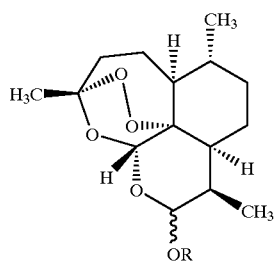

1 R=H
2 R=CH$_3$
3 R=CH$_2$CH$_3$
4 R=COCH$_2$CH$_2$COONa
5 R=CH$_2$C$_6$H$_4$COOH
6 R=CH$_2$C$_6$H$_4$COONa
7

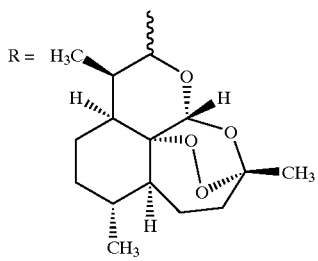

artemether (compound II-2), arteether (II-3), sodium artesunate (II-4), artelinic acid (II-5), soduim artelinate (II-6), dihydroartemisinin condensation by-product (II-7) and the olefinic compound structure III,

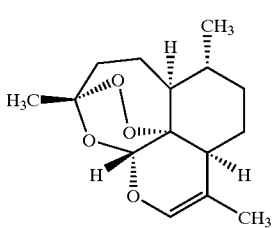

have been produced.

Artemether (II-2) is produced by reacting E-dihydroartemisinin with boron trifluoride (BF$_3$) etherate or HCl in methanol:benzene (1:2) at room temperature. A mixture of E-and Δ-artemether (70:30) is obtained, from which the former is isolated by colunm chromatography and recrystallized from hexane or methanol, R. Haynes, *Transactions of the Royal Society of Tropical Medicine and Hygiene*, 88(1): S1/23–S1/26 (1994). For arteether (II-3), (Brossi, et al., 1988), the Δ-isomer is equilibrated (epimerized) to the E-isomer in ethanol:benzene mixture containing BF$_3$ etherate. Treatment of dihydroartemisinin with an unspecified dehydrating agent yields both the olefinic compound, (III), and the dihydroartemisinin condensation by-product (II-7), formed on addition of dihydroartemisinin to (III), M. Cao, et al., *Chem. Abstr.*, 100:34720k (1984). Until recently, the secondary hydroxy group in dihydroartemisinin (II-1) provided the only site in an active artemisinin-related compound that had been used for derivatization. See B. Venugopalan, "Synthesis of a Novel Ring Contracted Artemisinin Derivative," *Bioorganic & Medicinal Chemistry Letters*, 4(5):751–752 (1994).

The potency of various artemisinin-derivatives in comparison to artemisinin as a function of the concentration at which the parasitemia is 90 percent suppressed (SD$_{90}$) was reported by D. L. Klayman, "Qinghaosu (Artemisinin): An Antimalarial Drug from China," *Science* 228:1049–1055 (1985). Dr. Klayman reported that the olefinic compound III is inactive against *P. berghei*-infected mice, whereas the dihydroartemisinin condensation by-product (II-7) has an SD$_{90}$ of 10 mg/Kg in *P. berghei*-infected mice. Thus, the dihydroartemisinin ether dimer proved to be less potent than artemisinin, which has an SD$_{90}$ of 6.20 mg/Kg. Following, in order of their overall antimalarial efficacy, are the three types of derivatives of dihydroartemisinin (II-1) that have been produced: (artemisinin)<ethers (II, R=alkyl)<esters [II,=C(=O)-alkyl or -aryl]<carbonates [II, R=C (=O)O-alkyl or -aryl].

Other rational design of structurally simpler analogs of artemisinin has led to the synthesis of various trioxanes, some of which possess excellent antimalarial activity. Posner, G. H., et al., reported the chemistry and biology of a series of new structurally simple, easily prepared, racemic 1,2,4-trioxanes (disclosed in U.S. Pat. No. 5,225,437 and incorporated herein by reference) that are tricyclic (lacking the lactone ring present in tetracyclic artemisinin I) and that are derivatives of trioxane alcohol IV.

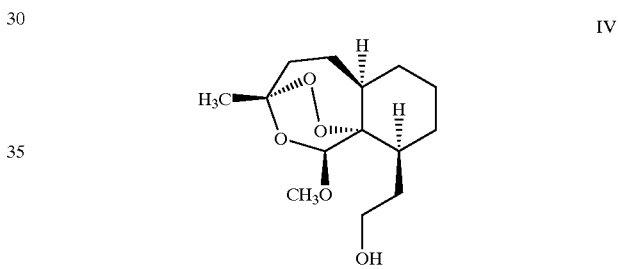

having the relative stereochemistry shown above. Especially attractive features of trioxane alcohol IV are the following: (1) its straightforward and easy preparation from cheap and readily available starting materials, (2) its availability on gram scale, and (3) its easy one-step conversion, using standard chemical transformations, into alcohol derivatives such as esters and ethers, without destruction of the crucial trioxane framework. See, Posner, G. H., et al., *J Med Chem.*, 35:2459–2467 (1992), incorporated herein by reference. The complete chemical synthesis of artemisinin and a variety of other derivatives is reviewed by Sharma, R. P., et al., *Heterocycles*, 32(8):1593–1638 (1991), and is incorporated herein by reference.

Metabolic studies by Baker, et al., demonstrated that B-arteether (II-3), one of the antimalarial derivatives discussed previously, was rapidly converted by rat liver microsomes into dihydroartemisinin (II-1). See Baker, J. K., et al., *Biol. Mass Spect.*, 20:609–628 (1991). This finding and the fact that the most effective artemisinin derivatives against malaria have been ethers or esters of (II-1) suggest that they were prodrugs for (II-1). The controlled slow formation of (II-1), however, is not desirable in view of its short half-life in plasma (less than two hours) and relatively high toxicity.

The successful synthesis of anticancer and antiviral drugs by replacing a carbon-nitrogen bond in nucleosides by a- carbon-carbon bond (C-nucleosides) prompted the preparation of several 10-alkyldeoxoartemisinins, V,

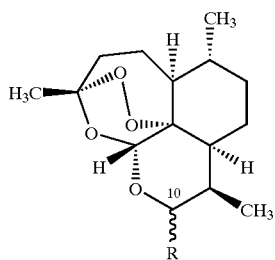

V wherein R is 1-allyl, propyl, methyl, or ethyl. Typically, these syntheses involved five or six steps and the reported yields were only about 12 percent. See, Jung, M., et al., *Synlett.*, 743–744 (1990); and Haynes, R. K., et al, *Synlett.*, 481–484 (1992).

Heterolytic cleavage of the peroxide O—O bond via $S_N2$ attack of nucleophiles is well documented., see Adam, W. et al, *J Am. Chem. Soc.*, 114:5591 (1992) and Razuvaev, G. A., et al, T. G. *In Organic Peroxides*; D. Swem, Ed., John Wiley & Sons, New York, 3:141–270, (1972). For example, tert-butyl ethers are conveniently prepared by Grignard nucleophilic attack on the O—O bond in tert-butyl peresters, see Lawesson, S.-O., et al., *J. Am. Chem. Soc.*, 81:4230, (1959). Also, 3,3-disubstituted-1,2-dioxetanes react with organolithium reagents primarily via $S_N2$ O—O bond cleavage (with regioselective attack at the sterically less encumbered O atom) to form E-hydroxy ethers (Adam, W., et al., *Chem. Ber*, 125:235, (1992)) and bicyclic endoperoxides likewise react with lithium and magnesium organometallics to produce O—O bond-cleaved hydroxy ethers. See, Schwaebe, M. K., et al, *Tetrahedron Lett.*, 37:6635 (1996). When a dialkyl peroxide O—O bond is sterically hindered, then nucleophilic attack by a reactive organometallic reagent is made more difficult; an excellent example of this phenomenon leading to chemoselective nucleophilic addition of an organolithium reagent to the aldehyde carbonyl group in a peroxy aldehyde. See, Dussault, P., et al., *T. J. Org. Chem.*, 58:5469 (1993) and Dussault, P., *Synlett*, 997 (1995). 1,2, 4-Trioxanes in the artemisinin family undergo peroxide O—O bond cleavage when exposed to dimethylcopperlithium and to tritylithium; in these two cases, however, single-electron-reductive cleavage of the peroxide bond is likely occurring. See, Posner, G. H. et al., *J Am. Chem. Soc.*, 114:8328 (1992). Sodium borohydride chemoselectively reduces artemisinin (I) into its lactol (II-1), but more potent lithium aluminum hydride reduces both the lactone carbonyl group and the trioxane O—O bond. See, Wu, Y, et al, *Youji Huaxue*, 153, (1986); *Chem. Abstr.* 1986, 105, 191426n.

Based on these published precedents, it seemed that it would be very difficult to find any reactive organometallic reagents that would add chemoselectively to the lactone carbonyl group (less electrophilic than an aldehyde) of trioxane lactone artemisinin (I) without also cleaving the trioxane O—O bond. In fact, exposing artemisinin to 1.2 equivalent of phenyllithium in THF at –78° C. produced at least three major products (not characterized).

Over the past thirty years only a few drugs isolated from higher plants have yielded clinical agents, the outstanding examples being vinblastine and vincristine from the Madagascan periwinkle, *Catharanthus roseus*, etoposide, the semi-synthetic lignan, from Mayapple *Podophyllum peltatum* and the diterpenoid taxol, commonly referred to as paclitaxel, from the Pacific yew, *Taxus brevifolia*. Of these agents, paclitaxel is the most exciting, recently receiving approval by the Food and Drug Administration for the treatment of refractory ovarian cancer. Since the isolation of artemisinin, there has been a concerted effort by investigators to study other therapeutic applications of artemisinin and its derivatives.

National Institutes of Health reported that artemisinin is inactive against P388 leukemia. See NCI Report on NSC 369397 (tested on Oct. 25, 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that artemisinin displays very little anticancer activity. A series of artemisinin-related endoperoxides were tested for cytotoxicity to Ehrlich ascites tumor (EAT) cells using the microculture tetrazolum (MTT) assay, H. J. Woerdenbag, et al., "Cytotoxicity of Artemisinin-Related Endoperoxides to Ehrlich Ascites Tumor Cells," *Journal of Natural Products*, 56(6):849–856 (1993). The MTT assay, used to test the artemisinin-related endoperoxides for cytotoxicity, is based on the metabolic reduction of soluble tetrazolium salts into insoluble colored formazan products by mitochondrial dehydrogenase activity of the tumor cells. As parameters for cytotoxicity, the $IC_{50}$ and $IC_{80}$ values, the drug concentrations causing respectively 50% and 80% growth inhibition of the tumor cells, were used. Artemisinin (I) had an $IC_{50}$ value of 29.8 Π M. Derivatives of dihydroartemisinin (II-1) being developed as antimalarial drugs (artemether (II-2), arteether (III-3), sodium artesunate (II-4), artelinic acid (II-5) and sodium artelinate (II-6)), exhibited a somewhat more potent cytotoxicity. Their $IC_{50}$ values ranged from 12.2 Π M to 19.9 Π M. The dihydroartemisinin condensation by-product dimer (II-7), disclosed previously by M. Cao, et al., 1984, was the most potent cytotoxic agent, its $IC_{50}$ being 1.4 Π M. At this drug concentration the condensation by-product (II-7) is approximately twenty-two times more cytotoxic than artemisinin and sixty times more cytotoxic than dihydroartemisinin (II-1), the parent compound.

While artemisinin and its related derivatives (II1–6) discussed above demonstrated zero to slight antiproliferative and antitumor activity, it has been discovered that a class of artemisinin dimer compounds exhibits antiproliferative and antitumor activities that are, in vitro, equivalent to or greater than known antiproliferative and antitumor agents. See, U.S. Pat. No. 5,677,468 incorporated herein by reference. Unfortunately, while the in vitro results of these artemisinin compounds are encouraging these compounds do not appear to have significant antitumor activity on the treatment of tumor cells in mice.

There is still a need, therefore, to develop methods for the formation of hydrolytically stable C-10 carbon-substituted artemisinin compounds and structural analogs thereof having antimalarial, and antiproliferative and antitumor activities that are equivalent to or greater than those of known antimalarial, and antiproliferative and antitumor agents, respectively, wherein the method does not result in cleavage of the trioxane O—O bond.

SUMMARY OF THE INVENTION

Accordingly, this invention provides a class of artemisinin related dimers which demonstrate antiproliferative and antitumor activities.

More specifically, this invention provides a class of trioxane dimers which demonstrate antiproliferative and antitumor activities and that are considerably more stable than artemether and related C-10 ethers and esters toward hydrolysis.

This invention further provides artemisinin dimers to be used clinically as chemotherapeutic anticancer drugs.

This invention further provides a class of trioxane monomers to be used clinically as chemotherapeutic antimalarial drugs and methods of producing the same.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the compositions of this invention comprise C-10 carbon-substituted derivatives of the trioxane exocyclic alkene (VII) of the following structure

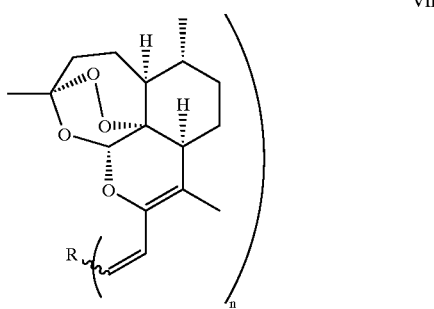

VII or diastereomers thereof, having antimalarial, and antiproliferative and antitumor activities wherein, the monomers of the present invention are formed when n is 1 and R is alkyl, cycloalkyl, heteroalkyl, heterocycloalkyl, alkenyl, alkynyl, aryl or heteroaryl. The term "alkyl" includes straight chain or branched alkyl compounds comprising 1–20 carbon atoms and cyclic alkyl compounds comprising 5–10 carbon atoms. The term "heteroalkyl" includes polyalkylene glycols such as polyethylene glycol (PEG). The term "aryl" means a phenyl or phenyl group substituted by 1 or more substituents selected from the group comprising halogen, nitro, amino, hydroxy, thiohydroxy, lower alkoxy, lower thioalkyl, lower alkyl, NHC(=O)R wherein R is aryl or lower alkyl, COOH, or COOR$_2$ wherein R$_2$ is aryl or lower alkyl. The term "heteroaryl" includes 5 or 6 membered heteroaromatic rings comprising one or more heteroatoms selected from N, O or S, unsubstituted or substituted by halogen, nitro, amino, hydroxy, thiohydroxy, lower alkoxy, lower alkyl, NHC(=O)R$_1$ wherein R is aryl or lower alkyl, COOH, or COOR$_2$ wherein R$_2$ is aryl or lower alkyl. The term "lower alkyl" means straight or branched hydrocarbon radicals comprising 1–20 carbon atoms and include, for example, methyl, ethyl, n-propyl, isopropyl, n-butyl, t-butyl, n-pentyl and the like. "Halogen" is fluorine, chlorine, bromine or iodine.

The dimers of the present invention are formed when n is 2 and R is a linker including, but not limited to, alkyl, cycloalkyl, heteroalkyl, heterocycloalkyl, alkenyl, alkynyl, aryl or heteroaryl. The term "alkyl" includes straight chain or branched bivalent alkyl compounds comprising 1–20 carbon atoms and cyclic alkyl compounds comprising 5–10 carbon atoms. The term "heteroalkyl" includes bivalent polyalkylene glycols such as polyethylene glycol (PEG). The term "aryl" means a bivalent phenyl or phenyl group substituted by 1 or more substituents selected from the group comprising halogen, nitro, amino, hydroxy, thiohydroxy, lower alkoxy, lower thioalkyl, lower alkyl, NHC(=O)R$_1$ wherein R$_1$ is aryl or lower alkyl, COOH, or COOR$_2$ wherein R$_2$ is aryl or lower alkyl. The term "heteroaryl" includes bivalent 5 or 6 membered heteroaromatic rings comprising one or more heteroatoms selected from N, O or S, unsubstituted or substituted by halogen, nitro, amino, hydroxy, thiohydroxy, lower alkoxy, lower alkyl, NHC(=O)R$_1$ wherein R$_1$ is aryl or lower alkyl, COOH, or COOR$_2$ wherein R$_2$ is aryl or lower alkyl. The term "lower alkyl" means straight or branched hydrocarbon radicals comprising 1–20 carbon atoms and include, for example, methyl, ethyl, n-propyl, isopropyl, n-butyl, t-butyl, n-pentyl and the like. "Halogen" is fluorine, chlorine, bromine or iodine.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In the drawing, FIG. 5, the horizontal axis depicts various dilutions of the test compounds, ranging from $10^{-6}$ to $7 \times 10^{-9}$ molar, that were exposed to murine keratinocytes. The vertical axis (cell number) depicts the number of murine keratinocyte cells present after exposure to a specific concentration of the tested compound as compared to the cell number at time zero.

Figure 1:
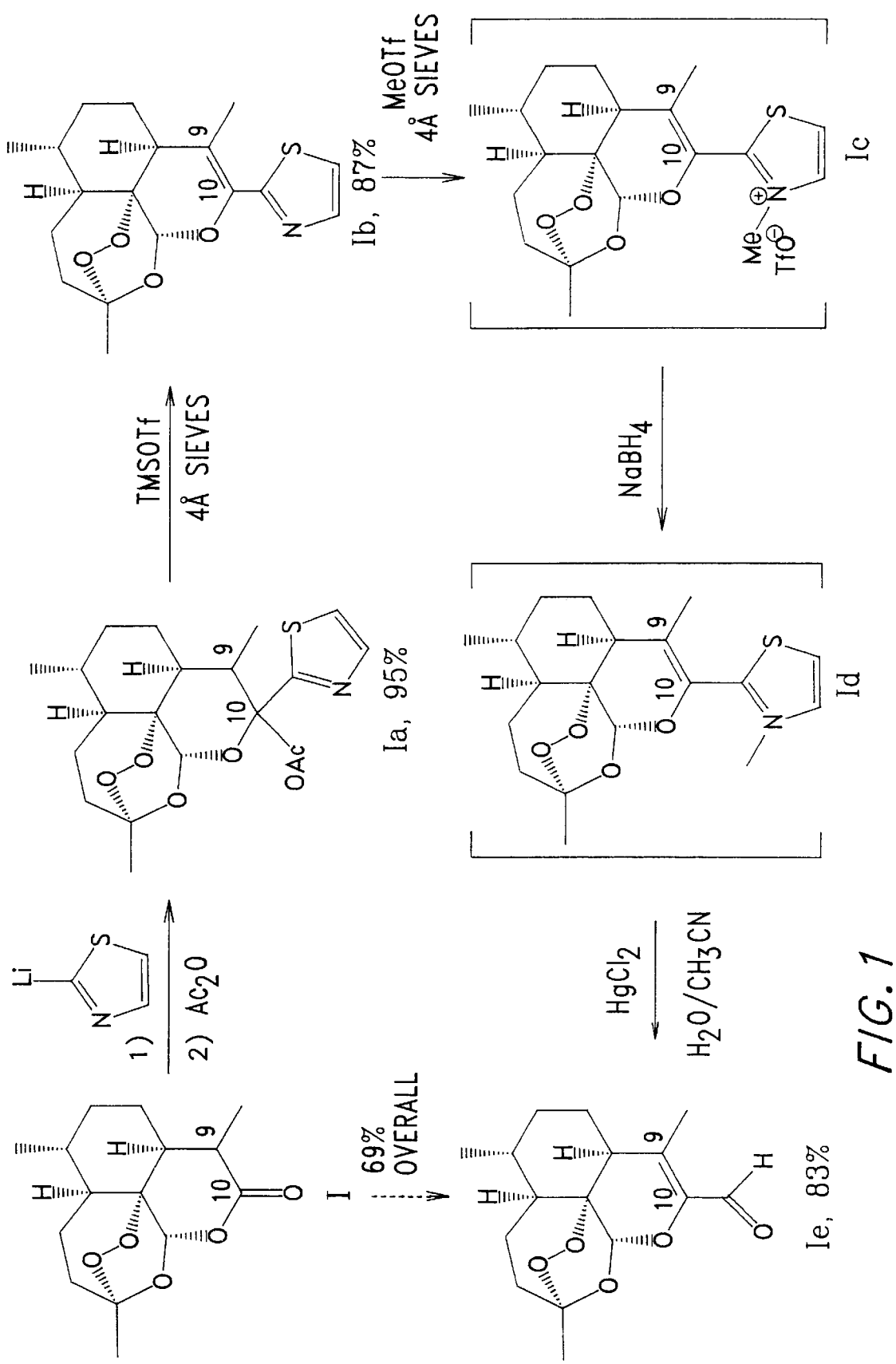

In the drawings, FIGS. 6–14, the horizontal axis depicts various dilutions of the test compound, ranging from $10^{-4}$ to $10^{-9}$ molar, that were exposed to the specified cancer cell lines. The vertical axis (percentage growth) depicts the growth of the specified cancer cell line when exposed to a specific concentration of the tested compound as compared to the growth of the same cancer cell line not exposed to any compound.

In the Drawings:

FIG. 1 schematically depicts the method of converting artemisinin I into the 9,10-unsaturated C-10 alkylidenated aldehyde VII of the present invention.

Figure 2:
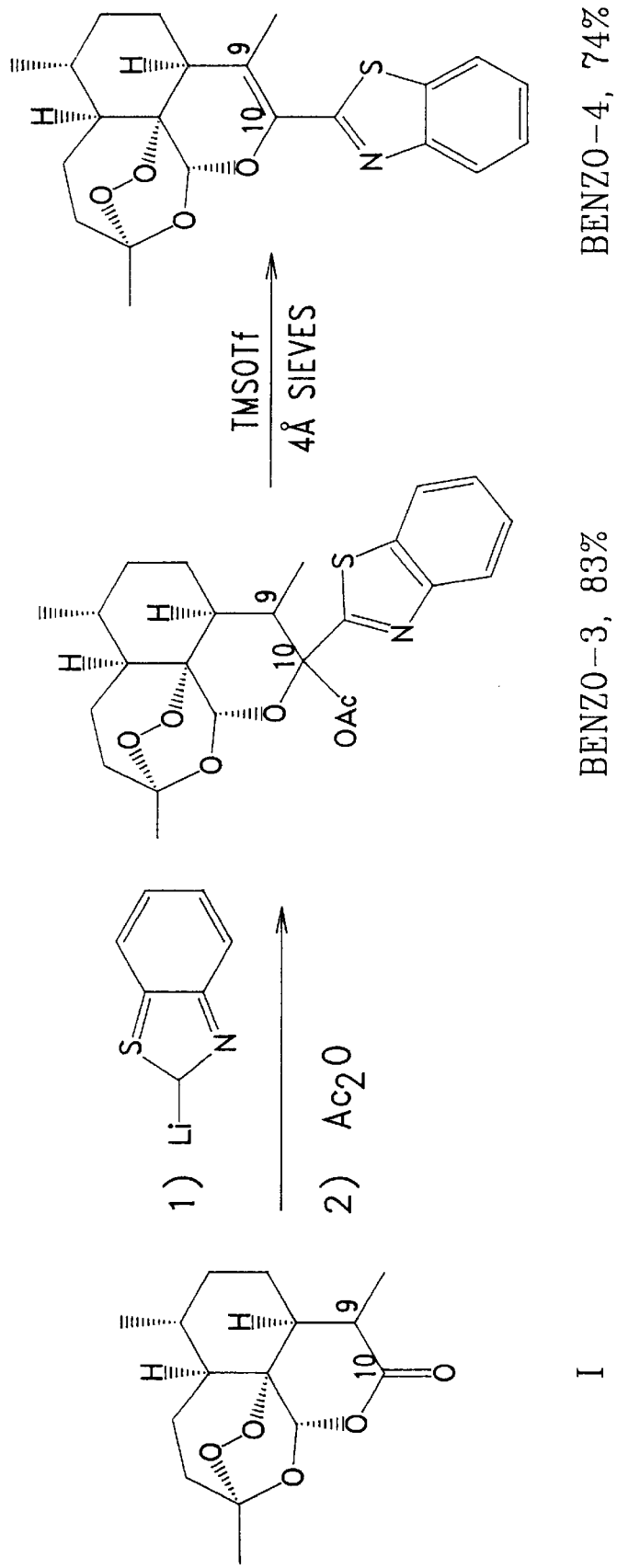

FIG. 2 schematically depicts the method of converting artemisinin I into an alkene benzothiazole-4 artemisinin analogue of the present invention.

Figure 3:
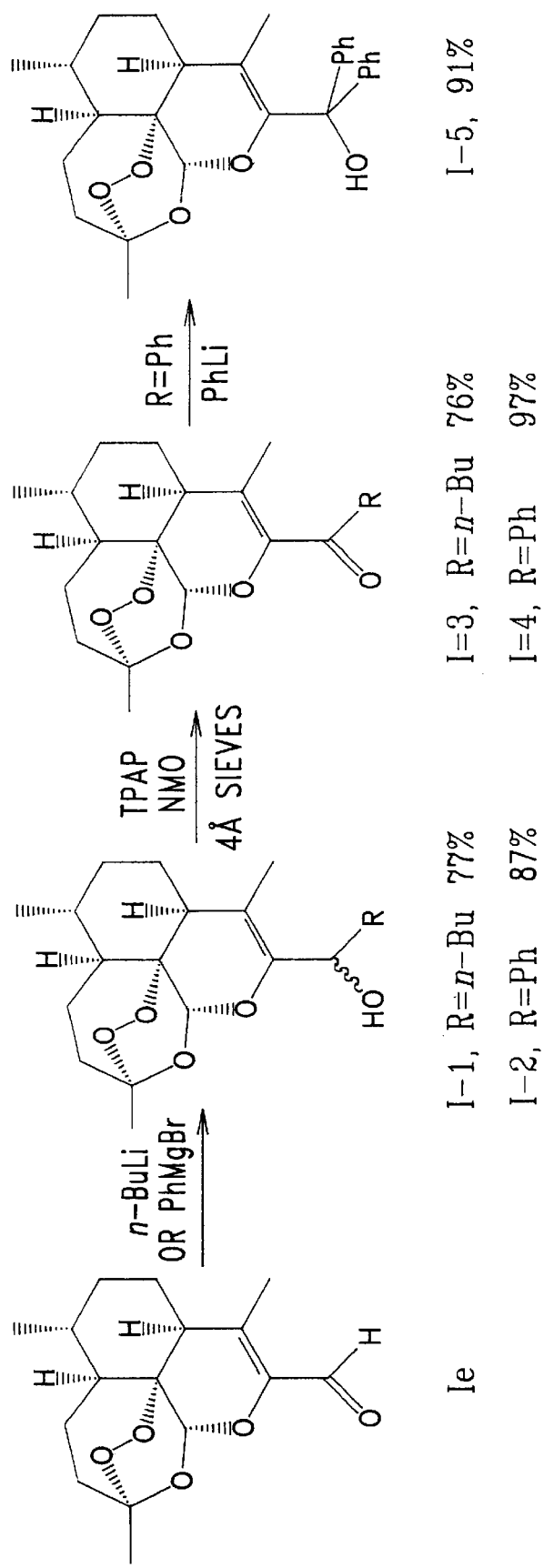

FIG. 3 schematically depicts the formation of artemisinin analogues of the present invention by organometallic nucleophilic addition to the carbonyl group of the trioxane enal Ie.

Figure 4:
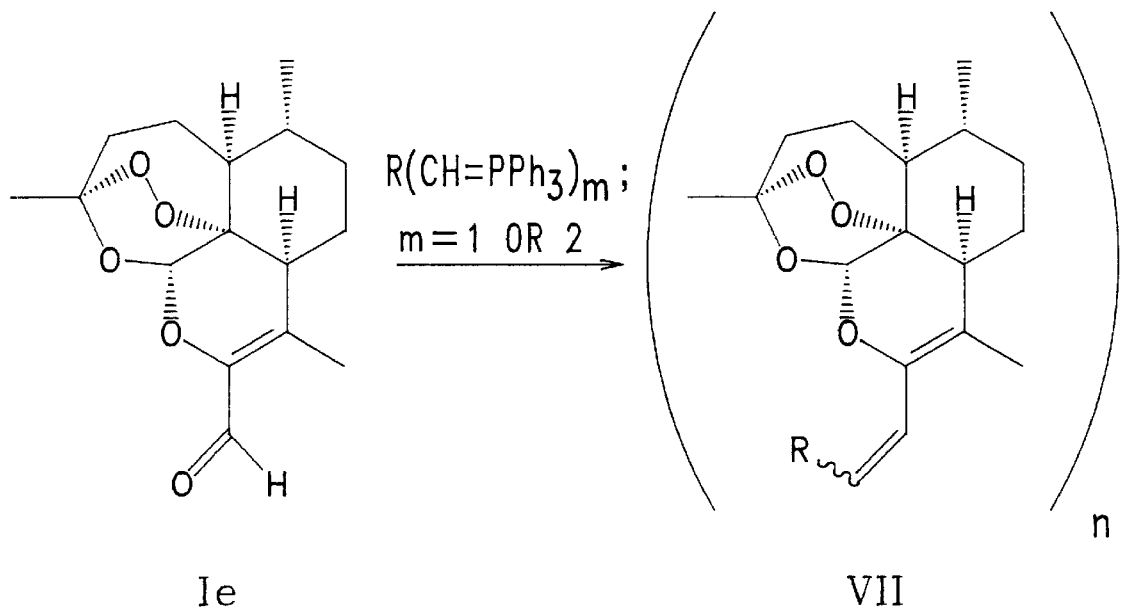

FIG. 4 schematically depicts the formation monomeric and dimeric exocyclic alkene analogues of artemisinin by reacting nucleophilic phosphonium ylides with the trioxane enal Ie.

Figure 5:
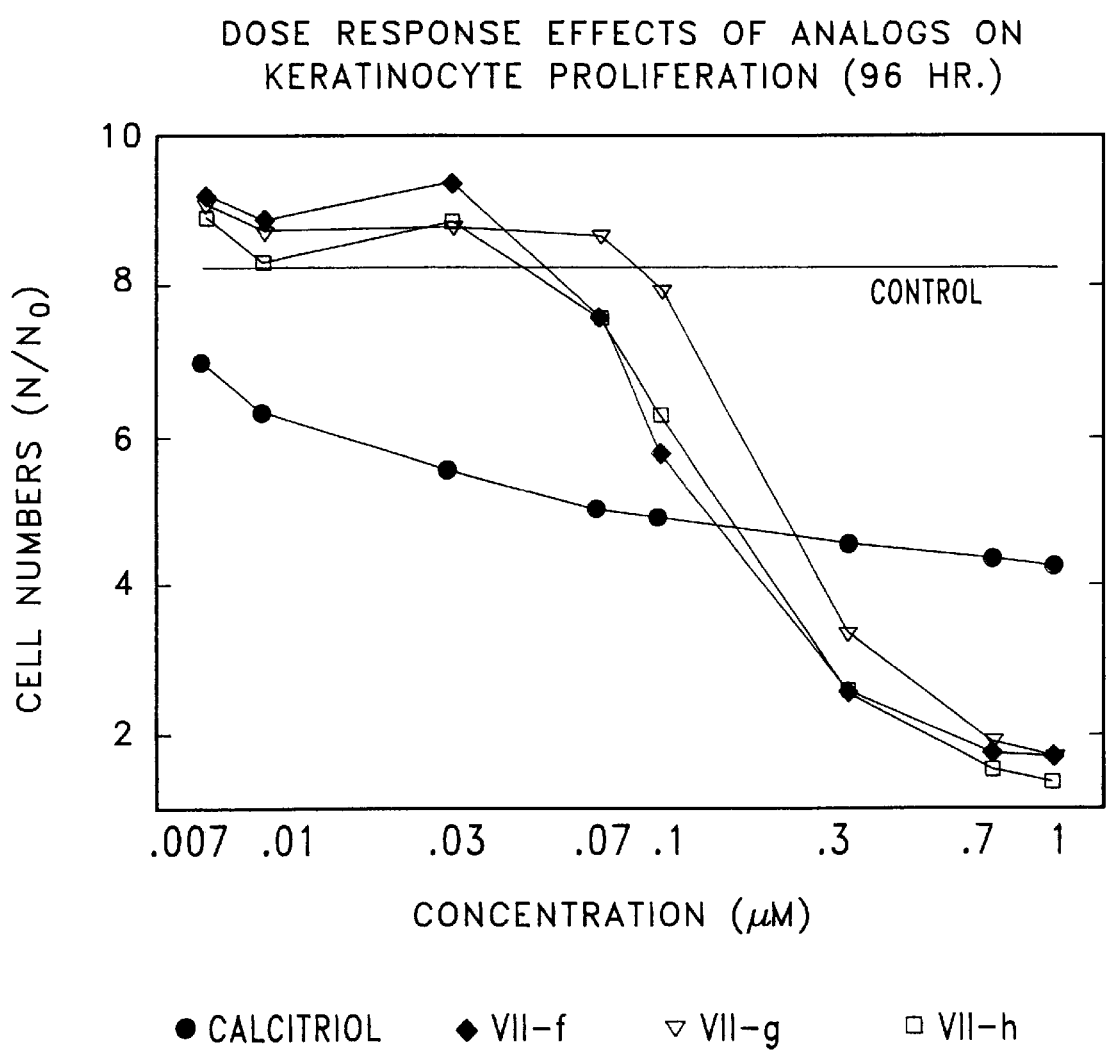

FIG. 5 depicts the dose response curves generated by exposing murine keratinocytes to various concentrations of the C-10 carbon-substituted trioxane dimers VII-f, VII-g, and VII-h of the present invention versus calcitriol and versus a control using only a solvent.

Figure 6A:
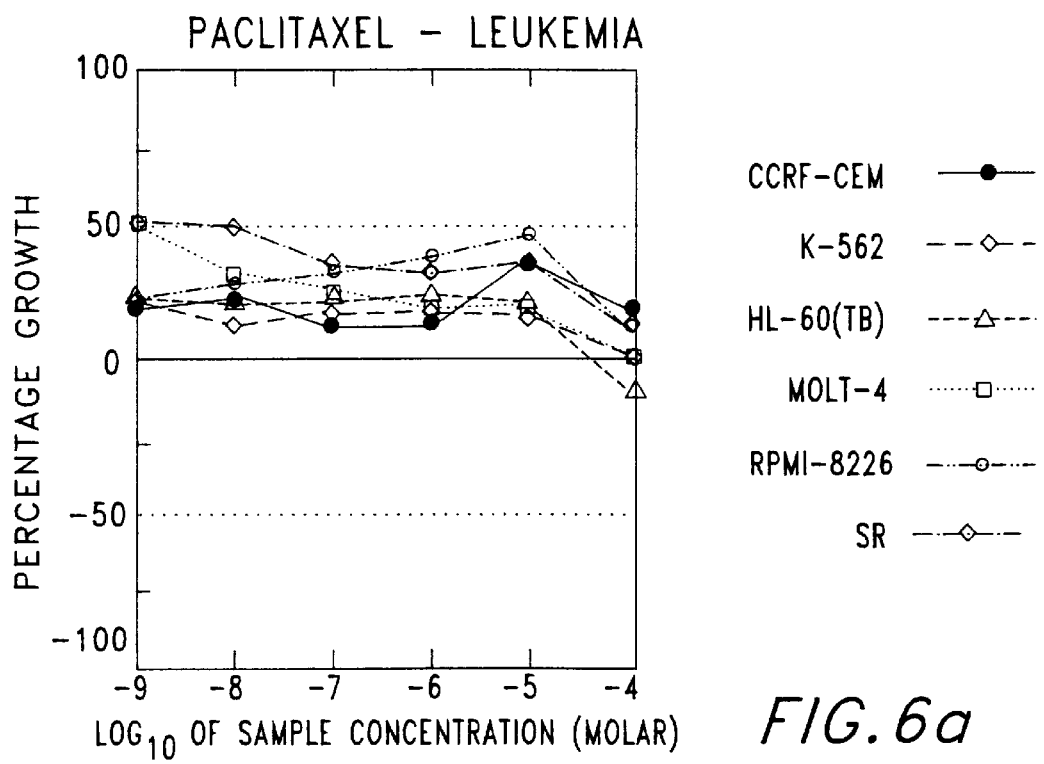

FIG. 6a depicts the dose response curves generated by exposing various leukemia cancer cell lines to various concentrations of paclitaxel.

Figure 6B:
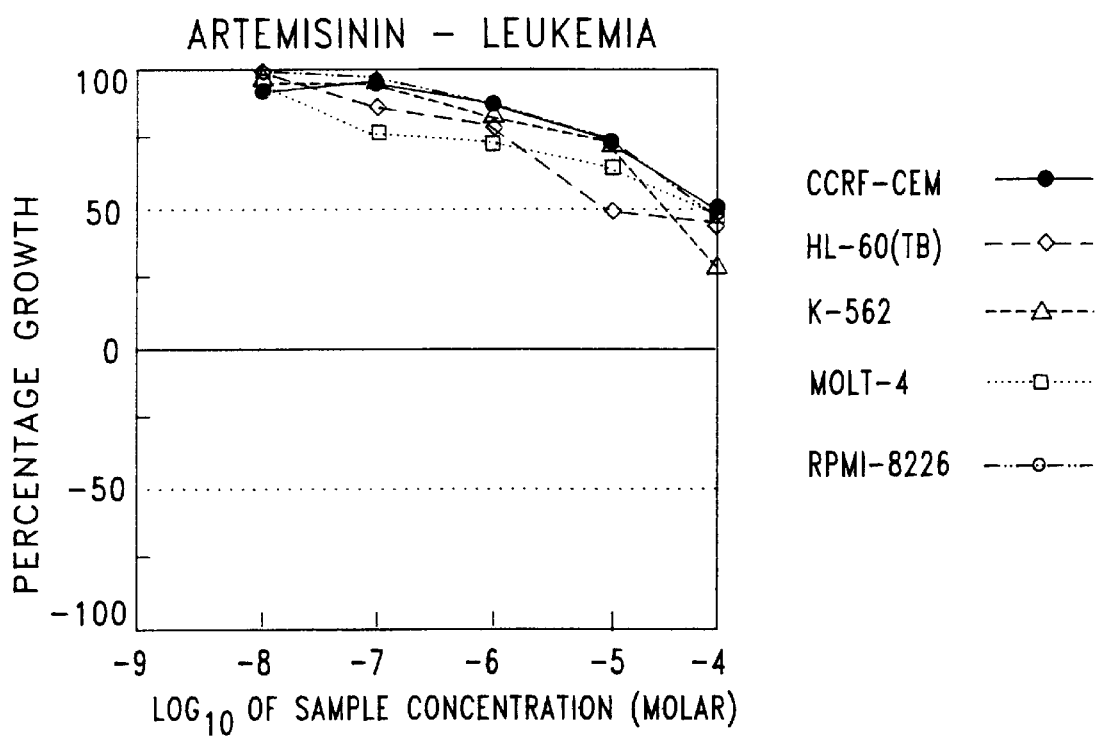

FIG. 6b depicts the dose response curves generated by exposing various leukemia cancer cell lines to various concentrations of artemisinin.

Figure 6C:
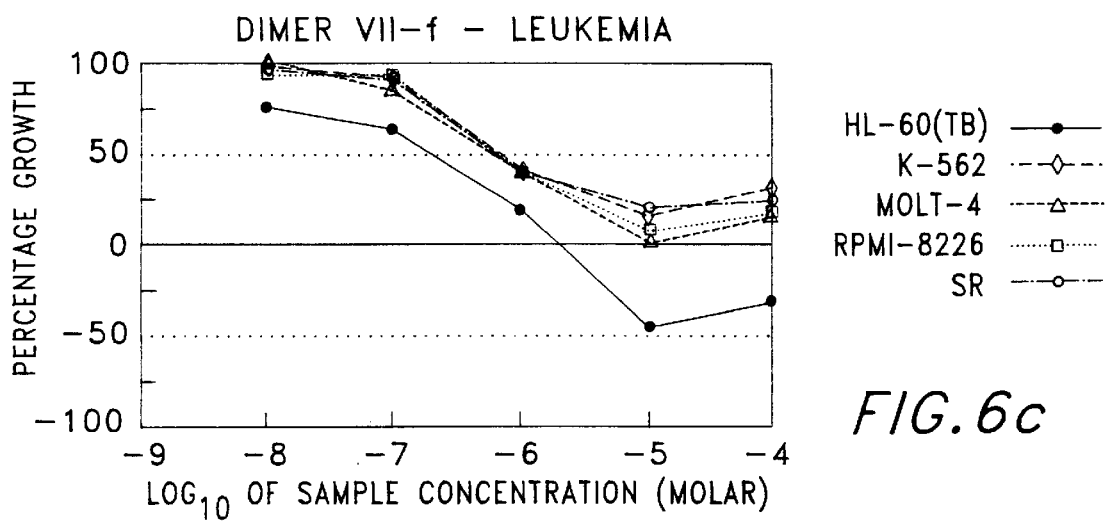

FIG. 6c depicts the dose response curves generated by exposing various leukemia cancer cell lines to various concentrations of the C-10 carbon-substituted dimer VII-f of the present invention.

Figure 6D:
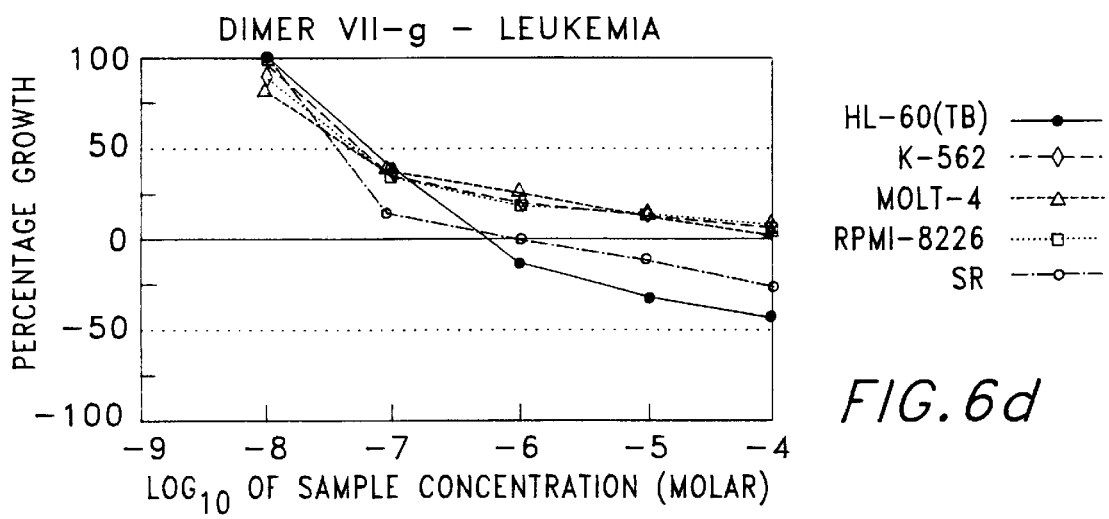

FIG. 6d depicts the dose response curves generated by exposing various leukemia cancer cell lines to various concentrations of the C-10 carbon-substituted dimer VII-g of the present invention.

Figure 6E:
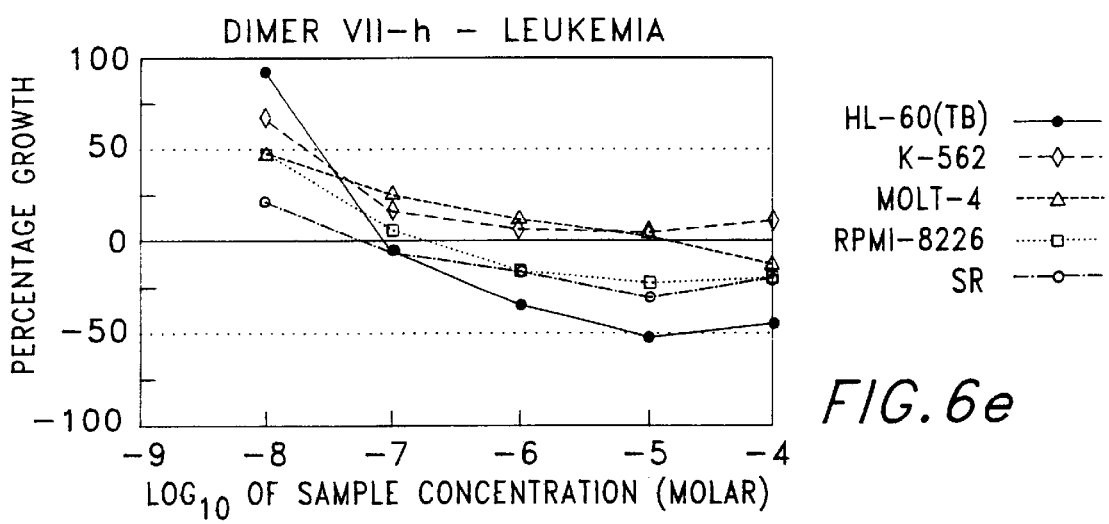

FIG. 6e depicts the dose response curves generated by exposing various leukemia cancer cell lines to various concentrations of the C-10 carbon-substituted dimer VII-h.

Figure 7A:
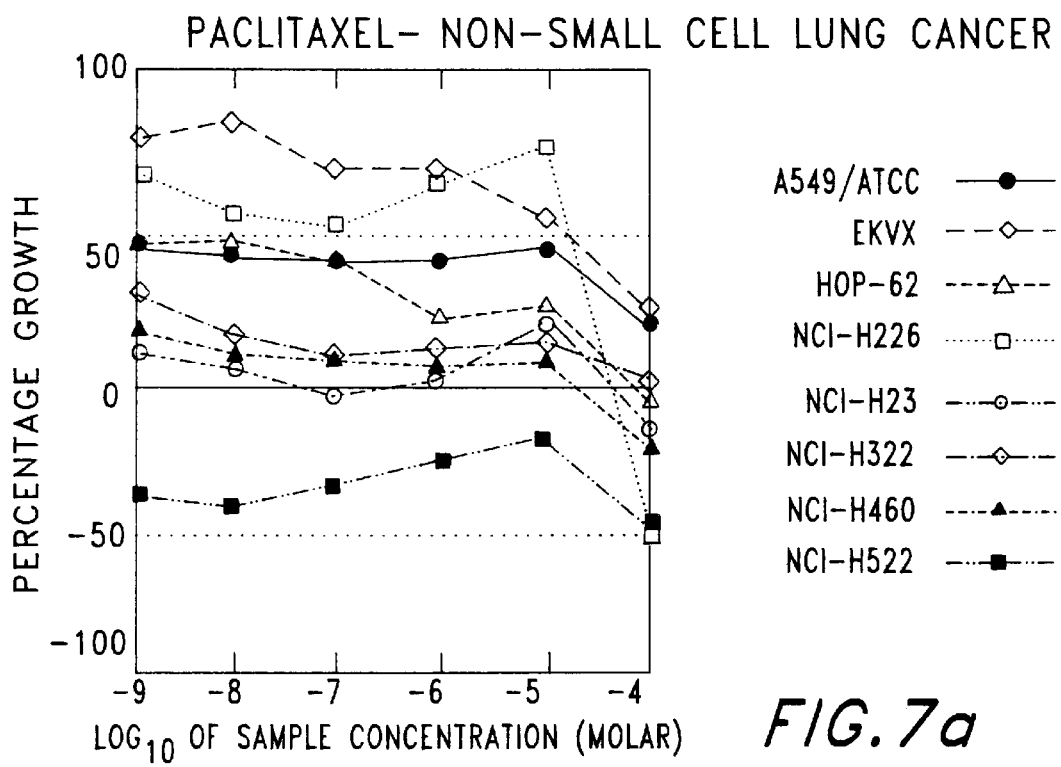

FIG. 7a depicts the dose response curves generated by exposing various non-small cell lung cancer cell lines to various concentrations of paclitaxel.

Figure 7B:
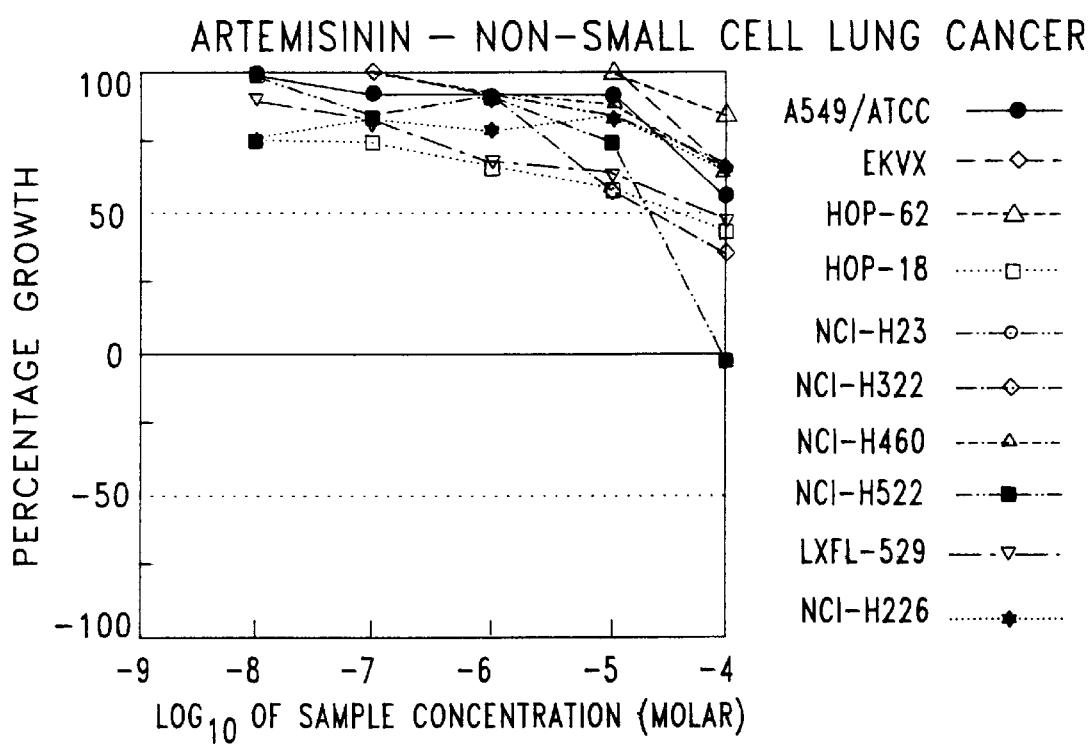

FIG. 7b depicts the dose response curves generated by exposing various non-small cell lung cancer cell lines to various concentrations of the artemisinin.

Figure 7C:
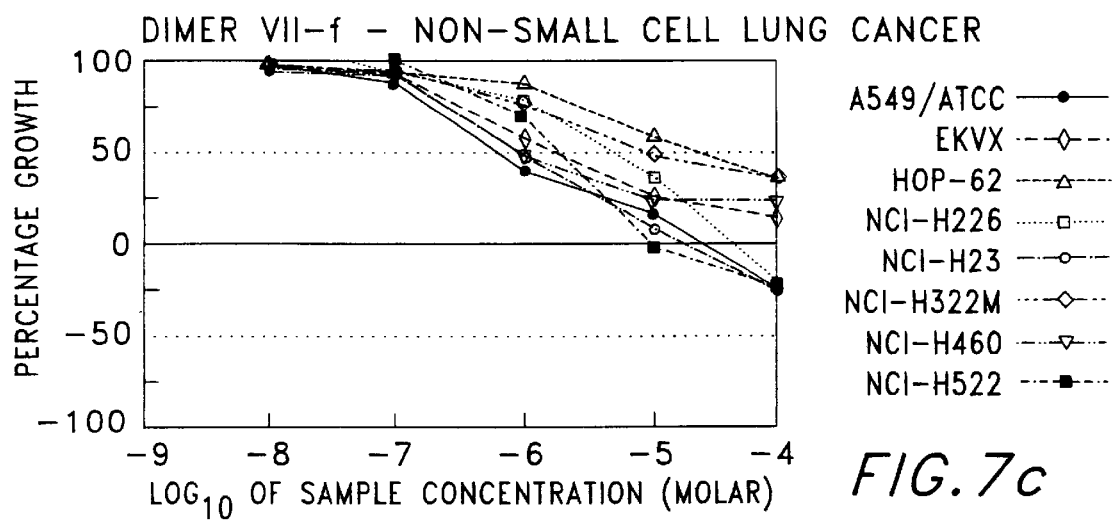

FIG. 7c depicts the dose response curves generated by exposing various non-small cell lung cancer cell lines to various concentrations of the C-10 carbon-substituted dimer VII-f of the present invention.

Figure 7D:
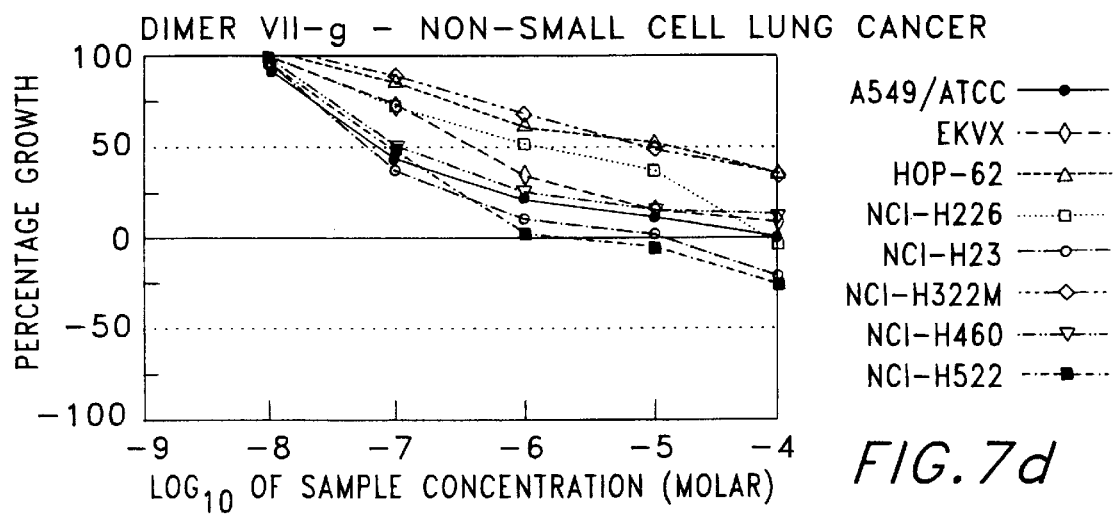

FIG. 7d depicts the dose response curves generated by exposing various non-small cell lung cancer cell lines to various concentrations of the C-10 carbon-substituted dimer VII-g of the present invention.

Figure 7E:
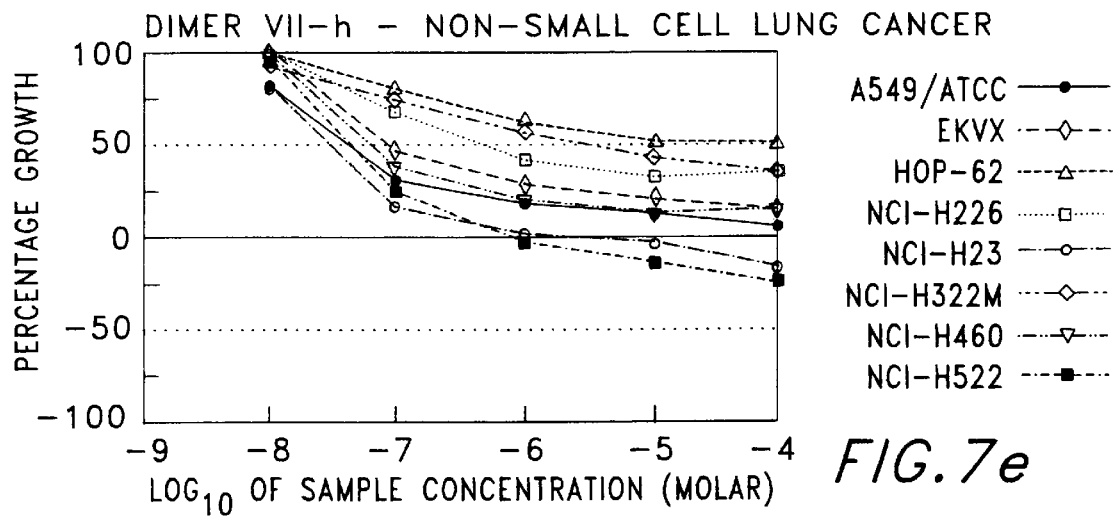

FIG. 7e depicts the dose response curves generated by exposing various small cell lung cancer cell lines to various concentrations of the C-10 carbon-substituted dimer VII-H.

Figure 8A:
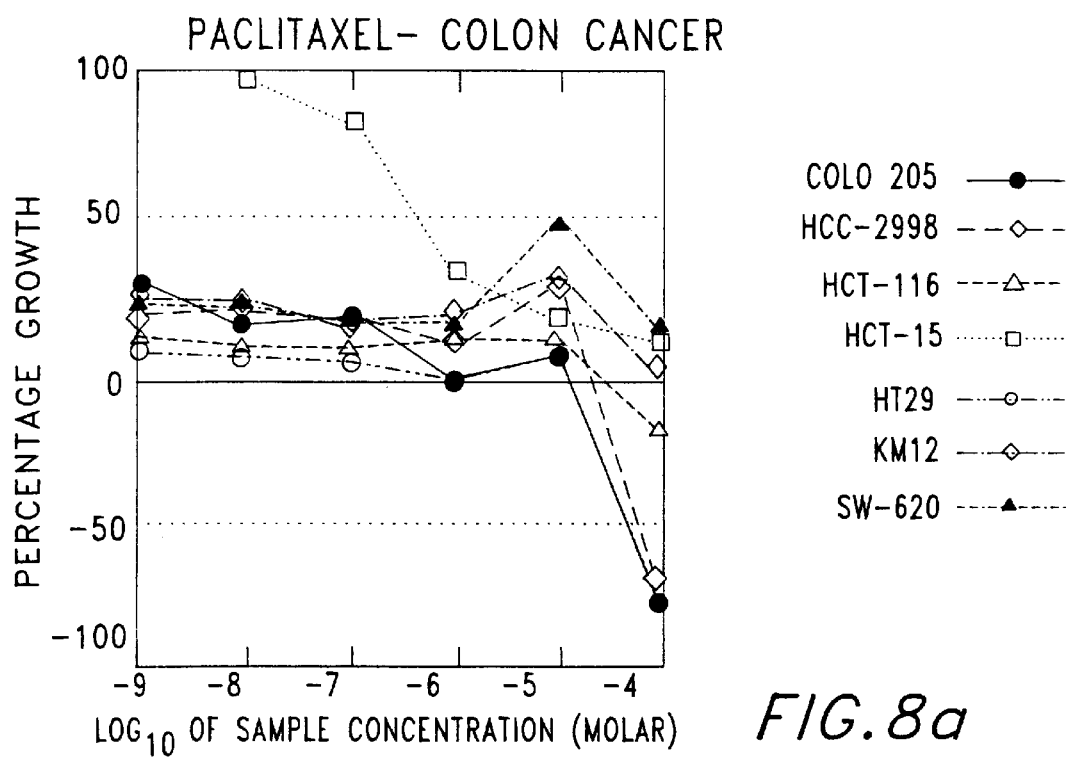

FIG. 8a depicts the dose response curves generated by exposing various colon cancer cell lines to various concentrations of paclitaxel.

Figure 8B:
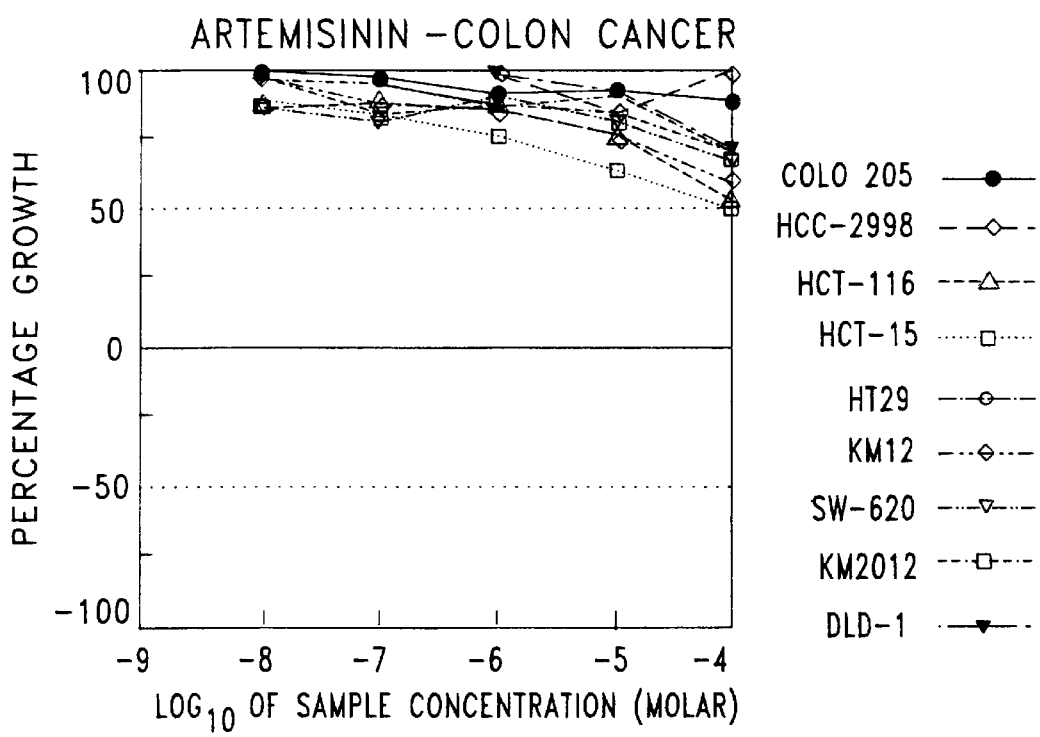

FIG. 8b depicts the dose response curves generated by exposing various colon cancer cell lines to various concentrations of artemisinin.

Figure 8C:
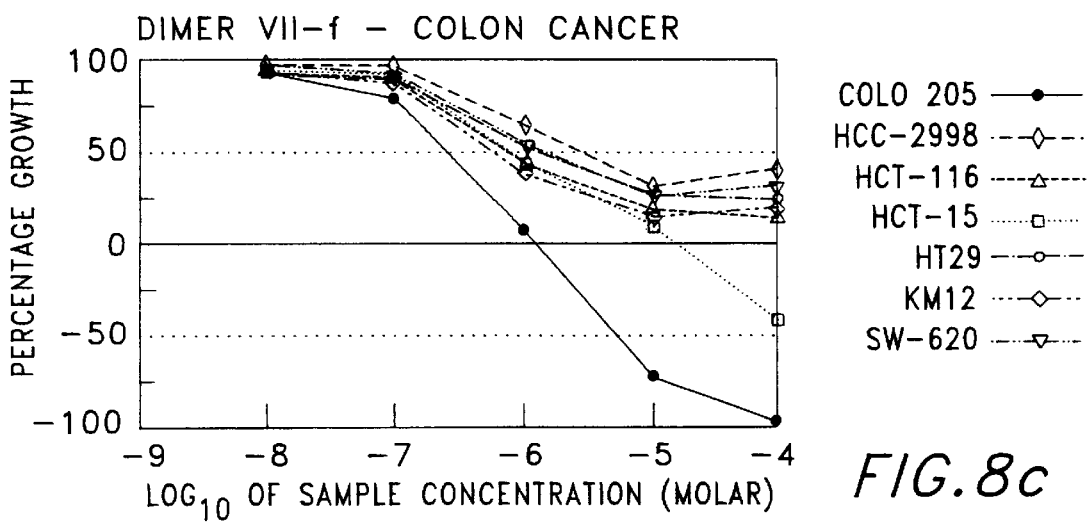

FIG. 8c depicts the dose response curves generated by exposing various colon cancer cell lines to various concentrations of the C-10 carbon-substituted dimer VII-f of the present invention.

Figure 8D:
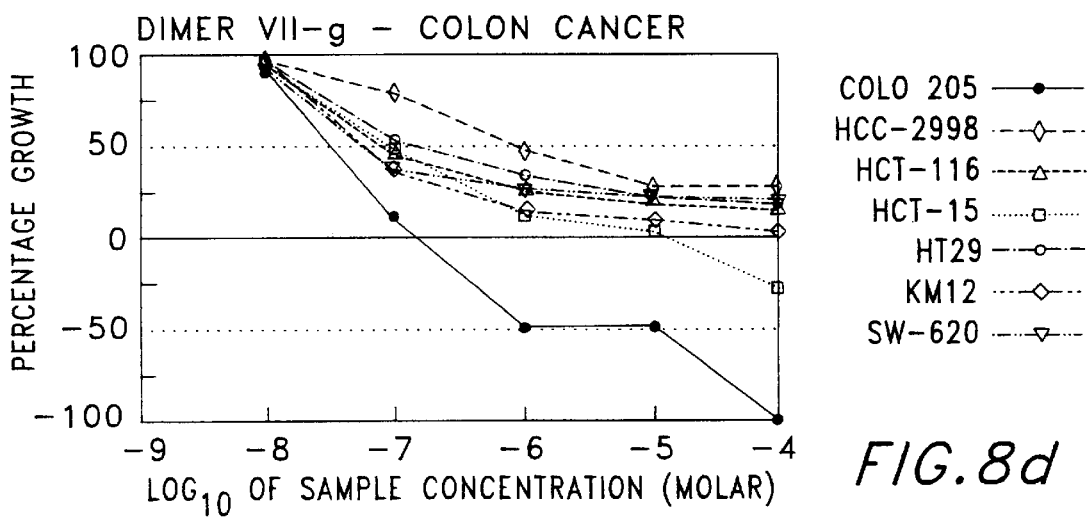

FIG. 8d depicts the dose response curves generated by exposing various colon cancer cell lines to various concentrations of the C-10 carbon-substituted dimer VII-g of the present invention.

Figure 8E:
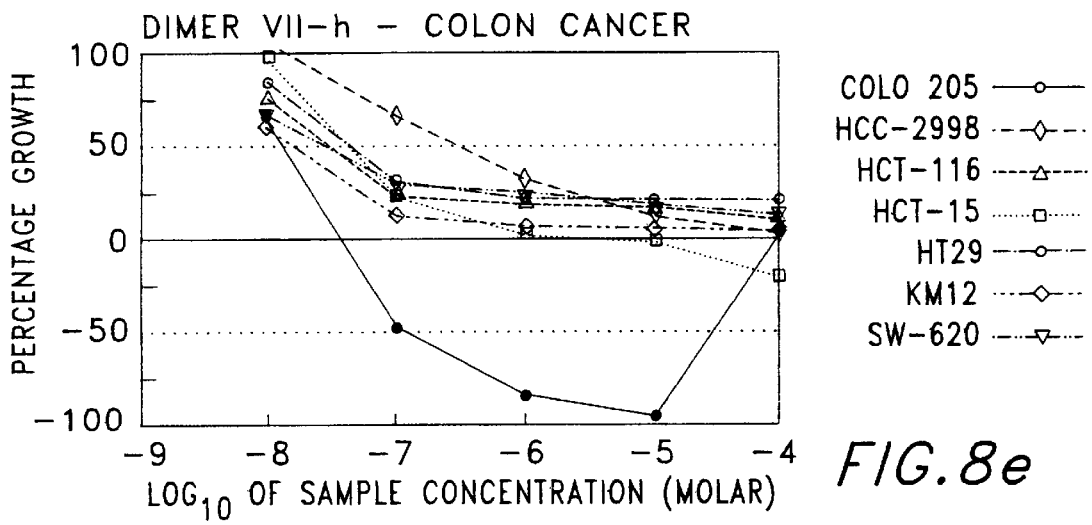

FIG. 8e depicts the dose response curves generated by exposing various colon cancer cell lines to various concentrations of the C-10 carbon-substituted dimer VII-h.

Figure 9A:
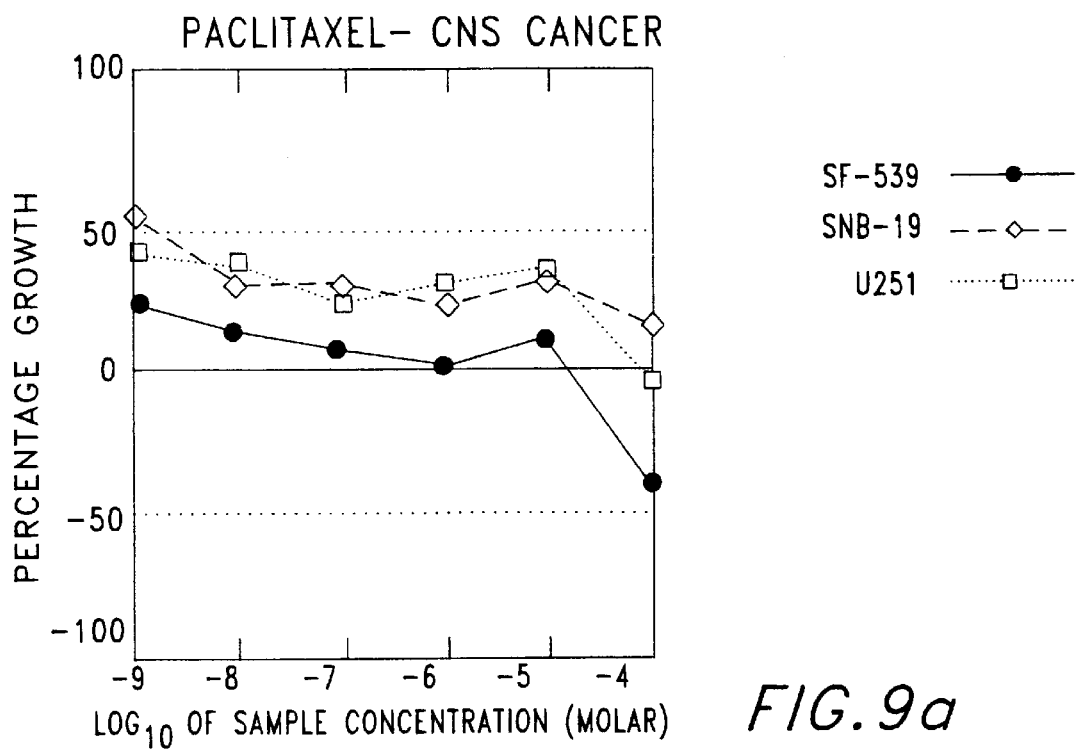

FIG. 9a depicts the dose response curves generated by exposing various CNS cancer cell lines to various concentrations of paclitaxel.

Figure 9B:
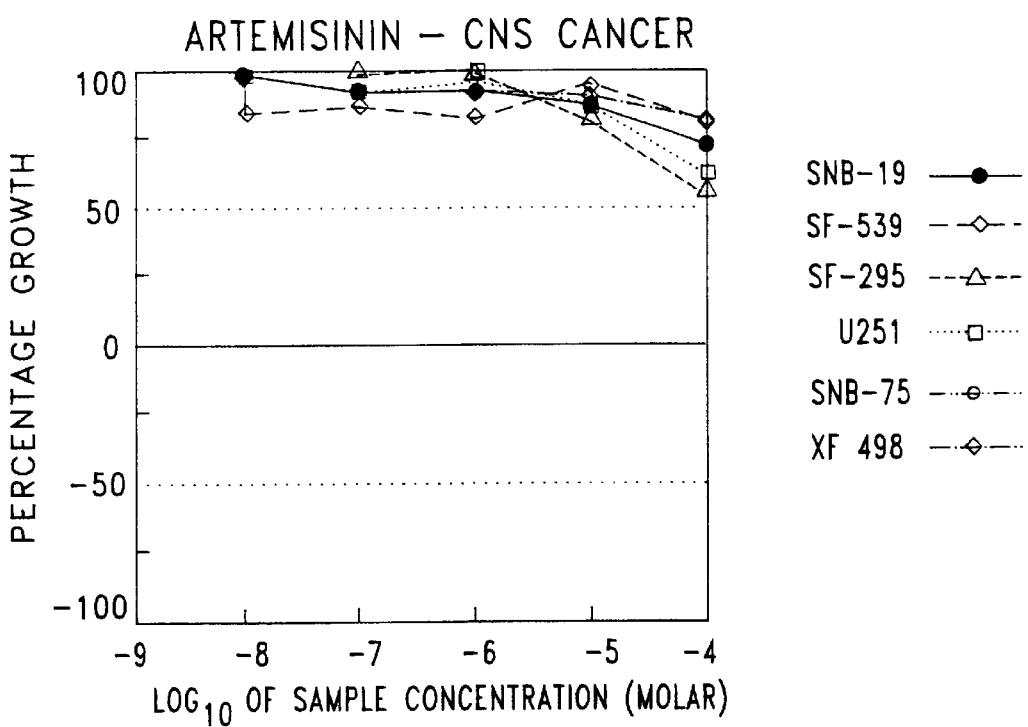

FIG. 9b depicts the dose response curves generated by exposing various CNS cancer cell lines to various concentrations of artemisinin.

Figure 9C:
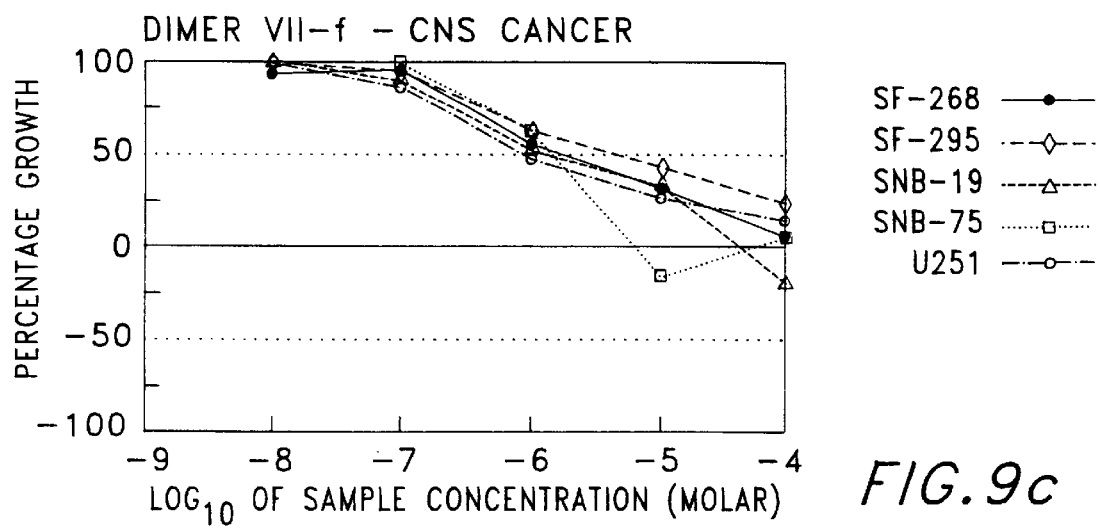

FIG. 9c depicts the dose response curves generated by exposing various CNS cancer cell lines to various concentrations of the C-10 carbon-substituted dimer VII-f of the present invention.

Figure 9D:
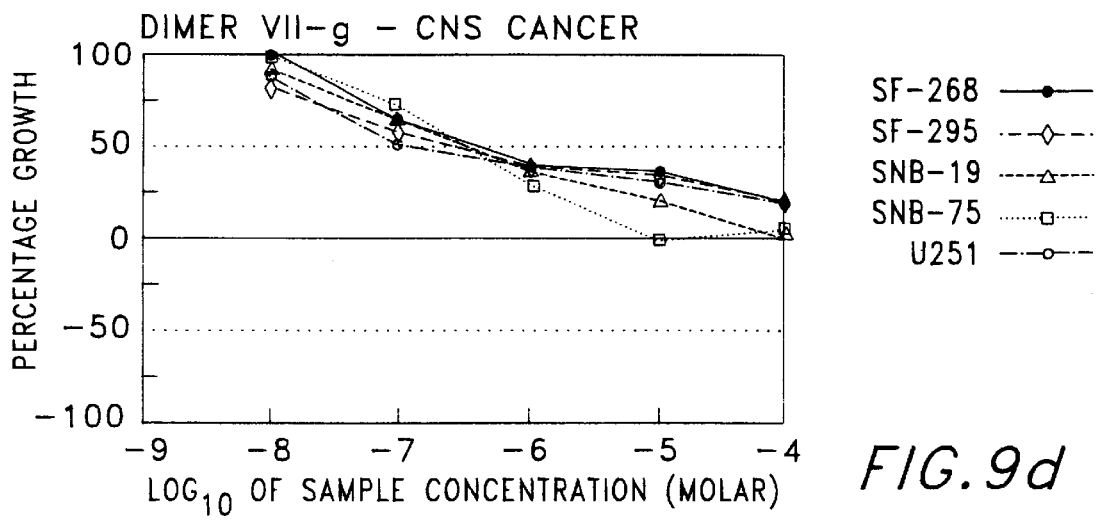

FIG. 9d depicts the dose response curves generated by exposing various CNS cancer cell lines to various concentrations of the C-10 carbon-substituted dimer VII-g of the present invention.

Figure 9E:
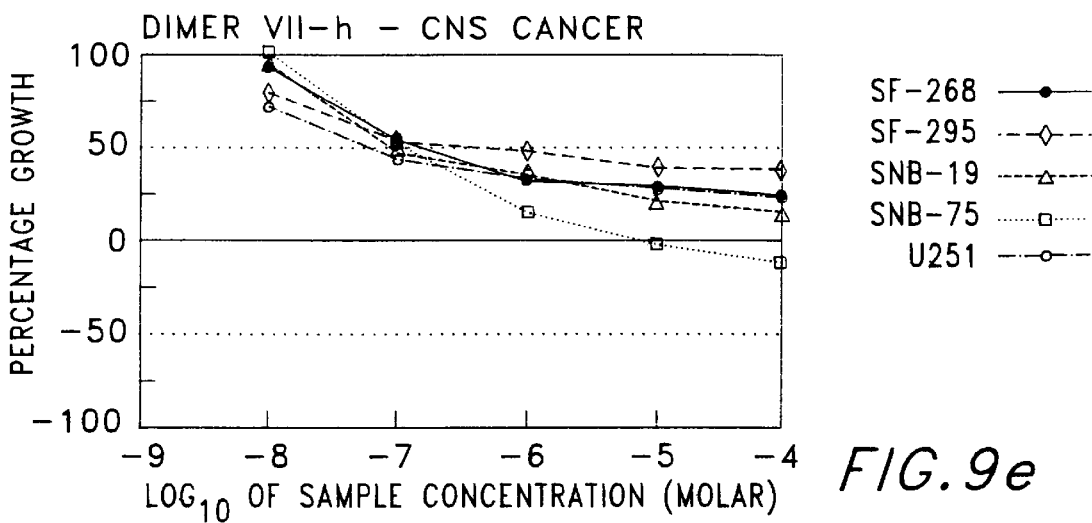

FIG. 9e depicts the dose response curves generated by exposing various CNS cancer cell lines to various concentrations of the C-10 carbon-substituted dimer VII-h.

Figure 10A:
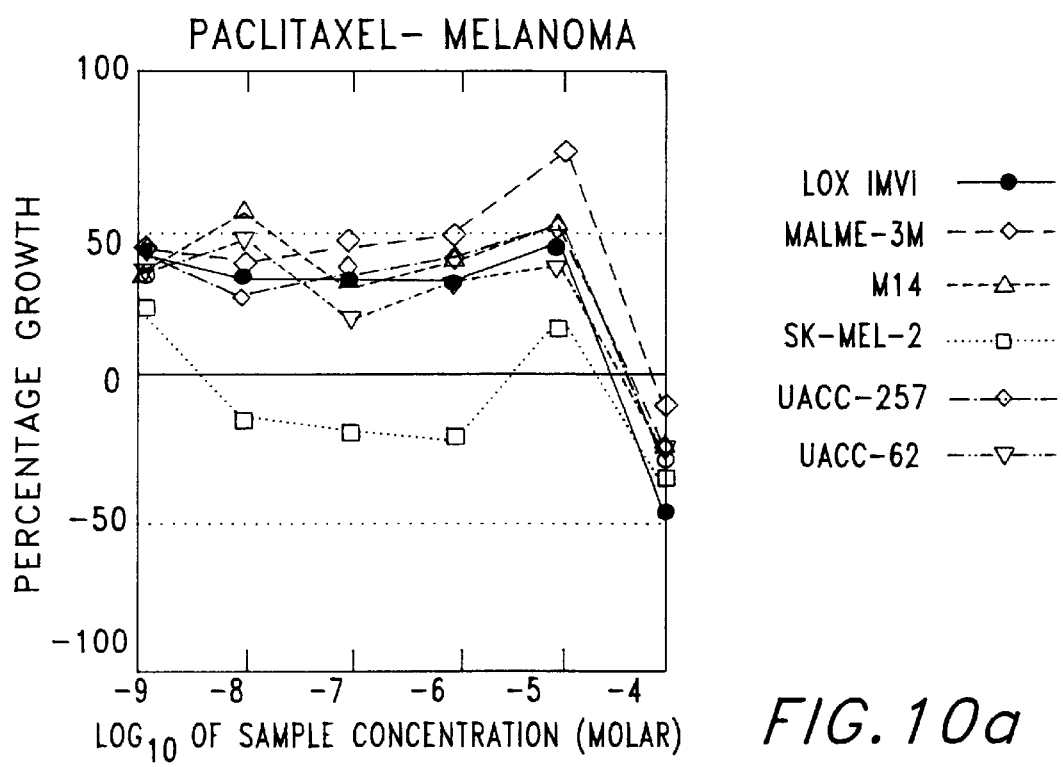

FIG. 10a depicts the dose response curves generated by exposing various melanoma cancer cell lines to various concentrations of paclitaxel.

Figure 10B:
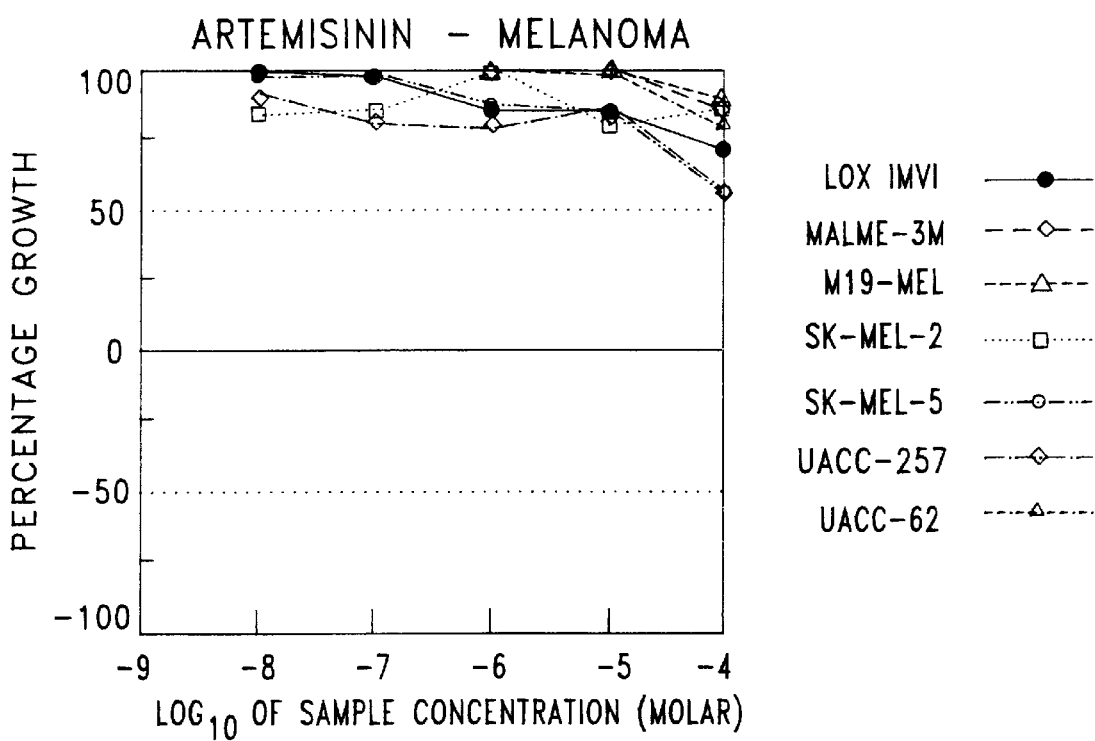

FIG. 10b depicts the dose response curves generated by exposing various melanoma cancer cell lines to various concentrations of artemisinin.

Figure 10C:
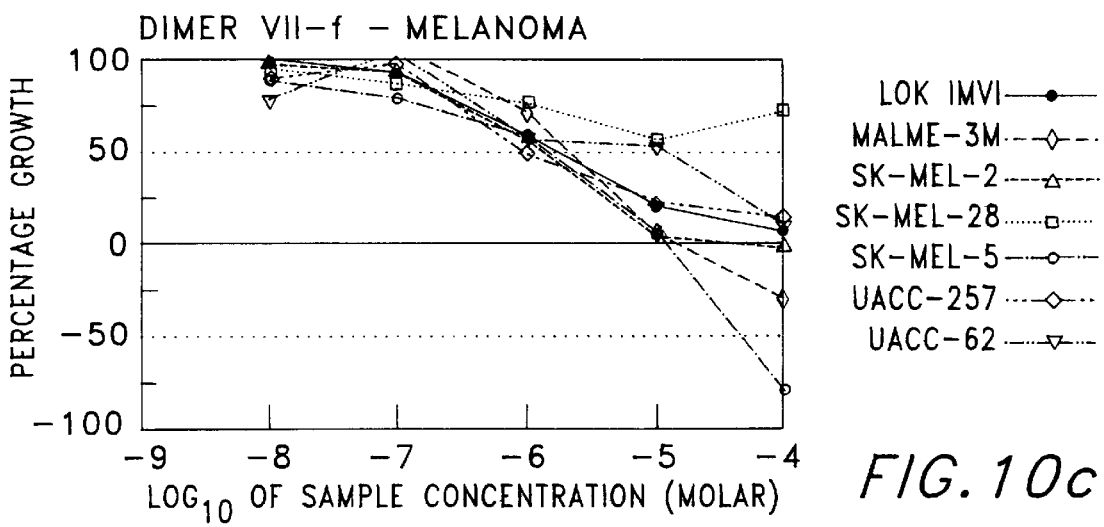

FIG. 10c depicts the dose response curves generated by exposing various melanoma cancer cell lines to various concentrations of the C-10 carbon-substituted dimer VII-f of the present invention.

Figure 10D:
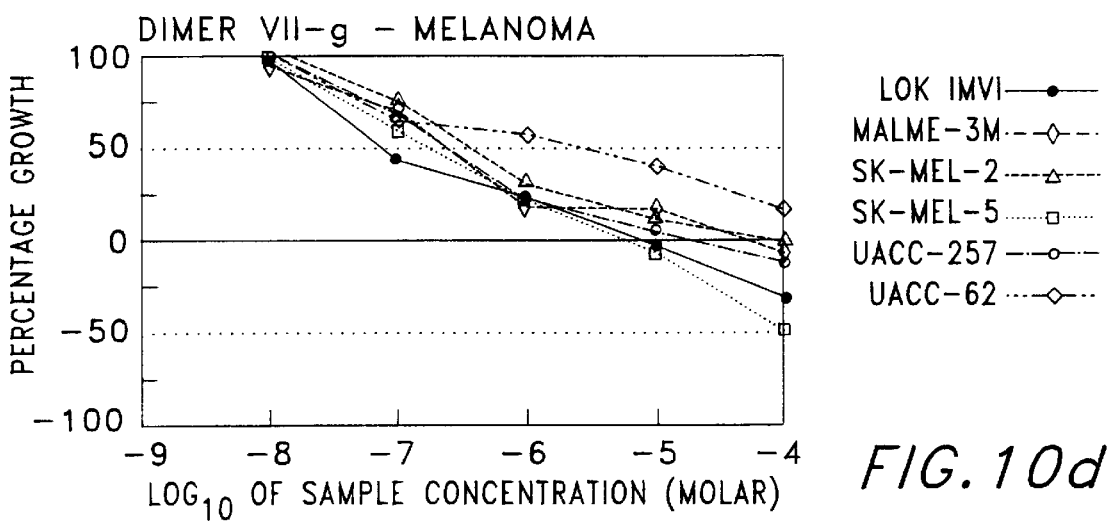

FIG. 10d depicts the dose response curves generated by exposing various melanoma cancer cell lines to various concentrations of the C-10 carbon-substituted dimer VII-g of the present invention.

Figure 10E:
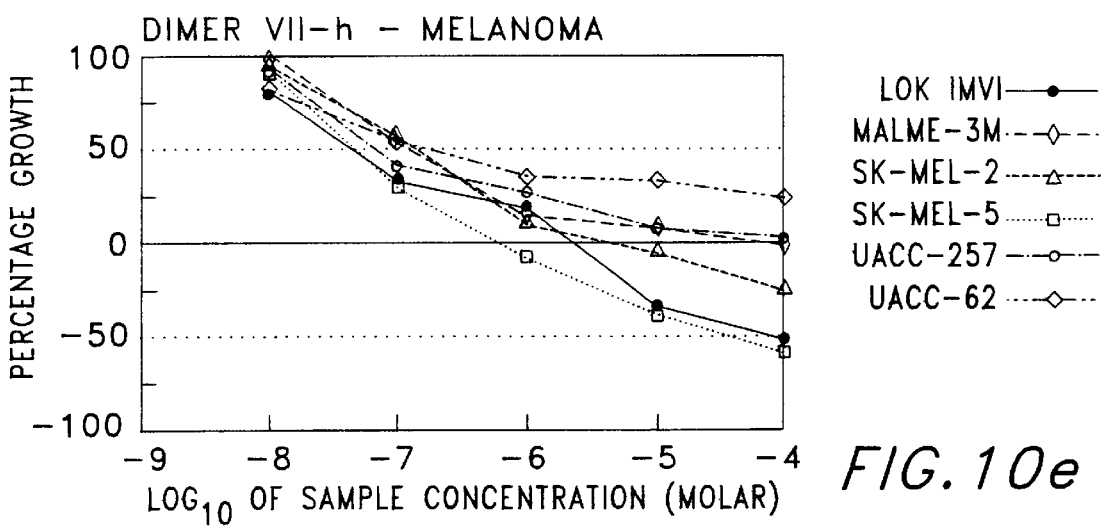

FIG. 10e depicts the dose response curves generated by exposing various melanoma cancer cell lines to various concentrations of the C-10 carbon-substituted dimer VII-h.

Figure 11A:
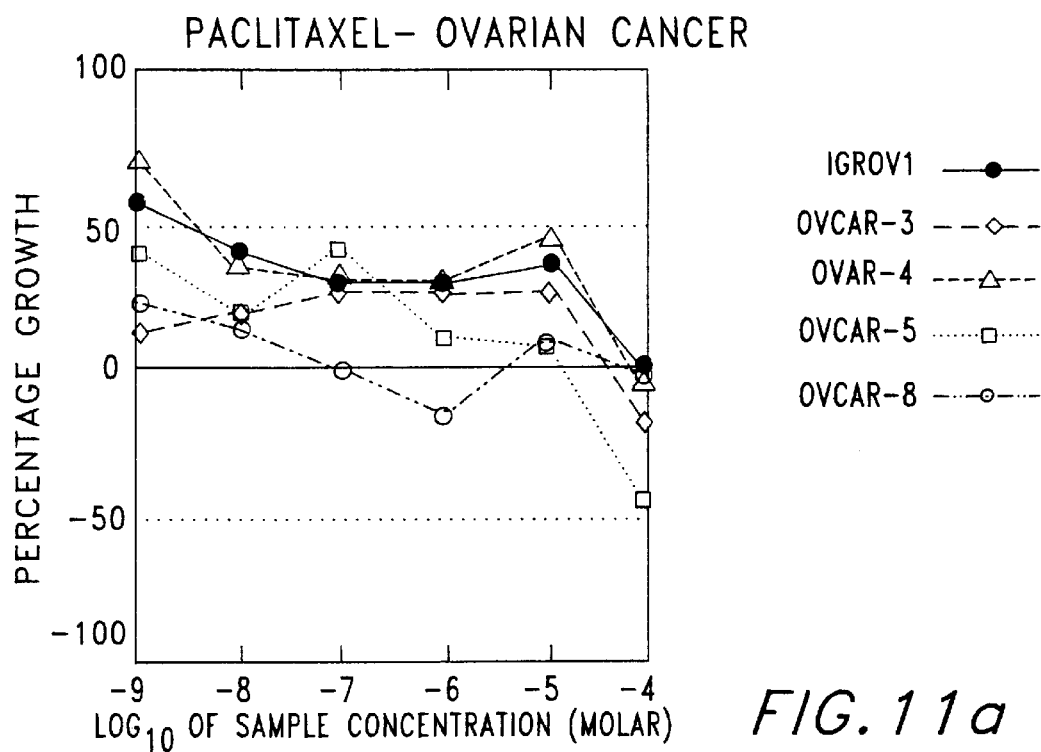

FIG. 11a depicts the dose response curves generated by exposing various ovarian cancer cell lines to various concentrations of paclitaxel.

Figure 11B:
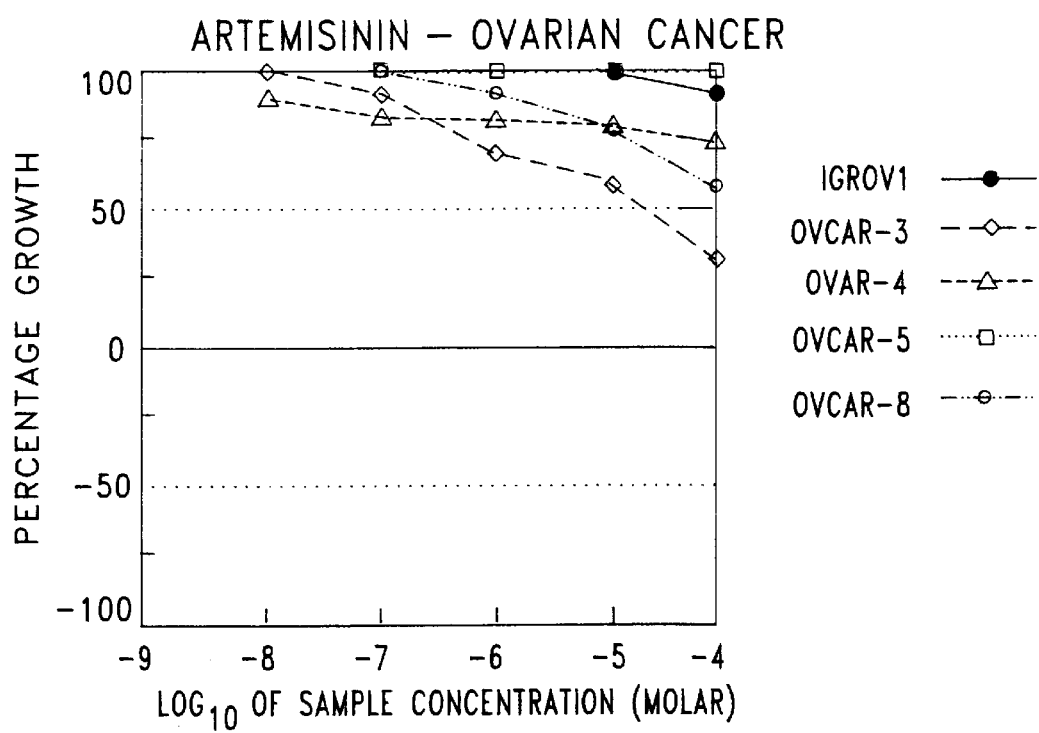

FIG. 11b depicts the dose response curves generated by exposing various ovarian cancer cell lines to various concentrations of artemisinin.

Figure 11C:
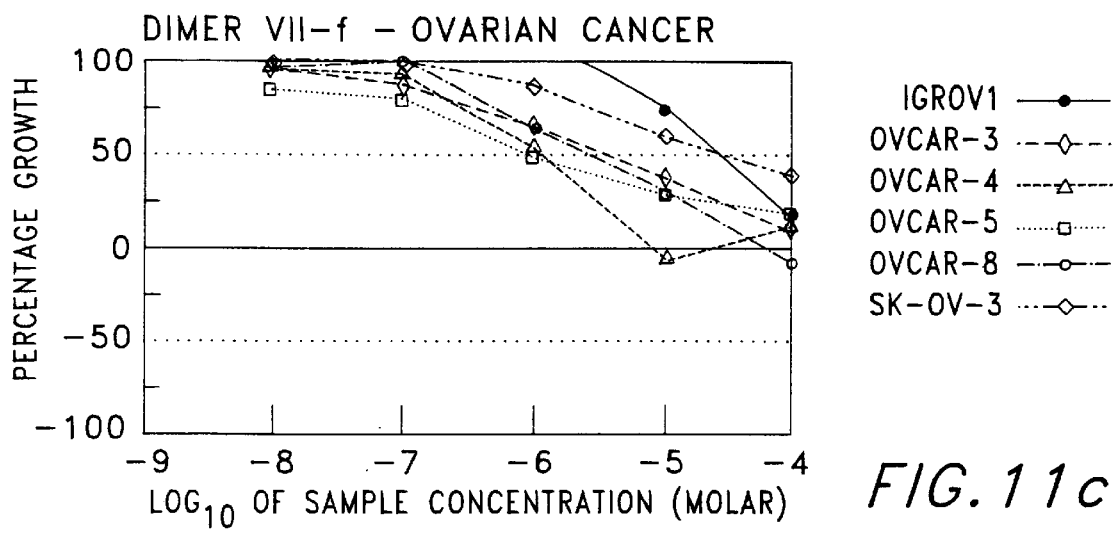

FIG. 11c depicts the dose response curves generated by exposing various ovarian cancer cell lines to various concentrations of the C-10 carbon-substituted dimer VII-f of the present invention.

Figure 11D:
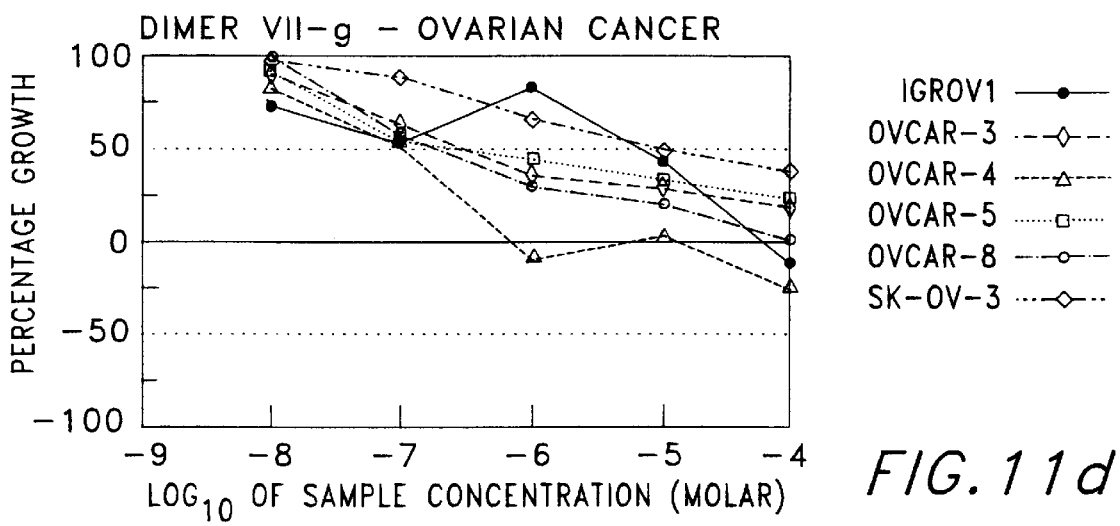

FIG. 11d depicts the dose response curves generated by exposing various ovarian cancer cell lines to various concentrations of the C-10 carbon-substituted dimer VII-g of the present invention.

Figure 11E:
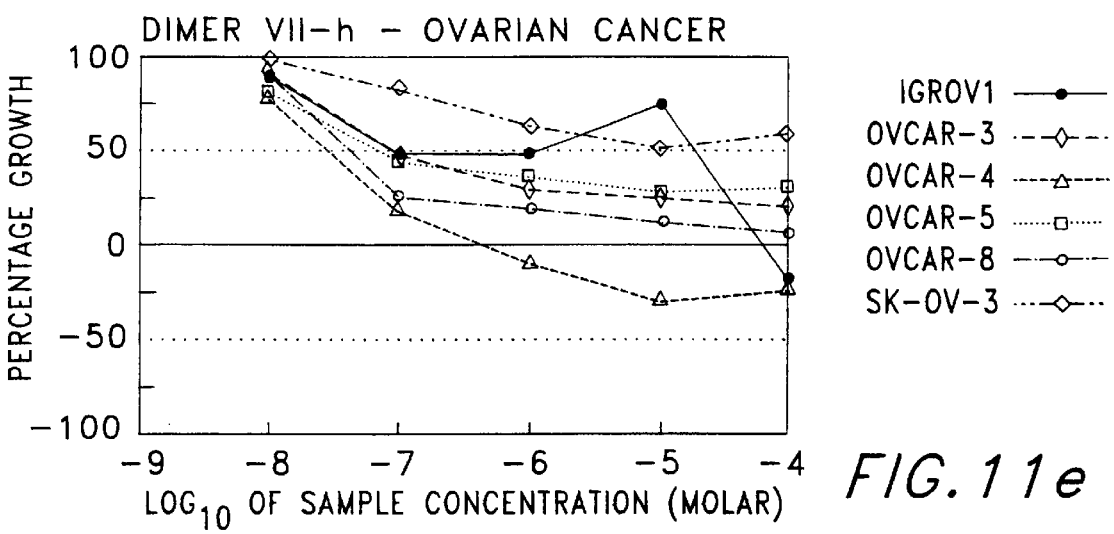

FIG. 11e depicts the dose response curves generated by exposing various ovarian cancer cell lines to various concentrations of the C-10 carbon-substituted dimer VII-H.

Figure 12A:
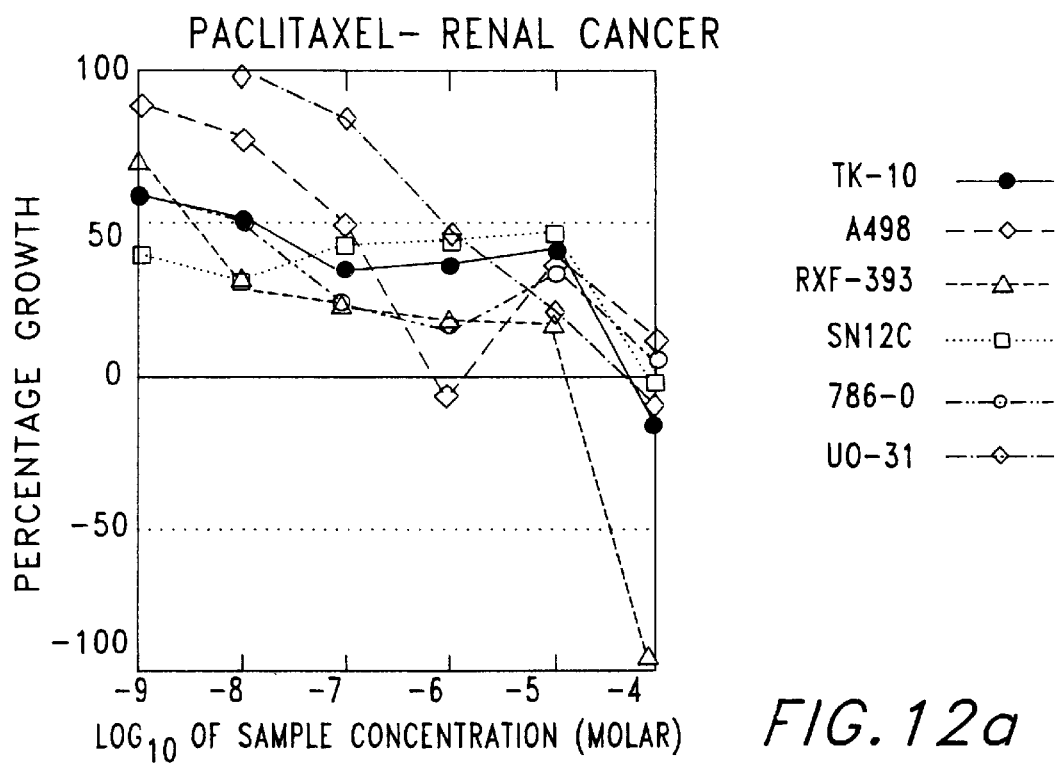

FIG. 12a depicts the dose response curves generated by exposing various renal cancer cell lines to various concentrations of paclitaxel.

Figure 12B:
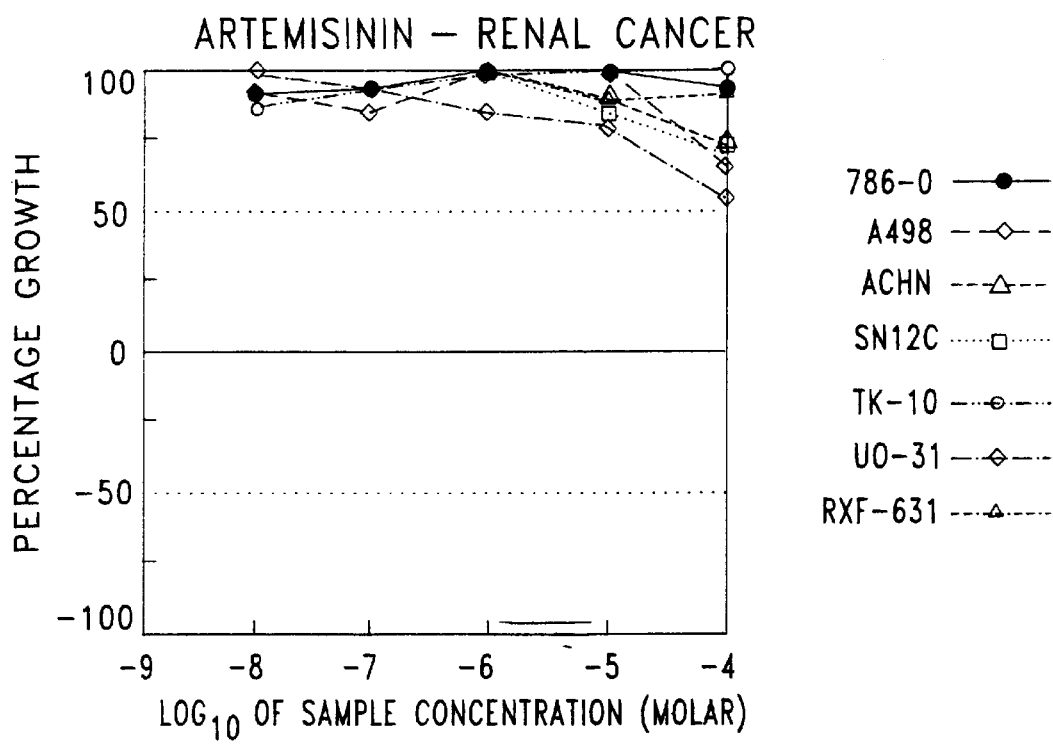

FIG. 12b depicts the dose response curves generated by exposing various renal cancer cell lines to various concentrations of artemisinin.

Figure 12C:
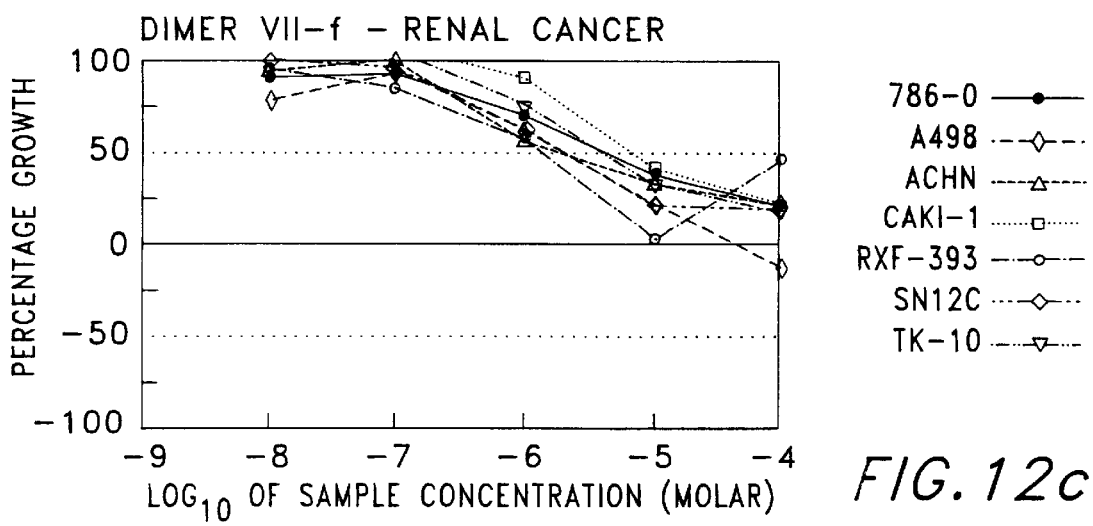

FIG. 12c depicts the dose response curves generated by exposing various renal cancer cell lines to various concentrations of the C-10 carbon-substituted dimer VII-f of the present invention.

Figure 12D:
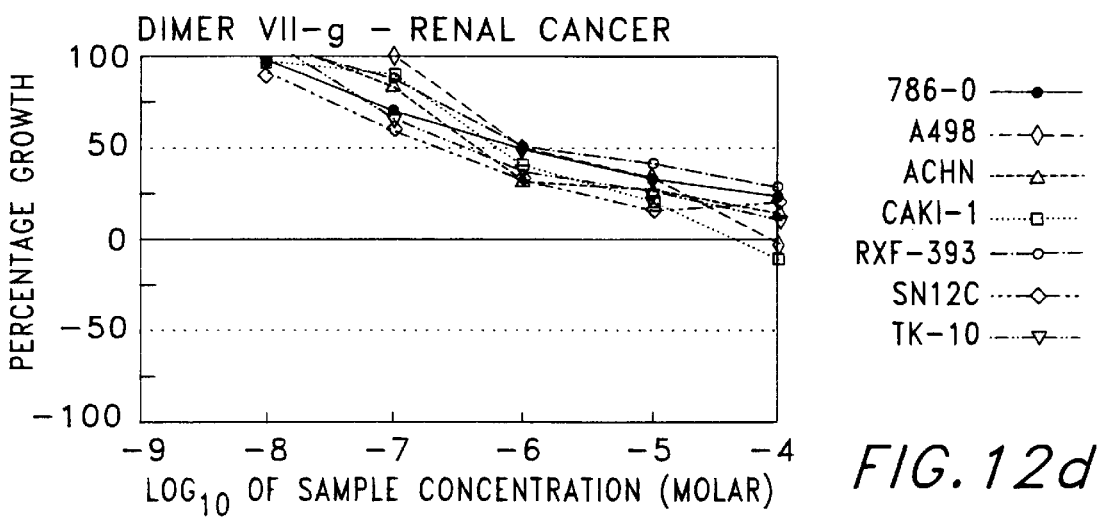

FIG. 12d depicts the dose response curves generated by exposing various renal cancer cell lines to various concentrations of the C-10 carbon-substituted dimer VII-g of the present invention.

Figure 12E:
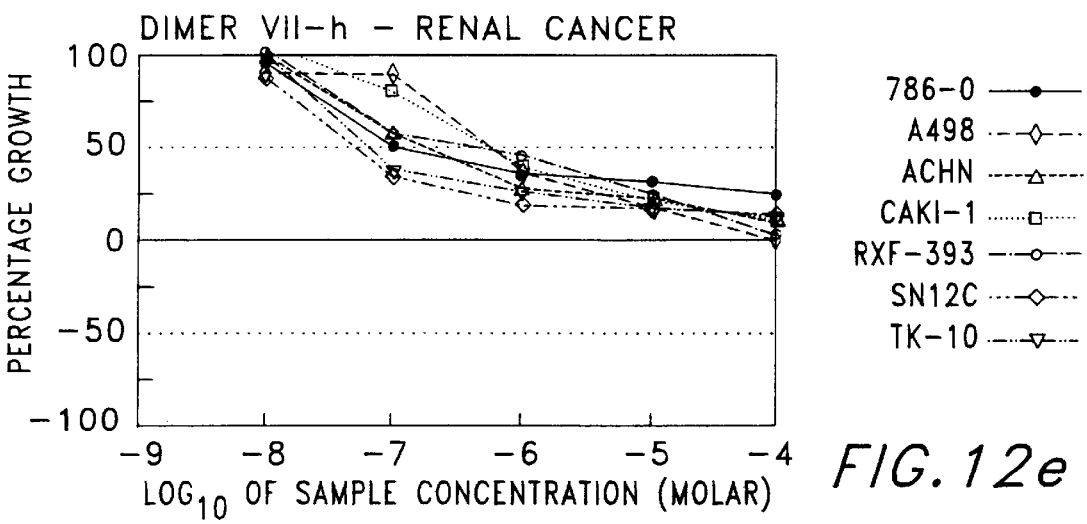

FIG. 12e depicts the dose response curves generated by exposing various renal cancer cell lines to various concentrations of the C-10 carbon-substituted dimer VII-h.

Figure 13A:
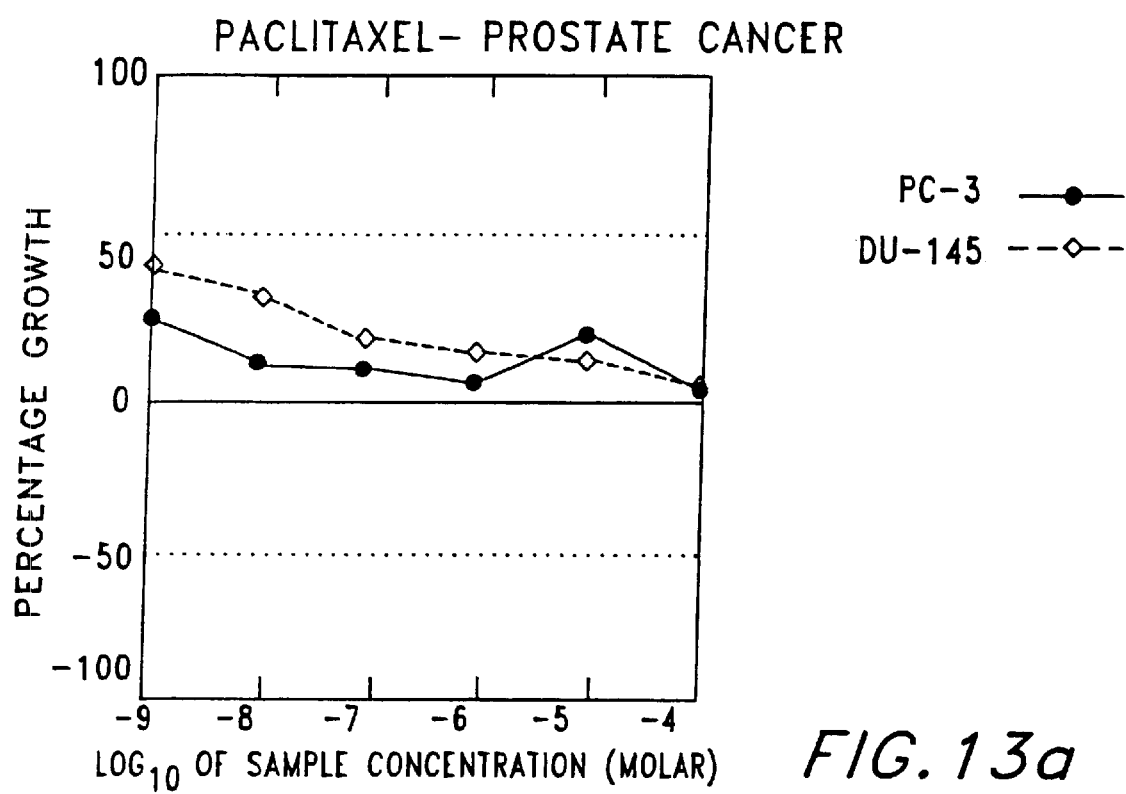

FIG. 13a depicts the dose response curves generated by exposing various prostate cancer cell lines to various concentrations of paclitaxel.

Figure 13B:
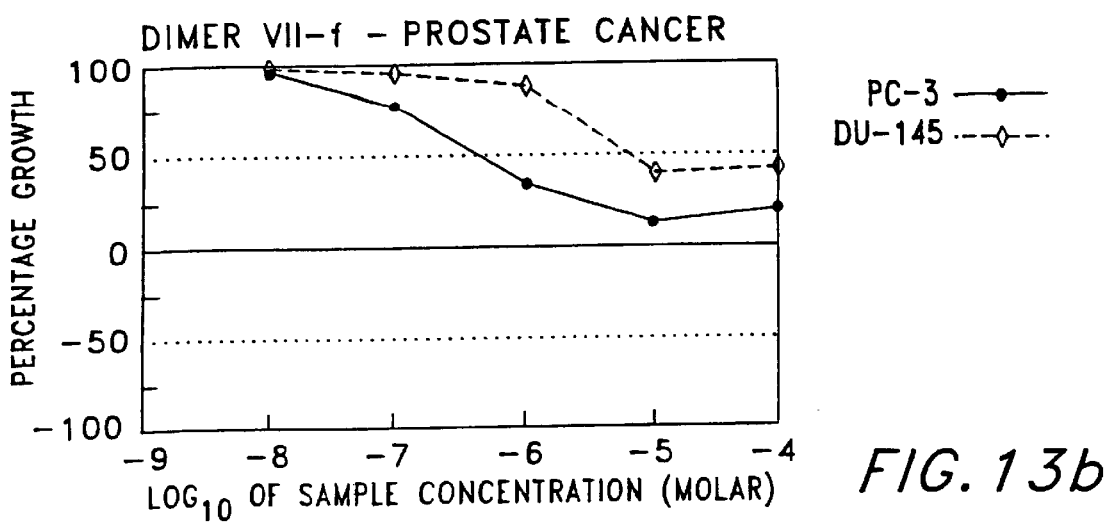

FIG. 13b depicts the dose response curves generated by exposing various prostate cancer cell lines to various concentrations of the C-10 carbon-substituted dimer VII-f of the present invention.

Figure 13C:
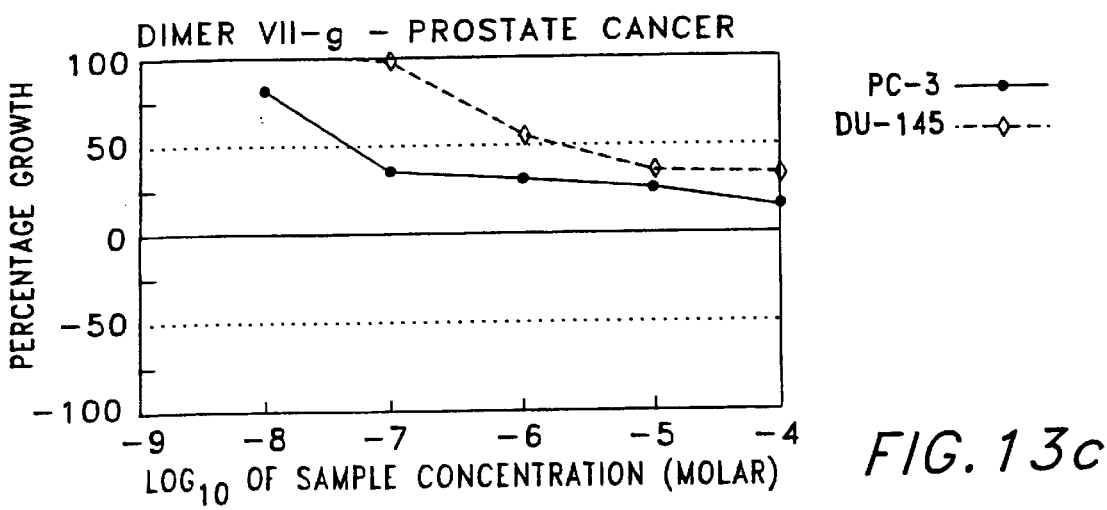

FIG. 13c depicts the dose response curves generated by exposing various prostate cancer cell lines to various concentrations of the C-10 carbon-substituted dimer VII-g of the present invention.

Figure 13D:
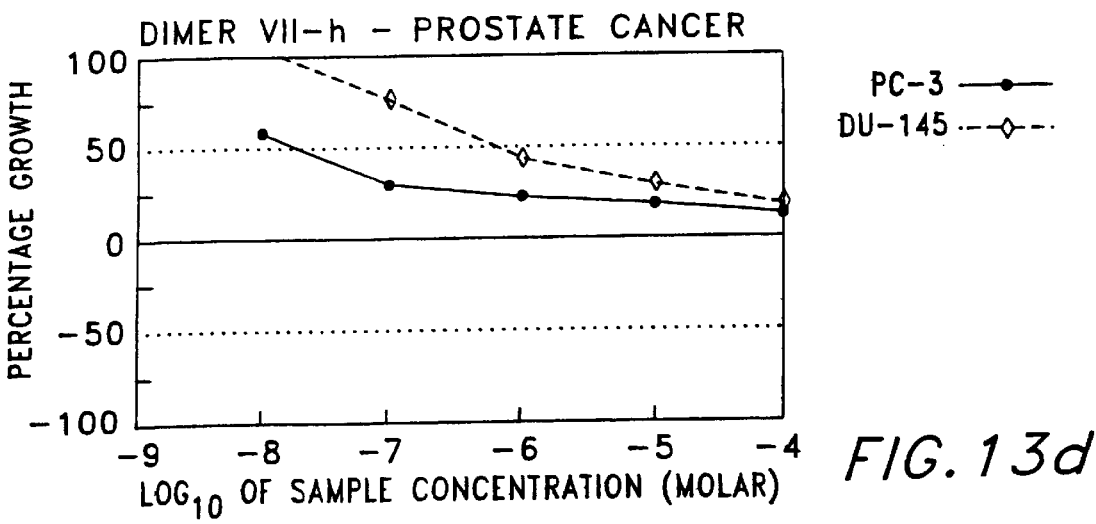

FIG. 13d depicts the dose response curves generated by exposing various prostate cancer cell lines to various concentrations of the C-10 carbon-substituted dimer VII-h.

Figure 14A:
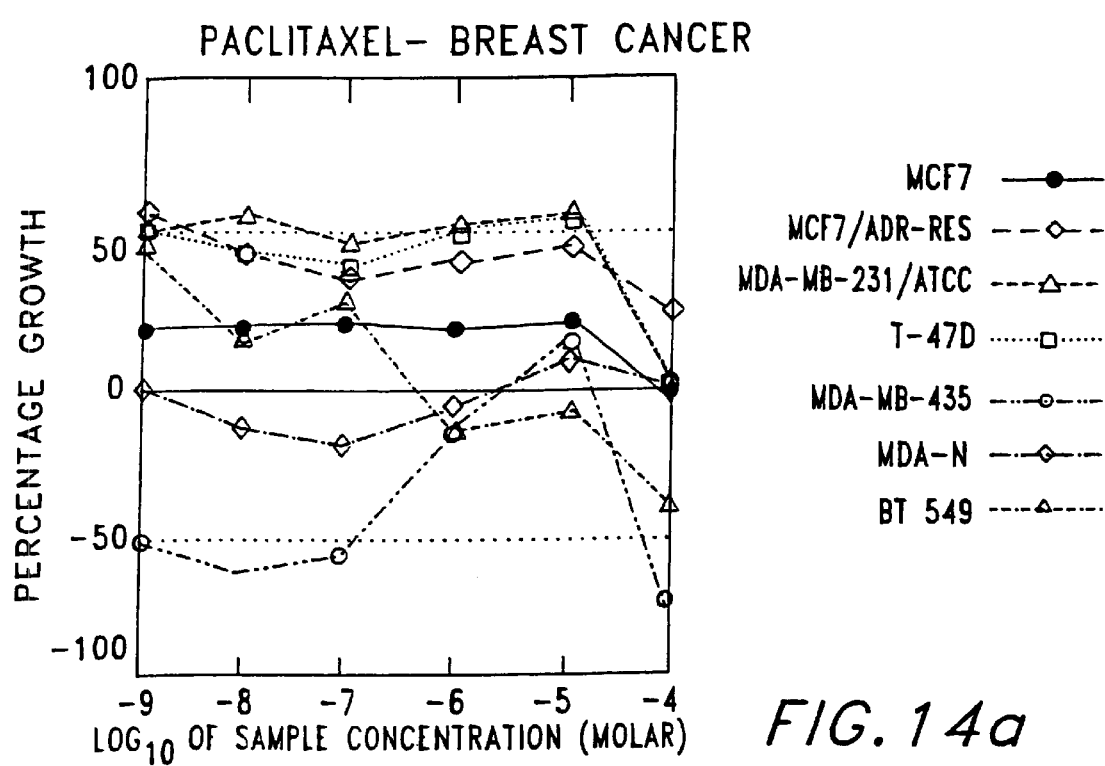

FIG. 14a depicts the dose response curves generated by exposing various breast cancer cell lines to various concentrations of paclitaxel.

Figure 14B:
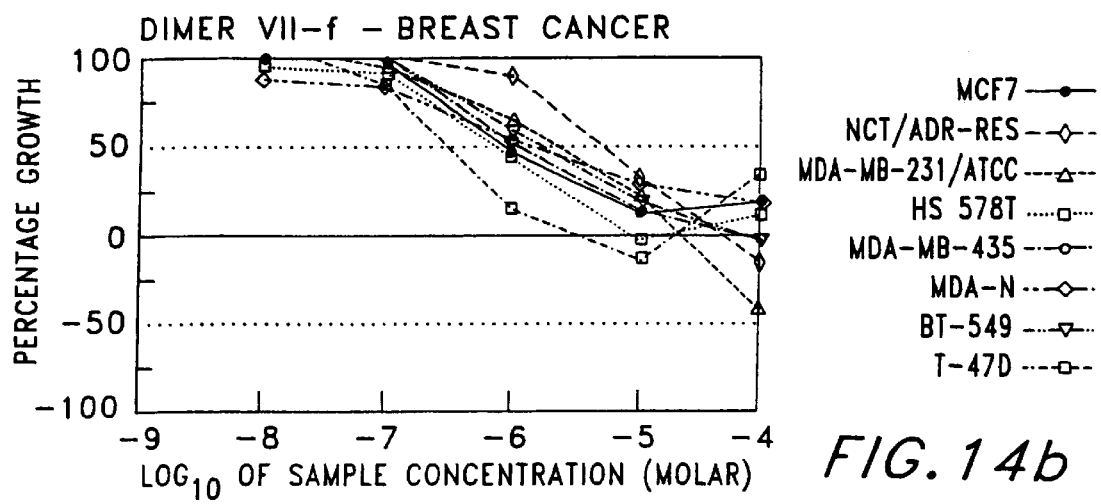

FIG. 14b depicts the dose response curves generated by exposing various breast cancer cell lines to various concentrations of the C-10 carbon-substituted dimer VII-f of the present invention.

Figure 14C:
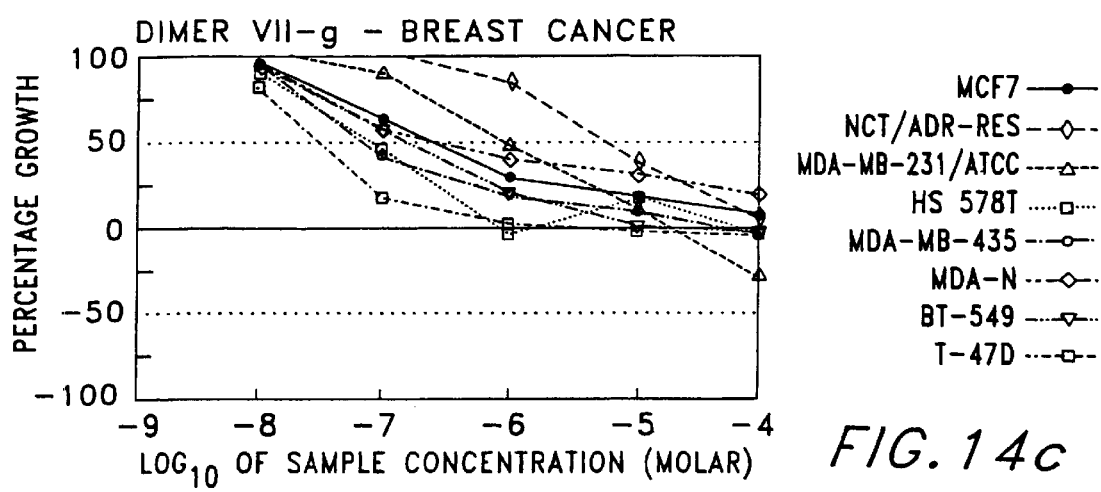

FIG. 14c depicts the dose response curves generated by exposing various breast cancer cell lines to various concentrations of the C-10 carbon-substituted dimer VII-g of the present invention.

Figure 14D:
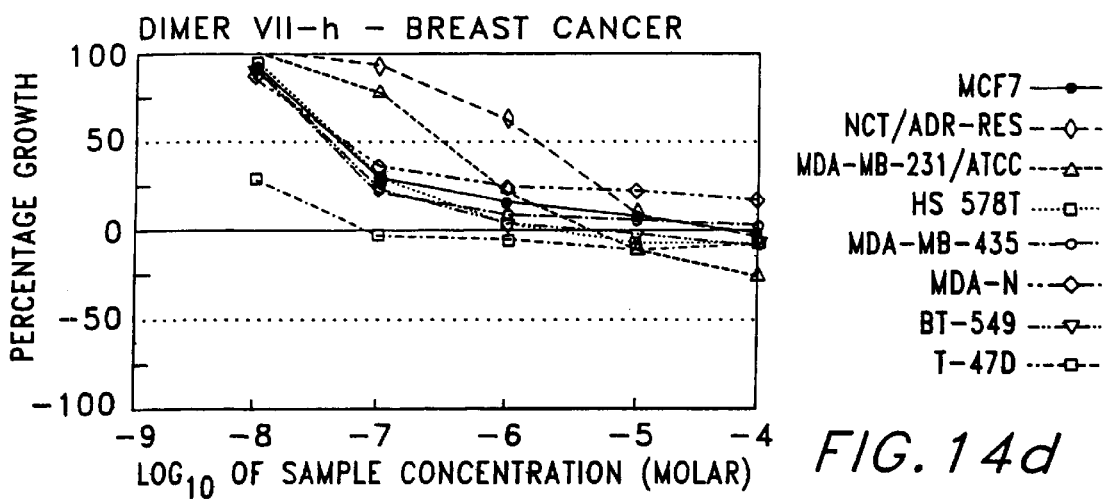

FIG. 14d depicts the dose response curves generated by exposing various breast cancer cell 15 lines to various concentrations of the C-10 carbon-substituted dimer VII-h.

DETAILED DESCRIPTION OF THE PREFERRED EMBODIMENT

The present invention provides a direct method for reacting an organometallic reagent that chemoselectively adds to the lactone group of trioxane lactone artemisinin (I) without cleaving the trioxane bond. The resulting trioxane aldehyde Ie may then be further reacted with organolithium, Grignard, and phosphorous ylide nucleophiles exclusively via carbonyl addition. Also, a trioxane ketone product may be reacted with phenyllithium via only carbonyl addition. These chemoselective lactone, aldehyde, and ketone carbonyl addition reactions produced a series of new, enantiomerically pure, C-10 non-acetal derivatives of natural trioxane artemisinin having high in vitro antimalarial, antiproliferative and antitumor activities.

In general, the first step of the preferred process of the present invention, conversion of artemisinin (I) into trioxane enal Ie, is accomplished by using an effective amount of an organometallic reagent which chemoselectively reacts at the C-10 position of the artemisinin skeleton without disrupting the O—O bond in this trioxane. Effective organometallic reagents include, but are not limited to, heteraryllitium reagents, and preferably lithiothiazole and lithiobenzothiazole. The relative amounts of the various possible organometallic reagents depends upon the concentration employed and other conditions of the reaction. Various amounts of the organometallic reagent can be employed, but generally it should be present in the range of 1.0 to 1.5 molar equivalents of organometallic reagent per molar equivalent of artemisinin for the reaction to proceed to completion.

Based on the published precedents discussed previously in the background section of the present application, it seemed that it would be very difficult to find any reactive organometallic reagents that would add chemoselectively to the lactone carbonyl group (less electrophilic than an aldehyde) of trioxane lactone artemisinin (I) without also cleaving the trioxane O—O bond. In fact, exposing artemisinin to 1.2 equivalent of phenyllithium in THF at -78 ° C. produced at least three major products (not characterized). However, surprisingly after in situ 0-acetylation, thiazole carbonyl adduct Ia was isolated in 95% yield. See FIG. 1. Mass spectrometry confirmed that the trioxane unit was intact, thereby establishing that this new C—C bond-forming reaction had occurred with very high chemoselectivity at C-10 of the artemisinin skeleton without rupturing the O—O bond in this trioxane. Alternatively, as shown in FIG. 2 a similar chemoselective result was obtained using lithiobenzothiazole as the nucleophile. Interestingly, other heteroaryllithium reagents (e.g. 2-lithiothiophene, 2-lithiobenzoxazole) failed to react with artemisinin under conditions in which lithiothiazole and lithiobenzothiazole did react.

The next step in the production of the novel trioxane enal Ie involves the elimination of acetic acid from the artemisinin thiazole acetate Ia product to form the 9,10 alkene Ib product.

Methods for effecting this elimination are well known in the art. Preferably the artemisinin thiazole acetate Ia product is reacted with triethylsilane and trimethylsilyl triflate (TMS-OTf) to form only the corresponding product 9, 10 alkene Ib. This elimination may also be achieved by treating the artemisinin thiazole acetate Ia product with TMS-OTf over molecular sieves or alternatively (as 10 shown in FIG. 2) this elimination may also be accomplished using triethylsilyl triflate (TES-OTf) over molecular sieves.

Next, the alkene thiazole Ib was N-methylated, reduced, and then hydrolyzed without purification of intermediates following standard procedures well known in the art (see Dondoni, A.; Marra, A.; Perrone, D. J Org. Chem. 1993, 58, 275) incorporated herein by reference, to form 9, 10-unsaturated C-10 aldehyde Ie. The three separate steps shown in FIG. 1 allowed conversion of artemisinin (I) into trioxane 9-en-10-al Ie in 69% overall yield. This addition-elimination sequence overall represents addition of a formyl anion unit at C-10 of artemisinin followed by dehydration.

Demonstration of further high chemoselectivity in organometallic reactions with such artemisinin trioxane analogs was achieved by organometallic nucleophilic addition to the carbonyl group of enal Ie. As shown in FIG. 3, organometallic reagents or Grignard reagents such as, but not limited to n-butyllithium, phenyllithium, and phenyl magnesium bromide, added exclusively (and in some cases stereoselectively) to only the aldehyde carbonyl group of trioxane enal Ie to form allylic alcohols I-1 and I-2, without rupturing the trioxane O—O bond. n-Butyllithium added to enal Ie to give a roughly 2:1 diastereomeric mixture of allylic alcohols I-1. Whereas phenyllithium added to aldehyde Ie to produce a 3.2: 1.0 mixture of allylic alcohol diastereomers I-2, phenylmagnesium bromide formed the same benzylic alcohols I-2 in a 7.6:1.0 ratio, presumably due to magnesium coordination also to one or more of the non-aldelydic oxygen atoms in polyoxygenated aldehyde Ie. When excess phenylmagnesium bromide was used, however, the peroxide O—O bond in trioxane alcohol I-2 underwent nucleophilic rupture. Oxidation of alcohols I-1 and I-2 produced enones I-3 and I-4. This oxidation step can be accomplished using standard procedures such as tetrapropylammonium perruthenate (TPAP) and N-methylmorpholine N-oxide (NMO) disclosed by Ley, S. V.; Norman, J.; Griffith, W. P.; Marsden, S. P. *Synthesis* 1994, 639 and incorporated herein by reference. Phenyl enone I-4 reacted with phenyllithium exclusively via carbonyl addition to form tertiary alcohol trioxane I-5.

Other artemisinin analogues were obtained by converting the aldehyde Ie using standard Wittig reagents to form a mixture of geometric isomers of monomeric or dimeric exocyclic alkenes VII without cleaving the trioxane O—O bond as shown in FIG. 4. The monomeric exocyclic alkenes (VII, where n=1) may be produced by reacting Ie with $RCH=PPh_3$ wherein R is alkyl, cycloalkyl, heteroalkyl, heterocycloalkyl, alkenyl, alkynyl, aryl or heteroaryl. The term "alkyl" includes straight chain or branched alkyl compounds comprising 1–20 carbon atoms and cyclic alkyl compounds comprising 5–10 carbon atoms. The term "heteroalkyl" includes polyalkylene glycols such as polyethylene glycol (PEG). The term "aryl" means a phenyl or phenyl group substituted by 1 or more substituents selected from the group comprising halogen, nitro, amino, hydroxy, thiohydroxy, lower alkoxy, lower thioalkyl, lower alkyl, $NHC(=O)R_1$ wherein $R_1$ is aryl or lower alkyl, COOH, or $COOR_2$ wherein $R_2$ is aryl or lower alkyl. The term "heteroaryl" includes 5 or 6 membered heteroaromatic rings comprising one or more heteroatoms selected from N, O or S, unsubstituted or substituted by halogen, nitro, amino, hydroxy, thiohydroxy, lower alkoxy, lower alkyl, NHC $(=O)R_1$ wherein $R_1$ is aryl or lower alkyl, COOH, or $COOR_2$ wherein $R_2$ is aryl or lower alkyl. The term "lower alkyl" means straight or branched hydrocarbon radicals comprising 1–20 carbon atoms and include, for example, methyl, ethyl, n-propyl, isopropyl, n-butyl, t-butyl, n-pentyl and the like. "Halogen" is fluorine, chlorine, bromine or iodine.

The dimeric artemisinin analogues may be produced by reacting Ie with $PPh_3=CH—R—CH=PPh_3$ where R is a linker group including, but not limited to, alkyl, cycloalkyl, heteroalkyl, heterocycloalkyl, alkenyl, alkynyl, aryl or heteroaryl. The term "alkyl" includes bivalent straight chain or branched alkyl compounds comprising 1–20 carbon atoms and cyclic alkyl compounds comprising 5–10 carbon atoms. The term "heteroalkyl" includes bivalent polyalkylene glycols such as polyethylene glycol (PEG). The term "aryl" means a bivalent phenyl or phenyl group substituted by one or more substituents selected from the group comprising halogen, nitro, amino, hydroxy, thiohydroxy, lower alkoxy, lower thioalkyl, lower alkyl, NHC(=O)$R_1$ wherein $R_1$ is aryl or lower alkyl COOH, or COO$R_2$ wherein $R_2$ is aryl or lower alkyl. The term "heteroaryl" includes bivalent 5 or 6 membered heteroaromatic rings comprising one or more heteroatoms selected from N, O or S, unsubstituted or substituted by halogen, nitro, amino, hydroxy, thiohydroxy, lower alkoxy, lower alkyl, NHC(=O)$R_1$ wherein $R_1$ is aryl or lower alkyl, COOH, or COO$R_2$ wherein $R_2$ is aryl or lower alkyl. The term "lower alkyl" means straight or branched hydrocarbon radicals comprising 1–20 carbon atoms and include, for example, methyl, ethyl, n-propyl, isopropyl, n-butyl, t-butyl, n-pentyl and the like. "Halogen" is fluorine, chlorine, bromine or iodine.

The Z-and E-geometric isomers of these monomeric and dimenic exocyclic alkenes VIIa-h were separated from each other chromatographically. In the case of VII-e, only the more soluble major isomer Z-VII-e remained in solution when a 1:1 mixture of the two isomers selectively precipitated out of solution from ethyl acetate/hexane solvent. Assignment of exocyclic alkene geometry was achieved reliably by $^1$H NMR spectroscopy with the E-isomers having considerably larger vicinal H-H coupling constants than those of the corresponding Z-isomers.

Determination of Antimalarial Activity

To determine the antimalarial effect of various C-10 carbon-substituted monomers of the present invention, screening assays were performed against chloroquine-sensitive *P. falciparum* (NF54), according to the method described below their $IC_{50}$ values are included in Table 1. Strikingly, seven of the eleven C-10 trioxane analogs are at least as potent as artemisinin. The most potent of these analogs is I-3, with an $IC_{50}$ of 1.4 nM relative to artemisinin's $IC_{50}$ of 10 nM.

Activity was determined by measuring the incorporation of [$^3$H]hypoxanthine, by the methods of Desjardins and Milhouse, with the following modifications, see Desjardins, R. E.; Canfield, C. J.; Haynes, J. D.; Chulay, J. D. *Antimicrob. Agents Chemother.*, 16: 710 (1979); Milhous, W. K.; Weatherly, N. F.; Bowdre, J. H.; Desjardins, R.; *Antimicrob. Agents Chemother.*, 27: 525 (1985). Chloroquine-sensitive *P. falciparum* (NF54 strain) were maintained in a 2.4% suspension of type O$^+$ human erythrocytes (obtained weekly from a rotating pool of screened healthy volunteers) in RPMI 1640 (Gibco BRL # 13200-076), supplemented with 25 mM N-2-hydroxyethylpiperazine-N-2-ethanesulfonic acid (HEPES; Calbiochem #391338), 27 mM NaHCO$_3$ (Gibco BRL # 11810-025), and 10% heat-inactivated human type O$^+$ serum (Interstate Blood Bank, Inc.), under 3% O$_2$, 4% CO$_2$, and 93% N$_2$-Parasitemia was maintained at 0.05–3% and doubling time at approximately 15 hours by twice weekly change of medium and replenishment with fresh erythrocytes.

Stock solutions (approximately 2.5 mg/mL of HPLC-purified or recrystallized test compound) were prepared in dimethyl sulfoxide (DMSO; Sigma-Aldrich #27,043-1). DMSO solutions were diluted 500-fold in medium, serially diluted in 0.2% DMSO in medium (to maintain constant solvent concentration), then 100 µL aliquots were pipetted into microtiter plate wells (Costar3595). Provisional $EC_{50}$ values were obtained in a survey of seven 5-fold dilutions yielding final concentrations (in triplicate) of 0.16–2500 ng/mL. Assays were Ia ter expanded to include ten concentrations (in quadruplicate) of approximately 1.8-fold dilutions which flank the provisional $EC_{50}$. Plates included at least 8 wells of no drug controls (4 with and 4 without DMSO) and 4 wells of uninfected erythrocytes. Parasite culture (0.25% parasitemia in 2.4% hematocrit; 100 µL per well) was added and the plate was incubated for 48 hours prior to the addition of 25 µL [$^3$H]hypoxanthine (14.1 Ci/mmol, 1 mCi/mL in 70% ethanol, New England Nuclear NET-177, diluted to 25 µCi/mL with medium) and subsequent 20 hour incubation. Cells were harvested (Brandel MB-48R) onto GF-C glass filters (Brandel). The filters were washed five times with 3 mL water per sample spot, dried under a heat Ia mp, and counted (Beckman Model LS-6500) in scintillation cocktail (ICN Cytoscint).

Decays per minute (dpm) values were downloaded and analyzed (Power Macintosh 7200/90; Microsoft Excel 5.0), to yield the mean and standard deviation at each drug concentration. Dose-response curves were fit to the experimental data (Delta Point DeltaGraph 3.5.3) by means of the Marquardt algorithm, were solved for the drug concentration that kills 50% of parasites, and were analyzed for goodness of fit (R value).

TABLE I

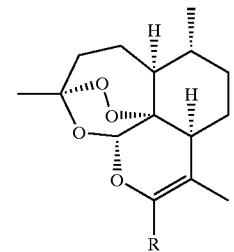

| C 10-trioxane | R | $IC_{50}$ (nM)* |
| --- | --- | --- |
| Ib | 2'-thiazolyl | 14 |
| Benzo-4 | 2'-benzothiazolyl | 7.8 |
| Ie | CHO | 37 |
| I-3 | C(O)n-Bu | 4.3 |
| I-4 | C(O)Ph | 4.6 |
| I-5 | C(OH)Ph$_2$ | 4.5 |
| VII-a | CH=CH$_2$ | 28 |
| E-VII-c | E-CH=CHPH | 16 |
| Z-VII-C | Z-CH=CHPH | 8.1 |
| E-VII-d | E-CH=CHPhNO$_2$-p | 11 |
| Z-VII-d | Z-CH=CHPhNO$_2$-p | 10 |
| Artemisinin | | 10.1 ρ 1.3 |

*Antimalarial activity against *Plasmodium falciparum* was determined as reported previously. The standard deviation for each set of quadruplicates was an average of 9.8% (32%) of the mean. $R^2$ values for the fitted curves were: ≦0.990. Artemisinin is ± standard deviation of concurrent control (n = 11).

Antimalarial testing in vitro against *Plasmodium falciparum* NF54 malaria parasites, according to the procedure discussed above showed that C-9,10-unsaturated, C-10 carbon-substituted heteroaryl artemisinin analogs Ib and benzo-4, ketones I-3 and I-4, tertiary alcohol I-5 and exocyclic alkenes VII-a,-c, and -d, are all similar to clinically used natural artemisinin (I) in antimalarial potency (Table 1). The high antimalarial activities of these C-10 carbon-substituted artemisinin analogs in Table 1 provide biological evidence that the trioxane O—O bond in these semi-synthetic analogs is intact; artemisinin derivatives lacking this O—O linkage are not antimalarially active. Several of the C-10 derivatives in Table 1 as well as other analogs available easily via this new synthetic methodology may have especially desirable solubility and pharmacological properties.

Determination of Antiproliferative and Antitumor Activities

To determine the inhibitory effect of the compositions of the present invention on cell proliferation, screening assays were performed on a murine keratinocyte cell line PE. Cell line PE was chosen for its particular sensitivity to the induction of omithine decarboxylase (ODC) activity by the extensively characterized tumor promoter TPA. Cell line PE was derived from a papilloma-induced in female SENCAR mice by a standard skin initiation/promotion protocol, see Yuspa, S. H., et al., *Carcinogenesis*, 7:949–958 (1986). PE cell culture medium consisted of Eagle's minimal essential medium without calcium chloride (Whittaker Bioproducts, Walkersville, Mass.) supplemented with 8% chelexed fetal calf serum and 1% antibiotic-antimycotic (Gibco BRL) and the addition of $CaCl_2$ to 0.05 mM $Ca^{++}$.

MTT [3-(4,5-dimethylthiazol-2-yl)-2,5-diphenyltetraxolium bromide] was purchased from Sigma Chemical Co. (St. Louis, Mo.), and TPA was supplied by L.C. Services (Woburn, Mass.). L-[$^{14}$C]ornithine (56 [$\mu$Ci/mol) was from Amersham/Searle Corp. (Arlington Heights, Ill.). Chemical solvents used in all assays of biological activity were of the highest grade commercially available.

Growth Inhibition. Growth curves, shown in FIG. 5, for PE cells treated with calcitriol and the C-10 carbon-substituted dimers VII-f, VII-g and VII-b generated by assay for the reduction of the tetrazolium-based compound MTT, see Charmichael, et al., *Cancer Res.*, 47:936–942 (1987). A mitochondrial dehydrogenase reduces MTT to a blue formazan product with an absorbance maximum of 505 nm in DMSO; the number of viable cells can thus be determined spectrophotometrically. PE cells were seeded at a density of 5,000 cells/well in 50 $\mu$L of medium into 96-well microtiter plates. Twelve hours later, the medium was removed, and cells were treated with 100 $\mu$L of fresh medium into which the appropriate amount of calcitriol or analog dissolved in dimethyl sulfoxide (DMSO) had been added, with the concentration of DMSO held constant at 0.1%. The plates were fed once at 48 hours, with the readdition of the C-10 carbon-substituted trioxane dimers VII-f, VII-g and VII-h at this time. At 24-hour intervals following the initial treatment of the cells with compounds, 0.1 mg (50 $\mu$L of a 2 mg/mL solution) of MTT was added to each well. After 4 hours, the MTT was removed and DMSO added to dissolve the blue formazan dye. Using a microtiter plate reader, the $A_{505}$ was then determined and cell number calculated from blank-subtracted absorbance values. Results from the MTT assay for the inhibition of cell growth were independently confirmed by treating 100-cm$^2$ dishes of cells in an analogous manner for 96 hours, whereupon the cells were harvested by trypsinization and counted. Further, the viability of the cells treated with calcitriol or trioxane dimers was determined to be identical to control cells at 96 hours by trypan blue exclusion.

Antiproliferative activities, measured in vitro using murine keratinocytes as described previously, are shown in FIG. 5. Note that the trioxane dimers [VII-f, VII-g and VII-h even at physiologically relevant 100 nanomolar concentrations, are at least as antiproliferative as calcitriol (1$\alpha$, 25-dihydroxyvitamin $D_3$) that is the hormonally active form of vitamin D and that is used clinically as a drug to treat psoriasis, a skin disorder characterized by uncontrolled proliferation of cells.

To determine the cytotoxicity of the C-10 carbon-substituted trioxane dimers VII-f, VII-g and VII-h of the present invention, screening assays were performed by the National Cancer Institute using a 60 cell line panel; some of these activities of trioxane dimers VII-f, VII-g and VII-h are summarized in Tables I, III and IV (set out below). The screening assay is performed on 96-well microtitre plates. Relatively high initial inoculation densities are used, in order to permit measurement of "time-zero" values and to enhance the screen's ability to detect and provide some differentiation between antiproliferative and cytotoxic response parameters. The specific inoculation densities (which range from 5,000 to 40,000 cells/well) used for each cell line are those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar. Higher or lower concentration ranges may be selected on a nonroutine basis if appropriate solubility and/or prior biological information or other screening data so dictate. Duplicate wells are prepared for all concentrations, (concentration is often denoted by placing brackets around a number); "time-zero" and "no drug" controls are also provided for each test. The minimum amount of compound required for a one-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$ M) is: molecular weight of compound$\times$ $10^{-4}\times0.04$. After a 48 hour incubation (37° C.) with the test compound, the cells are fixed in situ to the bottoms of the microtitre wells by addition of 50 ul of either 50% trichloroacetic acid (for adherent cell lines) or 80% trichloroacetic acid (for settled cell suspension lines), followed by incubation for 60 minutes at 4° C. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening are replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50, respectively:

$GI_{50}$ is the concentration for which the PG=+50. At this value the increase from time $t_{zero}$, in the number or mass of cells in the test well is only 50% as much as the corresponding increase in the control well during this period of the experiment, see Table II. A drug effect of this intensity is interpreted as primary growth inhibition.

TGI is the concentration for which PG=0. At this value the number or mass of cells in the well at the end of the experiment equals the number or mass of cells in the well at time ter, see Table III. A drug effect of this intensity is regarded as cytostasis.

$LC_{50}$ is the concentration for which the PG=−50. At this value, the number or mass of cells in the test well at the end of the experiment is half that at time $t_{zero}$, see Table IV. This is interpreted as cytotoxicity.

TABLE II

| Panel/ Cell Line | $Log_{10} GI_{50}$ | | | | |
| --- | --- | --- | --- | --- | --- |
| | Artemisinin | C-10 Carbon-Substituted Trioxane Dimers | | | Paclitaxel |
| | | VII-f | VII-g | VII-h | |
| Leukemia | | | | | |
| HL-60(TB) | −4.26 | −6.71 | −7.20 | −7.59 | −11.57 |
| K-562 | −4.33 | −6.18 | −7.31 | −7.70 | −10.83 |
| MOLT-4 | −4.73 | −6.23 | −7.30 | <−8.00 | −11.07 |
| RPMI-8226 | >−4.00 | −6.21 | −7.25 | <8.00 | <−13.00 |
| SR | >−4.00 | −6.19 | −7.42 | <8.00 | 8.34 |
| Non-Small Cell Lung Cancer | | | | | |
| A549/ATCC | | | | | — |
| EKVX | −4.17 | −6.21 | −7.17 | −7.42 | — |
| HOP-62 | >−4.00 | −5.77 | −6.45 | −7.08 | −9.67 |
| NCI-H226 | >−4.00 | −4.61 | −4.91 | >−4.00 | — |
| NCI-H23 | >−4.00 | −5.32 | −5.92 | −6.35 | — |
| NCI-H322M | >−4.00 | −6.05 | −7.42 | −7.56 | −10.12 |
| NCI-H460 | — | −6.03 | −5.13 | −5.59 | −12.16 |
| NCI-H522 | >−4.00 | −6.07 | −6.99 | −7.22 | <−13.00 |
| | — | −5.33 | −7.09 | −7.38 | — |
| Colon Cancer | | | | | |
| COLO 205 | >−4.00 | −6.61 | −7.50 | −7.88 | −11.07 |
| HCT-116 | −4.00 | −6.12 | −7.13 | −7.53 | <−13.00 |
| HCT-15 | >−4.00 | −6.13 | −7.05 | −7.39 | −6.37 |
| HT29 | >−4.00 | −5.90 | −6.88 | −7.37 | <−13.00 |
| KM12 | >−4.00 | −6.23 | −7.27 | −7.81 | −11.43 |
| SW-620 | >−4.00 | −5.90 | −7.22 | −7.59 | −11.60 |
| HCC-2998 | — | −5.59 | −6.12 | −6.57 | — |
| CNS Cancer | | | | | |
| SF-268 | — | −5.70 | −6.42 | −6.86 | — |
| SF-295 | — | −5.25 | −6.48 | −6.39 | — |
| SNB-19 | >−4.00 | −5.85 | −6.48 | −7.09 | −8.98 |
| SNB-75 | >−4.00 | −5.84 | −6.45 | −6.99 | — |
| U251 | >−4.00 | −6.03 | −6.86 | −7.26 | −11.29 |
| Melanoma | | | | | |
| LOX IMVI | — | −5.79 | −7.07 | −7.40 | −11.80 |
| MALME-3M | — | −5.65 | −6.60 | −6.94 | — |
| SK-MEL2 | — | −5.85 | −6.39 | −6.87 | −9.53 |
| SK-MEL-28 | >−4.00 | −4.00 | — | — | — |
| UACC-257 | >−4.00 | −6.02 | −7.09 | −7.21 | −10.30 |
| UACC-62 | >−4.00 | −4.90 | −5.46 | −6.91 | −10.46 |
| SK-MEL-5 | — | −5.80 | −6.71 | −7.36 | — |
| Ovarian Cancer | | | | | |
| IGROVI | −4.31 | −4.55 | −5.16 | — | −8.61 |
| OVCAR-3 | — | −5.42 | −6.53 | −7.03 | −10.40 |
| OVCAR-4 | — | −5.93 | −6.96 | −7.51 | −5.00 |
| OVCAR-5 | >−4.00 | −6.04 | −6.58 | −7.12 | −9.38 |
| OVCAR-8 | >−4.00 | −5.57 | −6.70 | −7.33 | −10.75 |
| SK-OV-3 | — | −4.52 | −5.05 | >4.00 | — |
| Renal Cancer | | | | | |
| 786-0 | >−4.00 | −5.40 | −6.10 | −7.02 | −8.01 |
| A498 | >−4.00 | −4.79 | −6.04 | −6.29 | −7.14 |
| ACHN | >−4.00 | −5.71 | −6.37 | −6.86 | — |
| CAKI-1 | — | −5.17 | −6.22 | −6.28 | — |
| RXF 393 | −4.08 | −5.91 | −5.80 | −6.48 | −8.32 |
| SN12C | −4.21 | −5.73 | −6.69 | −7.31 | −9.53 |
| TK-10 | >−4.00 | −5.44 | −6.48 | −7.22 | −7.89 |

TABLE II-continued

| | Log$_{10}$ GI$_{50}$ | | | | |
|---|---|---|---|---|---|
| Panel/ | | C-10 Carbon-Substituted Trioxane Dimers | | | |
| Cell Line | Artemisinin | VII-f | VII-g | VII-h | Paclitaxel |
| Prostate Cancer | | | | | |
| PC-3 | −4.17 | −6.30 | −7.32 | −7.70 | −10.85 |
| DU-145 | — | −5.16 | −5.71 | −6.16 | −9.38 |
| Breast Cancer | | | | | |
| MCF7 | >−4.00 | −6.06 | −6.63 | −7.33 | −11.69 |
| NCI/ADR-RES | — | −5.29 | −5.27 | −5.76 | −8.48 |
| MDA-MB231/ATCC | −4.20 | −5.67 | −6.07 | −6.49 | −8.54 |
| HS 578T | >−4.00 | −6.13 | −7.10 | −7.31 | |
| MDA-MB-435 | — | −5.94 | −7.14 | −7.41 | <−13.00 |
| MDA-N | >−4.00 | −5.86 | −6.57 | −7.29 | <−13.00 |
| BT-549 | −4.06 | −5.74 | −6.82 | −7.33 | −9.31 |
| T-47D | — | −6.50 | −7.51 | <−8.00 | −9.81 |
| MG MID | — | −5.73 | −6.58 | −7.03 | — |
| Delta | −4.07 | 0.98 | 0.93 | 0.97 | −10.15 |
| Range | 0.73 | 2.71 | 2.60 | 4.00 | 8.00 |

TABLE III

| | Log$_{10}$ TGI | | | | |
|---|---|---|---|---|---|
| Panel/ | | C-10 Carbon-Substituted Trioxane Dimers | | | |
| Cell Line | Artemisinin | VII-f | VII-g | VII-h | Paclitaxel |
| Leukemia | | | | | |
| HL-60(TB) | −4.00 | −6.71 | −7.20 | −7.59 | −11.57 |
| K-562 | −4.00 | −6.18 | −7.31 | −7.70 | −10.83 |
| MOLT-4 | −4.00 | −6.23 | −7.30 | <−8.00 | −11.07 |
| RPMI-8226 | >−4.00 | −6.21 | −7.25 | <8.00 | <−13.00 |
| SR | >−4.00 | −6.19 | −7.42 | <8.00 | 8.34 |
| Non-Small Cell Lung Cancer | | | | | |
| A549/ATCC | | | | | |
| EKVX | >−4.00 | −4.58 | >−4.00 | >−4.00 | — |
| HOP-62 | >−4.00 | >−4.00 | >−4.00 | >−4.00 | — |
| NCI-H226 | >−4.00 | >−4.00 | >−4.00 | >−4.00 | −4.80 |
| NCI-H23 | >−4.00 | −4.36 | −4.06 | >−4.00 | — |
| NCI-H322M | >−4.00 | −4.39 | −4.87 | −5.88 | — |
| NCI-H460 | — | >−4.00 | >−4.00 | >−4.00 | −4.46 |
| NCI-H522 | >−4.00 | >−4.00 | >−4.00 | >−4.00 | −4.92 |
| | — | −5.02 | −5.59 | −6.12 | −11.20 |
| Colon Cancer | | | | | |
| COLO 205 | >−4.00 | −5.93 | −6.82 | — | — |
| HCT-116 | >−4.00 | >−4.00 | >−4.00 | −5.38 | −4.82 |
| HCT-15 | >−4.00 | −4.82 | −4.88 | >−4.00 | >−4.00 |
| HT29 | >−4.00 | >−4.00 | >−4.00 | >−4.00 | — |
| KM12 | >−4.00 | >−4.00 | >−4.00 | >−4.00 | −4.36 |
| SW 620 | >−4.00 | >−4.00 | >−4.00 | >−4.00 | >−4.00 |
| HCC 2998 | — | >−4.00 | >−4.00 | >−4.00 | — |
| CNS Cancer | | | | | |
| SF-268 | — | >−4.00 | >−4.00 | >−4.00 | — |
| SF-295 | — | >−4.00 | >−4.00 | >−4.00 | — |
| SNB-19 | >−4.00 | >−4.33 | >−4.00 | >−4.00 | >−4.00 |
| SNB-75 | >−4.00 | — | — | −5.08 | — |
| U251 | >−4.00 | >−4.00 | >−4.00 | >−4.00 | −4.32 |
| Melanoma | | | | | |
| LOX IMV1 | — | >−4.00 | −5.06 | −5.67 | −4.65 |
| MALME-3M | −4.06 | −4.82 | −4.24 | −4.17 | −4.46 |
| SK-MEL2 | >−4.00 | −4.26 | >−4.00 | −5.34 | — |
| SK MEL-28 | >−4.00 | >−4.00 | — | — | — |

TABLE III-continued

| | Log₁₀ TGI | | | | |
|---|---|---|---|---|---|
| Panel/ | | C-10 Carbon-Substituted Trioxane Dimers | | | |
| Cell Line | Artemisinin | VII-f | VII-g | VII-h | Paclitaxel |
| UACC-257 | >−4.00 | >−4.00 | −4.58 | >−4.00 | −4.52 |
| UACC-62 | >−4.00 | >−4.00 | >−4.00 | >−4.00 | −4.71 |
| SK MEL-5 | — | −4.93 | −5.16 | −6.21 | — |
| Ovarian Cancer | | | | | |
| IGROVI | >−4.00 | >−4.00 | −4.21 | −4.20 | −4.19 |
| OVCAR-3 | — | >−4.00 | >−4.00 | >−4.00 | −4.55 |
| OVCAR-4 | — | — | — | −6.31 | −4.19 |
| OVCAR-5 | >−4.00 | >−4.00 | >−4.00 | >−4.00 | −4.92 |
| OVCAR-8 | >−4.00 | −4.21 | >−4.00 | >−4.00 | — |
| SK-OV-3 | — | >−4.00 | >−4.00 | >−4.00 | |
| Renal Cancer | | | | | |
| 786-0 | >−4.00 | >−4.00 | >−4.00 | >−4.00 | >−4.00 |
| A498 | >−4.00 | −4.37 | −4.05 | >−4.00 | — |
| ACHN | >−4.00 | >−4.00 | >−4.00 | >−4.00 | −4.90 |
| CAKI-1 | — | >−4.00 | 4.29 | >−4.00 | −4.04 |
| RXF 393 | >−4.00 | >−4.00 | >−4.00 | >−4.00 | >−4.00 |
| SN12C | >−4.00 | >−4.00 | >−4.00 | >−4.00 | −4.29 |
| TK-10 | >−4.00 | >−4.00 | >−4.00 | >−4.00 | — |
| Prostate Cancer | | | | | |
| PC 3 | −4.00 | >−4.00 | >−4.00 | >−4.00 | >−4.00 |
| DU-145 | — | >−4.00 | >−4.00 | >−4.00 | >−4.00 |
| Breast Cancer | | | | | |
| MCF7 | >−4.00 | >−4.00 | >−4.00 | −4.31 | −4.05 |
| NCI/ADR-RES | — | −4.34 | >−4.00 | −4.40 | >−4.00 |
| MDA-MB231/ATCC | −4.00 | −4.70 | −4.74 | −5.35 | −4.84 |
| | >−4.00 | — | — | −5.72 | - |
| HS 578T | — | −4.31 | −4.32 | >−4.00 | — |
| MDA-MB-435 | >−4.00 | >−4.00 | >−4.00 | >−4.00 | — |
| MDA-N | −4.00 | −4.18 | −4.83 | −5.42 | −6.32 |
| BT-549 | >−4.00 | — | — | −7.10 | −4.05 |
| T-47D | | | | | |
| MG MID | — | −4.23 | −4.32 | −4.61 | — |
| Delta | −4.00 | 1.70 | 2.51 | 2.62 | −4.54 |
| Range | 0.06 | 1.93 | 2.82 | 3.23 | 7.20 |

TABLE IV

| | Log₁₀ LC₅₀ | | | | |
|---|---|---|---|---|---|
| Panel/ | | C-10 Carbon-Substituted Trioxane Dimers | | | |
| Cell Line | Artemisinin | VII-f | VII-g | VII-h | Paclitaxel |
| Leukemia | | | | | |
| HL-60(TB) | >−4.00 | >−4.00 | >−4.00 | >−4.00 | >−4.53 |
| K-562 | >−4.00 | >−4.00 | >−4.00 | >−4.00 | >−4.00 |
| MOLT-4 | >−4.00 | >−4.00 | >−4.00 | >−4.00 | >−4.00 |
| RPMI-8226 | >−4.00 | >−4.00 | >−4.00 | >−4.00 | >−4.00 |
| SR | >−4.00 | >−4.00 | >−4.00 | >−4.00 | >−4.00 |
| Non-Small Cell Lung Cancer | | | | | |
| A549/ATCC | | | | | |
| EKVX | >−4.00 | >−4.00 | >−4.00 | >−4.00 | — |
| HOP-62 | >−4.00 | >−4.00 | >−4.00 | >−4.00 | — |
| NCI-H226 | >−4.00 | >−4.00 | >−4.00 | >−4.00 | −4.10 |
| NCI-H23 | >−4.00 | >−4.00 | >−4.00 | >−4.00 | — |
| NCI-H322M | >−4.00 | >−4.00 | >−4.00 | >−4.00 | — |
| NCI-H460 | — | — | — | — | >−4.00 |
| NCI-H522 | >−4.00 | >−4.00 | >−4.00 | >−4.00 | >−4.00 |
| | — | — | — | — | >−4.00 |
| Colon Cancer | | | | | |
| COLO 205 | >−4.00 | −5.30 | −4.96 | — | >−4.41 |
| HCT-116 | >−4.00 | >−4.00 | >−4.00 | >−4.00 | >−4.00 |

TABLE IV-continued

| | Log$_{10}$ LC$_{50}$ | | | | |
|---|---|---|---|---|---|
| Panel/ | | C-10 Carbon-Substituted Trioxane Dimers | | | |
| Cell Line | Artemisinin | VII-f | VII-g | VII-h | Paclitaxel |
| HCT-15 | >−4.00 | >−4.00 | >−4.00 | >−4.00 | >−4.00 |
| HT29 | >−4.00 | >−4.00 | >−4.00 | >−4.00 | −4.39 |
| KM12 | >−4.00 | >−4.00 | >−4.00 | >−4.00 | >−4.00 |
| SW-620 | >−4.00 | >−4.00 | >−4.00 | >−4.00 | >−4.00 |
| HCC-2998 | — | >−4.00 | >−4.00 | >−4.00 | |
| CNS Cancer | | | | | |
| SF-268 | — | >−4.00 | >−4.00 | >−4.00 | — |
| SF-295 | — | >−4.00 | >−4.00 | >−4.00 | — |
| SNB-19 | >−4.00 | >−4.33 | >−4.00 | >−4.00 | >−4.00 |
| SNB-75 | >−4.00 | >−4.00 | >−4.00 | >−4.00 | — |
| U251 | >−4.00 | >−4.00 | >−4.00 | >−4.00 | −4.15 |
| Melanoma | | | | | |
| LOX IMVI | — | >−4.00 | >−4.00 | −4.15 | −4.15 |
| MALME-3M | >−4.00 | >−4.00 | >−4.00 | >−4.00 | −4.11 |
| SK-MEL2 | >−4.00 | >−4.00 | >−4.00 | >−4.00 | >−4.00 |
| SK-MEL-28 | >−4.00 | >−4.00 | — | — | — |
| UACC-257 | >−4.00 | >−4.00 | >−4.00 | >−4.00 | −4.03 |
| UACC-62 | >−4.00 | >−4.00 | >−4.00 | >−4.00 | −4.19 |
| SK MEL-5 | — | >−4.00 | >−4.00 | — | — |
| Ovarian Cancer | | | | | |
| IGROVI | >−4.00 | >−4.00 | >−4.00 | >−4.00 | >−4.00 |
| OVCAR-3 | — | >−4.00 | >−4.00 | >−4.00 | >−4.00 |
| OVCAR-4 | — | >−4.00 | >−4.00 | >−4.00 | >−4.00 |
| OVCAR-5 | >−4.00 | >−4.00 | >−4.00 | >−4.00 | >−4.00 |
| OVCAR-8 | >−4.00 | >−4.00 | >−4.00 | >−4.00 | >−4.00 |
| SK-OV-3 | — | >−4.00 | >−4.00 | >−4.00 | — |
| Renal Cancer | | | | | |
| 786-0 | >−4.00 | >−4.00 | >−4.00 | >−4.00 | >−4.00 |
| A498 | >−4.00 | >−4.00 | >−4.00 | >−4.00 | −4.13 |
| ACHN | >−4.00 | >−4.00 | >−4.00 | >−4.00 | −4.45 |
| CAKI-1 | — | >−4.00 | >−4.00 | >−4.00 | >−4.00 |
| RXF 393 | >−4.00 | >−4.00 | >−4.00 | >−4.00 | >−4.00 |
| SN12C | >−4.00 | >−4.00 | >−4.00 | >−4.00 | >−4.00 |
| TK-10 | >−4.00 | >−4.00 | >−4.00 | >−4.00 | — |
| Prostate Cancer | | | | | |
| PC-3 | >−4.00 | >−4.00 | >−4.00 | >−4.00 | >−4.00 |
| DU-145 | — | >−4.00 | >−4.00 | >−4.00 | >−4.00 |
| Breast Cancer | | | | | |
| MCF7 | >−4.00 | >−4.00 | >−4.00 | >−4.00 | >−4.00 |
| NCI/ADR-RES | — | >−4.00 | >−4.00 | >−4.00 | >−4.00 |
| MDA-MB231/ATCC | >−4.00 | >−4.00 | >−4.00 | >−4.00 | −4.29 |
| HS 578T | >−4.00 | >−4.00 | >−4.00 | >−4.00 | — |
| | — | >−4.00 | >−4.00 | >−4.00 | — |
| MDA-MB-435 | >−4.00 | >−4.00 | >−4.00 | >−4.00 | — |
| MDA-N | >−4.00 | >−4.00 | >−4.00 | >−4.00 | >−4.00 |
| BT-549 | >−4.00 | >−4.00 | >−4.00 | >−4.00 | >−4.00 |
| T-47D | | | | | |
| MG MID | — | −4.23 | −4.02 | −4.01 | — |
| Delta | −4.00 | 1.70 | 0.94 | 0.43 | — |
| Range | 0.00 | 1.93 | 0.96 | .44 | 4.06 .045 |

The C-10 carbon-substituted trioxane dimers VII-f, VII-g and VII-h of the present invention in most instances are as potent and in some instances more potent than paclitaxel. The data in Tables II, III and IV are graphically represented in FIGS. 6a, b, c, d, and e through FIGS. 14d. Dose response curves, shown in the above mentioned Figures, are obtained by exposing various cancer cell lines to compounds having a known concentration ($[\log_{10}M]$), as discussed in detail above, and then plotting the percentage growth of each cell line for each concentration. The drug concentration limits that are tested are between $10^{-4}$ or −4.00M and $10^{-9}$ or −9.00M. The −4.00M value being the high concentration and the −9.00 M value being the low concentration. Percentage growth is determined by dividing the number or mass of cells in the test well by the number or mass of cells in a control well. Referring to the leukemia cell line MOLT-4 in FIGS. 6a, 6b, 6c, 6d, and 6e the first comparison that is made between artemisinin, paclitaxel, and the C-10 carbon-substituted trioxane dimers VII-f, VII-g and VII-h the present invention are the drug concentrations which are necessary to inhibit growth, graphically represented in FIGS. 6a, 6b, 6c, 6d, and 6e as the concentration necessary to achieve the percentage growth value of +50. As discussed previously, the five drug dilutions routinely tested range from $10^{-4}$ to $10^{-9}$ molar. Therefore, concentrations less than or greater than $10^{-9}$ and $10^{-4}$ molar, respectively, that are required to achieve a desired result are not determined. Referring now to FIG. 6a, some concentration of paclitaxel that is less than $10^{-8}$M is necessary to achieve primary growth inhibition; in fact the lower concentrations have been determined for this drug and the concentration at which primary growth inhibition occurs using paclitaxel is at $10^{-11}$ molar. FIG. 6b indicates that some concentration of artemisinin that is greater than $10^{-4}$ molar is necessary to achieve primary growth inhibition. Referring to the C-10 carbon-substituted trioxane dimers VII-f, VII-g, and VII-h dose response curves in FIGS. 6c, 6d and 6e, respectively, the leukemia cell line MOLT-4 displays primary growth inhibition at drug concentrations that are greater than $10^{-6}$, $10^{-7}$ and greater than $10^{-8}$, respectively. The drug concentration at which artemisinin is considered cytostatic, i.e., percentage growth is equal to 0, is at a concentration greater than $10^{-4}$ molar. The C-10 carbon-substituted trioxane dimers VII-f, VII-g and VII-h reach cytostasis at drug concentrations of approximately $10^{-4}$ M, and at some concentration greater than $10^{-4}$ M, respectively, while the paclitaxel concentration necessary to achieve cytostasis is some value greater than $10^{-4}$ M. Cytotoxicity, i.e., the concentration for which the percentage growth is equal to −50, occurs at a concentration greater than $10^{-4}$ M for paclitaxel, artemisinin, and for both C-10 carbon-substituted trioxane dimers VII-f, VII-g and VII-h.

The potency of the C-10 carbon-substituted trioxane dimer VII-f, VII-g and VII-h present invention as compared to artemisinin and paclitaxel varies from cell line to cell line. The mean values for each drug are presented at the end Tables II, III and IV and the C-10 carbon-substituted trioxane dimer VII-f, VII-g and VII-h of the present invention are more potent than artemisinin and equivalent to and in many instances higher in potency than paclitaxel.

The dihydroartemisinin condensation by-product disclosed by M. Cao et al., and tested by D. L. Klayman and H. J. Woerdenbag, discussed previously, was approximately twenty-two times more potent at causing 50% growth inhibition in one cancer cell line than artemisinin. With respect to the drug concentrations causing 50% growth inhibition, the dimers VII-f, VII-g and VII-h were at least 100 times more potent than artemisinin. When interpreting the mean values, it is important to take into consideration that drug concentrations less than $10^{-9}$M and greater then 10M were not collected, and this factor is reflected in the range.

For a further comparison on the effects of the trioxane dimers of the present invention on various cancer cell lines versus the effects of artemisinin and paclitaxel on the same cell lines see FIGS. 7a, b, c, d and e for non-small cell lung cancer cell lines, FIGS. 8a, b, c, d and e for colon cancer cell lines, FIGS. 9a, b, c, d and e for CNS cancer cell lines, FIGS. 10a, b, c, d and e for melanoma cancer cell lines, FIGS. 11a, b, c, d and e for ovarian cancer cell lines, FIGS. 12a, b, c, d and e for renal cancer cell lines, FIGS. 13a, b, c and d for prostate cancer cell lines and FIGS. 14a, b, c and d for breast cancer cell lines.

In summary, the peroxide bond in artemisinin itself and in artemisinin-derived trioxane aldehyde Ie has been shown for the first time to withstand exposure to powerful organometallic nucleophiles like heteroaryllithium and aryllithium reagents, n-butyllithium, a phenyl Grignard reagent, and phosphonium ylides. Several of these nucleophiles added with high chemoselectivity to the lactone carbonyl group of artemisinin and to the aldehyde and ketone carbonyl groups of artemisinin-derived aldehyde Ie and ketone I-4. In this way, a series of new, enantiomerically pure, C-10 carbon-substituted derivatives of natural artemisinin was prepared. Antimalarial testing in vitro of these semi-synthetic, C-10 non-acetal analogs of artemisinin showed them to have high antimalarial activities.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

The invention is further illustrated by the following non-limited examples. All scientific and technical terms have the meanings as understood by one with ordinary skill in the art. The specific examples which follow illustrate the synthesis of representative compounds of the instant invention and are not to be construed as limiting the invention in sphere or scope. The methods may be adapted to variation in order to produce compounds embraced by this invention but not specifically disclosed. Further, variations of the methods to produce the same compounds in somewhat different fashion will be evident to one skilled in the art. The synthetic descriptions and specific examples that follow are only intended for the purposes of illustration, and are not to be construed as limiting in any manner to make compounds of the present invention by other methods.

EXAMPLES

Unless otherwise noted, reactions were run in oven-dried glassware under an atmosphere of argon. Diethyl ether (ether) and tetrahydrofuran (THF) were distilled from sodium benzophenone ketyl prior to use. Methylene chloride ($CH_2Cl_2$) was distilled from calcium hydride prior to use. All other compounds were purchased from Aldrich Chemical Company and used without further purification. Analytical thin-layer chromatography (TLC) was conducted with Silica Gel 60 F254 plates (250 min thickness, Merck). Column chromatography was performed using flash silica gel (partical size 400–230 mesh). Yields are not optimized. Purity of final products was judged to be >95% based on their chromatographic homogeneity. High performance liquid chromatography (HPLC) was carried out with a Rainin HPLX system equipped with two 25 mL/min preparative pump heads using a Rainin Dynamax 10 mm×250 mm (semi-preparative) column packed with 60 Å silica gel (8 μm pore size) as bare silica. Melting points were measured using a Mel-Temp metal-block apparatus and are uncorrected. Nuclear magnetic resonance (NMR) spectra were obtained either on a Varian XL-400 spectrometer, operating at 400 MHZ for $^1H$ and 100 MHZ for $^{13}C$. Chemical shifts are reported in parts per million (ppm, δ) downfield from tetramethylsilane. Splitting patterns are described as singlet (s), doublet(d), triplet(t), quartet(q), multiplet(m) and broad (br). Infrared (IR) spectra were obtained using a Perkin-Elmer 1600 FT-IR spectrometer. Resonances are reported in wavenumbers ($cm^{-1}$). Low and high resolution mass spectra (LRMS and HRMS) were obtained with electronic or chemical ionization (EI or CI) either (1) at Johns Hopkins University on a VG Instruments 70-S Spectrometer run at 70 eV for EI and run with ammonia ($NH_3$), butane ($C_4H_{10}$) or methane ($CH_4$) as carrier gas for CI or (2) at the University of Illinois at Champaign-Urbana on a Finnigan-MAT CH5, a Finnigan-MAT 731, or a VG Instruments 70-VSE spectrometer run at 70 eV for EI and run with methane ($CH_4$) for CI. Combustion analyses were conducted by Atlantic Microlab (Norcross, Ga.). Various methods of purifyng the products of the present invention are known and understood by those skilled in the art and the purification methods presented in the Examples is solely listed by way of example and is not intended to limit the invention.

Example I

Preparation of 10-Formylanhydroartemisienin of the Present Invention a) Synthesis of 10-Acetyl-10-(2'-thiazolyl)artemisinin (1a)

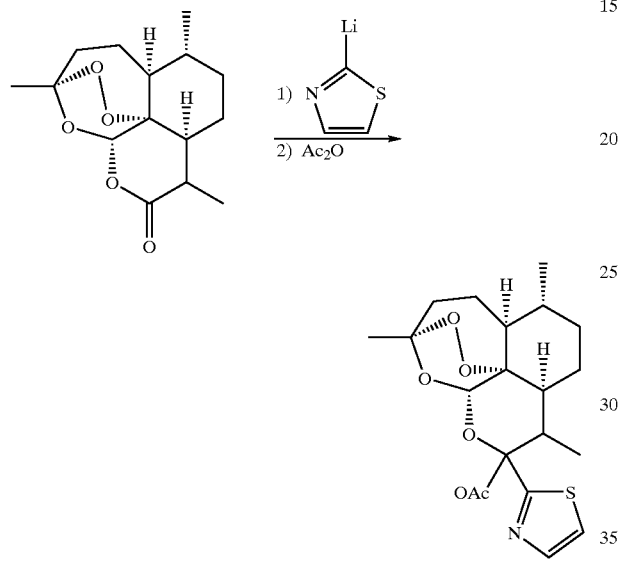

2-Bromothiazole (90 μL, 1.0 mmol) in Et$_2$O (1 mL) at −78° C. was treated with n-BuLi (1.6 M in hexanes, 0.70 mL, 1.1 mmol). The reaction mixture was stirred for 30 minutes at −78° C. and then artemisinin (I, 0.20 g, 0.71 mmol, in 1 mL THF) was added via cannula. The reaction mixture was stirred for 30 minutes at −78° C. and then for 30 minutes at −65° C. At −65° C., acetic anhydride (0.67 mL, 7.1 mmol) was added, after being stirred for 10 minutes at −65° C. the reaction mixture became viscous. The reaction mixture was warmed to room temperature, diluted (CH$_2$Cl$_2$) then poured into pH 7 phosphate buffer (100 mL) and extracted ( CH$_2$Cl$_2$). The organic layer was dried (Na$_2$SO$_4$) and concentrated. The crude product was chromatographed on a flash silica gel column with 50% EtOAc/hexanes as eluent to give 0.28 g of the desired product 1a as a white solid (0.68 mmol, 95%); mp 128° C. (dec.); [α]$_D^{23}$ +232° (c 0.55, EtOAc); $^1$H NMR (CDCl$_3$) α 0.94–1.08 (m, 1H), 0.98 (d, J=6.4 Hz, 3 H), 1.11 (d, J=7.2 Hz, 3H), 1.3–1.7 (m, 4H), 1.49 (s, 3H), 1.7–1.8 (m, 2H), 1.9–2.1 (m, 3H), 2.10 (s, 3H), 2.35–2.45 (m, 1H), 2.60–2.68 (m, 1H), 5.54 (s, 1H), 7.3 (d, J=3.2 Hz, 1H), 7.7 (d, J=3.2 Hz, 1H); $^{13}$C NMR (CDCl$_3$) α 11.6, 20.0, 21.7, 23.4, 24.5, 25.6, 34.3, 35.91, 35.96, 37.3, 45.5, 51.7, 79.7, 89.1, 101.4, 104.4, 119.9, 141.5, 167.2, 170.2; HRMS calcd for C$_{20}$H$_{27}$NO$_6$S: 409.1559, found: 409.1554. The product was further purified prior to antimalarial testing using HPLC (Silica semipreparative column, 25% EtOAc/hexanes at 3 mL/min, R$_t$ 12 min); characteristic data were identical to those given above.

b) Synthesis of 10-(2'-Thiazolyl)anhydroartemisinin (1b)

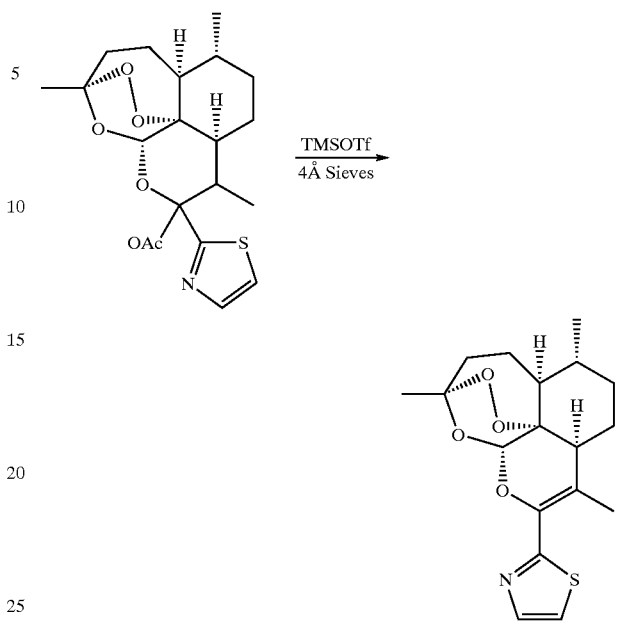

Acetate 1a (0.11 g, 0.27 mmol) and powdered 4 MS (185 mg) in CH$_2$Cl$_2$ (2.5 mL) at room temperature were treated with triethylsilane (0.43 mL, 2.7 mmol) followed by trimethylsilyl triflate (0.14 mL, 0.76 mmol). The reaction mixture was stirred at room temperature for 30 minute then quenched with triethylamine (2 mL), filtered through celite and concentrated. The crude product was chromatographed on a flash silica gel column with 15% EtOAc/hexanes as eluent to give 82 mg of the desired product Ib as a white solid (0.23 mmol, 87%); mp 164–167° C.; [α]$_D^{23}$ +42° (c 0.56, EtOAc); $^1$HNMR (CDCl$_3$) δ 1.0 (d, J=5.6 Hz, 3H), 1.1–1.2 (m, 1H), 1.25–1.40 (m, 1H), 1.40–1.64 (m, 3H), 1.45 (s, 3H), 1.65–1.75 (m, 1H), 1.9–2.0 (m, 2H), 2.00–2.15 (m, 2H), 2.25 (s, 3H), 2.38–2.43 (m, 1H), 5.77 (s, 1H), 7.3 (d, J=3.2 Hz, 1H), 7.7 (d, J=3.2 Hz, 1H); $^{13}$CNMR (CDCl$_3$) δ 17.1, 20.1, 24.4, 25.6, 29.0, 34.1, 36.0, 37.5, 47.9, 50.6, 78.3, 90.2, 104.5, 110.6, 118.3, 138.0, 142.7, 165.0; HRMS calcd for C$_{18}$H$_{23}$NO$_4$S:349.1348, found: 349.1354. The product was further purified prior to antimalarial testing using HPLC (Silica semipreparative column, 5% EtOAc/hexanes at 3 mL/min, R$_t$ 13 minute); characteristic data were identical to those given above.

c.) Synthesis of 10-Formylanhydroartemisinin (Ie)

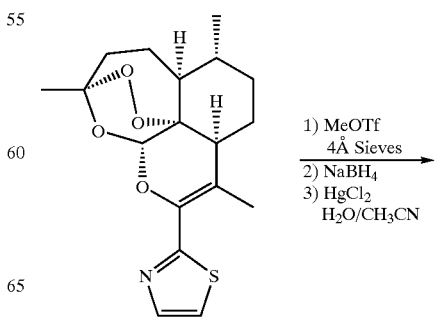

-continued

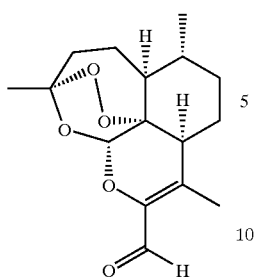

Reaction was performed under an atmosphere of air. Thiazole Ib (128 mg, 0.37 mmol) and powdered 4 Å MS (0.75 g) in acetonitrile (4 mL) at room temperature were treated with methyl triflate (80 μL, 0.71 mmol), the suspension was stirred for 15 min and then concentrated to dryness. The crude N-methylthiazolium salt was suspended in methanol (4 mL), cooled to 0° C. and then treated with sodium borohydride (60 mg, 1.6 mmol). The reaction mixture was warmed to room temperature and stirred for 15 min, then quenched at 0° C. with acetone (8 mL). The crude reaction mixture was filtered through celite and then concentrated. The reduced product was then dissolved in acetonitrile (4 mL) and treated with $HgCl_2$ (140 mg) followed by $H_2O$ (0.4 mL), the mixture was stirred for 15 min at room temperature then filtered through celite and concentrated. The crude product was dissolved (THF, $CH_2Cl_2Et_2O$) and washed with (20% aq. KI soln. (twice), $H_2O$, brine). The organic layer was dried ($Na_2SO_4$) and concentrated. The crude product was chromatographed on a Florisil (~200 mesh) column with 25% EtOAc/hexanes as eluent to give 90 mg of the desired aldehyde Ie as white solid (0.31 mmol, 87%); mp 115–117° C.; $[\alpha]_D^{23}$ +1020° (c 0.33, EtOAc); $^1$H NMR ($CDCl_3$) δ 1.0 (d, J=6.0 Hz, 3H), 1.10–1.32 (m, 2H), 1.38–1.64 (m, 3H), 1.43 (s, 3H), 1.7–1.8 (m, 1H), 1.88–1.98 (m, 2H), 2.0–2.1 (m, 2H), 2.10 (s, 3H), 2.34–2.44 (m, 1H), 5.7 (s, 1H), 9.8 (s, 1H); $^{13}$C NMR ($CDCl_3$) δ14.8, 20.0, 24.2, 25.6, 28.7, 34.0, 36.0, 37.4, 47.8, 50.5, 78.0, 90.0, 104.7, 126.7, 142.8, 184.2; HRMS calcd for $C_{16}H_{22}O_5$:294.1467, found: 294.1474. The product was further purified prior to antimalarial testing using HPLC (Silica semipreparative column, 30% EtOAc/hexanes at 3 mL/min, $R_t$ 9 min); characteristic data were identical to those given above.

Example II

Preparation of the Exocyclic Alkenes of the Present Invention

10-Acetyl-10-(21-benzothiazolyl)artemisinin (Benzo-3)-Benzothiazole (76 μL, 0.70 mmol) in THF (1 mL) at –78° C. was treated with n-BuLi (1.6 M in hexanes, 0.44 mL, 1.1 equiv.). The reaction mixture was stirred for 30 min at –78° C., then artemisinin (I, 0.14 g, 0.50 mmol, in 1.5 mL THF) was added via canula. The reaction mixture was stirred for 30 min at –78° C. and then for 30 min at –65° C. At –65° C., acetic anhydride (0.50 mL, 10 equiv.) was added, after being stirred for 10 min at –65° C. the reaction mixture became viscous. The reaction mixture was warmed to room temperature, diluted ($CH_2Cl_2$) then poured into pH 7 phosphate buffer (100 mL) and extracted ($CH_2Cl_2$). The organic layer was dried ($Na_2SO_4$) and concentrated. The crude product was chromatographed on a flash silica gel column with 20–40% EtOAc/hexanes as eluent to give 0.21 g of the desired product Benzo-3 as a white solid (0.45 mmol, 91%); mp 129–131° C.; $[\alpha]_D^{23}$ +183° (c 0.46, EtOAc); $^1$HNMR ($CDCl_3$) δ 0.94–1.08 (m, 1H), 0.99 (d, J=6.0 Hz, 3H), 1.18 (d, J=7.2 Hz, 3H), 1.28–1.84 (m, 6H), 1.55 (s, 3H), 1.90–2.14 (in, 3H), 2.15 (s, 3H), 2.38–2.48 (m, 1H), 2.70–2.80 (m, 1H), 5.57 (s, 1H), 7.35 (m, 1H), 7.43 (m, 1H), 7.88 (m, 1H), 7.99 (m, 1H); $^{13}$C NMR ($CDCl_3$) δ 11.7, 20.1, 21.8, 23.6, 24.7, 25.8, 34.5, 35.3, 36.1, 37.5, 45.6, 51.8, 79.9, 89.3, 101.4, 104.7, 121.6, 123.3, 124.9, 125.5, 135.8, 152.7, 167.4, 171.0

Example III 10-(2'-Benzothiazolyl)anhydroartemisinin (Benzo-4)-Acetate Benzo-3 (0.10 g, 0.22 mmol) and powdered 4 MS (160 mg) in $CH_2Cl_2$ (3 mL) at room temperature were treated with triethylsilyl triflate (0.14 mL, 0.62 mmol). The mixture was stirred at room temperature for 1 h then quenched with triethylamine (2 mL), filtered through celite and concentrated. The crude product was chromatographed on a flash silica gel column with 10% EtOAc/hexanes as eluent to give 65 mg of the desired product Benzo-4 as a white solid (0.16 mmol, 74%); mp 155–158° C.; $[\alpha]_D^{23}$ +36° (c 0.46, EtOAc); $^1$H NMR ($CDCl_3$) δ 0–99 (d, J=6.0 Hz, 3H), 1.1–1.2 (m, 1H), 1.25–1.40 (m, 1H), 1.40–1.64 (m, 3H), 1.47 (s, 3H), 1.68–1.75 (m, 1H), 1.9–2.0 (m, 2H), 2.00–2.14 (m, 2H), 2.35 (s, 3H), 2.36–2.46 (m, 1H), 5.80 (s, 1H), 7.34 (m, 1H), 7.44 (m, 1H), 7.88 (m, 1H), 8.01 (in, 1H); $^{13}$C NMR ($CDCl_3$) δ 17.4, 20.1, 24.4, 25.6, 28.9, 34.1, 36.0, 37.5, 48.1, 50.5, 78.3, 90.4, 104.6, 113.7, 121.3, 123.0, 124.7, 125.6, 134.5, 138.1, 153.7, 165.0; HRMS calcd for $C_{22}H_{25}NO_4S$: 399.1504, found: 399.1501. The product was further purified prior to antimalarial testing using HPLC (Silica semipreparative column, 10% EtOAc/hexanes at 3 mL/min, $R_t$ 10 min); characteristic data were identical to those given above.

Example IV 10-(1'-Pentanoyl)anhydroartemisinin (I-3) -Aldehyde Ie (80 mg, 0.27 mmol) in THF (2 mL) at –78° C. was treated with n-BuLi (1.6 M in hexanes, 0.20 mL, 1.2 equiv.). The reaction mixture was stirred for 2 h at –78° C. then warmed to room temperature, diluted ($Et_2O$), washed (aq. $NH_4Cl$, aq. $NaHCO_3$, brine), dried ($Na_2SO_4$) and concentrated. The crude product was chromatographed on a flash silica gel column with 10% EtOAc/petroleum ether as eluent to give 73 mg of the desired products I-1 as an oil (0.21 mmol, 77%), a ca. 1:1.5 mixture of diastereomers (as determined by $^1$H NMR). The mixture of alcohols (73 mg, 0.21 mmol), powdered 4 Å MS (150 mg) and NMO (50 mg, 0.43 mmol) in $CH_2Cl_2$ (1.5 mL) at room temperature was treated with TPAP (catalytic amount, ca. 5 mg). The reaction mixture was stirred for 2 h, then filtered through celite and concentrated. The crude product was chromatographed on a flash silica gel column with 10% EtOAc/petroleum ether as eluent to give 56 mg of the desired product I-3 as an oil (0.16 mmol, 76%); $[\alpha]D^{23}$ +149° (c 0.43, EtOAc); $^1$H NMR ($CDCl_3$) δ 0–91 (t, J=7.6 Hz, 3H), 0.99 (d, J=6.0 Hz, 3H), 1.06–1.28 (m, 3H), 1.30 1.40 (m, 2H), 1.43 (s, 3H), 1.46–1.64 (m, 5H), 1.82 (dd, J=4.4, 12.4 Hz, 1H), 1.90–2.10 (m, 3H), 2.00 (s, 3H), 2.36–2.45 (m, 1H), 2.63 (dt, J=7.6, 16.4 Hz, 1H), 2.77 (dt, J=7.6, 16.4 Hz, 1H), 5.66 (s, 1H); $^{13}$C NMR (CDC'3)δ 14.0, 17.2, 20.1, 22.5, 24.4, 25.6, 25.8, 28.9, 34.1, 36.1, 37.6, 39.8, 48.4, 50.4, 78.0, 90.0, 104.5, 117.3, 142.5, 199.8; HRMS calcd for $C_{20}H_{30}O_5$: 350.2093, found: 350.2096. The product was further purified prior to antimalarial testing using HPLC (Silica semipreparative column, 10% EtOAc/hexanes at 3 mL/min, $R_t$ 9 min); characteristic data were identical to those given above.

Example V

10-Benzoylanhydroartemisinin (I-4)-Aldehyde Ie (68 mg, 0.23 mmol) in THF (2 mL) at −78° C. was treated with PhMgBr (1.0 M in THF, 0.30 mL, 1.3 equiv.). The reaction mixture was stirred for 2 h at −78° C., warmed to room temperature, diluted (Et$_2$O), washed (aq. NH$_4$Cl, aq. NaHCO$_3$, brine), dried (Na$_2$SO$_4$) and concentrated. The crude product was chromatographed on a flash silica gel column with 10% EtOAc/petroleum ether as eluent to give 75 mg of the desired products I-2 as an oil (0.20 mmol, 87%), a ca. 1:7.5 mixture of diastereomers. The mixture of alcohols (75 mg, 0.20 mmol), powdered 4 Å MS (150 mg) and NMO (50 mg, 0.43 mmol) in CH$_2$Cl$_2$ (1.5 n-mL) at room temperature was treated with TPAP (catalytic amount, ca. 5 mg). The reaction mixture was stirred for 2 h, then filtered through celite and concentrated. The crude product was chromatographed on a flash silica gel column with 10% EtOAc/petroleum ether as eluent to give 72 mg of the desired product I-4 as an white solid (0.19 mmol, 97%); mp ~155° C. (dec.); $[\alpha]_D^{23}$ +244° (c 0.42, EtOAc); $^1$H NMR (CDCl$_3$) δ 1.00 (d, J=6.4 Hz, 3H), 1.10–1.22 (m, 1H), 1.24–1.38 (dq, J=3.2, 12.8 Hz, 1H), 1.38–1.64 (m, 3H), 1.46 (s, 3H), 1.68–1.78 (m, 1H), 1.86 (s, 3H), 1.88–2.00 (m, 2H), 2.04–2.16 (m, 2H), 2.40–2.50 (m, 1H), 5.66 (s, 1H), 7.38–7.44 (m, 2H), 7.48–7.56 (m, 1H), 8.16–8.22 (m, 2H); $^{13}$C NMR (CDCl$_3$) δ 16.5, 20.1, 24.3, 25.5, 29.3, 34.0, 36.1, 37.4, 47.3, 50.8, 78.3, 90.1, 104.6, 114.6, 127.8, 130.4, 132.8, 136.6, 142.5, 191.4; HRMS calcd for C$_{22}$H$_{26}$O$_5$: 370.1780, found: 370.1788. The product was farther purified prior to antimalarial testing using HPLC (Silica semi-preparative column, 10% EtOAc/hexanes at 3 mL, R$_t$ 11 min); characteristic data were identical to those given above.

Example VI 10-(Benzhydryl)anhydroartemisinin (I-5)-Ketone I-4 (60 mg, 0.16 mmol) in THF (2 mL) at −78° C. was treated with PhLi (1.8 M in cyclohexane-ether, 70 to 30, 0.14 mL, 1.5 equiv.). The reaction mixture was stirred at −78° C. for 2 h, then slowly warmed to room temperature (1 h), diluted (Et$_2$O), washed (brine, aq. NH$_4$Cl, aq. NaHCO$_3$, brine), dried (Na$_2$SO$_4$) and concentrated. The crude product was chromatographed on a flash silica gel column with 10% EtOAc/petroleum ether as eluent to give 63 mg of the desired product I-5 as an oil (0.15 mmol, 91%); mp 152–155° C. (dec.); $[\alpha]_D^{23}$ +146° (c 0.5 1, EtOAc); $^1$H NMR (CDCl$_3$) δ 0.97 (d, J=6.0 Hz, 3H), 1.03 (s, 3H), 1.04–1.14 (m, 1H), 1.22–1.56 (m, 4H), 1.33 (s, 3H), 1.64–1.72 (m, 2H), 1.90–2.06 (m, 3H), 2.34–2.44 (m, 1H), 4.20 (br s, 1H), 5.65 (s, 1H), 7.20–7.49 (m, 10H); $^{13}$C NMR (CDCl$_3$) δ 16.8, 20.1, 24.4, 25.5, 28.4, 34.1, 36.1, 37.6, 48.0, 50.4, 78.4, 80.1, 90.3, 104.4, 106.6, 127.17, 127.25, 127.59, 127.81, 127.86, 128.5, 144.9, 145.1, 146.0; HRMS calcd for C$_{28}$H$_{32}$O$_5$: 448.2250, found: 448.2259. The product was further purified prior to antimalarial testing using HPLC (Silica semipreparative column, 10% EtOAc/hexanes at 3 mL/min, R$_t$ 13 min); characteristic data were identical to those given above.

Example VII

10-Vinylanhydroartemisinin (VII-a)- Methyltriphenylphosphonium bromide (0.71 g, 2.0 mmol) was dried under vacuum/low heat for 2 days. The Wittig salt was suspended in THF (4 mL) and at 0° C. treated with n-BuLi (1.6 M in hexanes, 1.4 mL, 2.4 mmol). The solution was stirred at room temperature for 1 h. Aldehyde Ie (0.15 g, 0.50 mmol) in THF (3 mL) at −78° C. was treated with a portion of the prepared ylide solution (ca. 0.33 M, 2 mL, ca. 0.70 mmol) transferred via syringe. The mixture was stirred at −78° C. for 1 h then warmed to room temperature and stirred for 15 min; a precipitate was observed. The reaction was quenched (H$_2$O), extracted (Et$_2$O), washed (brine), dried (Na$_2$SO$_4$) and concentrated. The crude product was chromatographed on a flash silica gel column with 5–10% EtOAc/hexanes as eluent to give 112 mg of the desired product VII-a as an oil (0.38 mmol, 77%); $[\alpha]_D^{23}$ +81° (c 0.49, EtOAc); $^1$H NMR (CDCl$_3$) δ 0.98 (d, J=6.0 Hz, 3H), 1.04–1.30 (m, 2H), 1.42 (s, 3H), 1.44–1.80 (m, 5H), 1.76 (s, 3H), 1.88–2.08 (m, 3H), 2.34–2.44 (m, 1), 5.10 (dd, J=2.0, 10.8 Hz, 1H), 5.62 (dd, J=2.0, 10.8 Hz, 1H), 5.66 (s, 1H), 6.50 (dd, J=10. 8, 16.8 Hz, 1H); $^{13}$C NMR (CDCl$_3$) δ 15.7, 20.2, 24.5, 29.3, 34.2, 36.2, 37.6, 46.7, 51.0, 78.7, 90.0, 104.3, 107.5, 113.2, 127.7, 141.7; HRMS calcd for C$_{17}$H$_{24}$O$_4$: 292.1675, found: 292.1678. The product was further purified prior to antimalarial testing using HPLC (Silica semipreparative column, 5% EtOAc/hexanes at 3 mL/min, R$_t$ 9 min); characteristic data were identical to those given above.

Example VIII 10-(1-Propenyl)anhydroartemisinin (VII-b)- Ethyltriphenylphosphonium bromide (0.74 g, 2.0 mmol) was dried under vacuum/low heat for 2 days. The Wittig salt was suspended in THF (4 mL) and at 0° C. treated with n-BuLi (1.6 M in hexanes, 1.4 mL, 2.4 mmol). The solution was stirred at room temperature for 2 h. Aldehyde Ie (0.20 g, 0.67 mmol) in THF (3 mL) at −78° C. was treated with a portion of the prepared ylide solution (ca. 0.33 M, 5 mL, ca. 1.7 mmol) transferred via syringe. The reaction mixture was stirred at −78° C. for 30 min then warmed to room temperature and stirred for 1 h; a precipitate was observed. The reaction was quenched (H$_2$O), extracted (Et$_2$O), washed (brine), dried (Na2SO$_4$) and concentrated. The crude product was chromatographed on a flash silica gel column with 5% EtOAc/hexanes as eluent to give 170 mg of the desired product Z-VII-b as an oil (0.55 mmol, 83%); $[\alpha]_D^{23}$ +52° (c 0.50, EtOAc); $^1$H NMR (CDCl$_3$) δ 0.98 (d, J=6.0 Hz, 3H), 1.02–1.28 (m, 3H), 1.42 (s, 3H), 1.50–1.78 (m, 4H), 1.73 (s, 3H), 1.80 (d, J=6.0 Hz, 3H), 1.88–2.08 (m, 3H), 2.34–2.44 (m, 1), 5.64 (s, 1H), 6.07–6.22 (m, 2H); $^{13}$C NMR (CDCl$_3$) δ 15.6, 18.2, 20.2, 24.5, 25.8, 29.4, 34.2, 36.2, 3 7.6, 46.6, 51.0, 78.8, 89.9, 104.3, 104.7, 122.3, 125.3, 141.4; HRMS calcd for C$_{18}$H$_{26}$O$_4$: 306.183 1, found: 306.1833. The product was further purified prior to antimalarial testing using HPLC (Silica semipreparative column, 2% EtOAc/hexanes at 3 mL/min, R$_t$ 15 min); characteristic data were identical to those given above.

Example IX 10-(StyryI)anhydroartemisinin Z/E-(VII-c)- Benzyltriphenylphosphonium bromide (0.43 g, 1.0 mmol) was dried under vacuum/low heat for 3 h. The Wittig salt was suspended in THF (4 mL) and at 0° C. treated with n-BuLi (1.6 M in hexanes, 0.75 mL, 1.2 mmol). The solution was stirred at room temperature for 1 h. Aldehyde Ie (21 mg, 71 μmol) in THF (1.5 mL) at −78° C. was treated with a portion of the prepared ylide solution (ca. 0.16 M, 0.6 mL, ca. 1.5 equiv.) transferred via syringe. The reaction mixture was stiffed at −78° C. for 30 min then warmed to room temperature and stirred for 30 min. The reaction was quenched (H$_2$O), extracted (Et$_2$O), washed (brine), dried (Na$_2$SO$_4$) and concentrated. The crude product was chromatographed on a flash silica gel column with 10% EtOAc/ hexanes as eluent to give 20 mg of the desired products Z/E-VII-c as an oil (54 μmol, 76%), Z:E=1.2:1 (as determined by $^1$H NMR). The two isomers were separated by HPLC (Silica semipreparative column, 1% EtOAc/hexanes at 5 mL/min), Z $R_t$ 20 min, E $R_t$ 22 min. ZVII-c: oil, $[\alpha]_D^{23}$ +42° (c 0.48, EtOAc); $^1$H NMR (CDCl$_3$) δ 0.98 (d, J=6.0 Hz, 3H), 1.02–1.28 (m, 2H), 1.416 (s, 3H), 1.422 (s, 3H), 1.40–1.74 (m, 5H), 1.88–2.08 (mn, 3H), 2.36–2.46 (m, 1), 5.64 (s, 1H), 6.03 (d, J=12.0 Hz, 1H), 6.50 (d, J=12.0 Hz, 1H), 7.15–7.22 (m, 1H), 7.23–7.30 (m, 2H), 7.53 (d, J=7.2 Hz, 2H); $^{13}$C NMR (CDCl$_3$) 8 16.4, 20.3, 24.5, 25.8, 29.3, 34.1, 36.4, 37.6, 45.9, 51.2, 78.8, 90.0, 104.4, 105.6, 122.5, 127.1, 127.8, 129.2, 132.3, 137.2, 141.4; HRMS calcd for C$_{23}$H$_{28}$O$_4$: 368.1988, found: 368.,1986. E-VII-e: oil, $[\alpha]_D^{23}$+150° (c 0.51, EtOAc); $^1$H NMR (CDCl$_3$) δ 1.00 (d, J=6.0 Hz, 3H), 1.02–1.28 (m, 2H), 1.45 (s, 3H), 1.40–1.74 (m, 4H), 1.86 (s, 3H), 1.80–2.10 (m, 4H), 2.36–2.46 (m, 1), 5.72 (s, 1H), 6.87 (d, J=16.0 Hz, 1H), 6.99 (d, J=16.0 Hz, 1H), 7.17–7.24 (m, 1H), 7.27–7.34 (m, 2H), 7.43–7.50 (m, 2H); $^{13}$C NMR (CDCl$_3$) δ 16.1, 20.2, 24.5, 25.8, 29.4, 34.2, 36.2, 37.6, 47.0, 51.0, 78.7, 90.1, 104.4, 108.5, 119.6, 126.6, 127.2, 127.6, 128.4, 137.7, 142.0; HRMS calcd for C$_{23}$H$_{28}$O$_4$:368.1988, found: 368.1983.

Example X 10-(p-Nitrostyryl)anhydroartemisinin Z/E-(VII-d)-(p-Nitrobenzyl) triphenylphosphonium bromide (0.96 g, 2.0 mmol) was dried under vacuum overnight. The Wittig salt was suspended in THF (4 mL) and at 0° C. treated with (1.6 M BuLi in hexanes, 1.4 mL, 2.2 mmol). The solution was stiffed at room temperature for 30 min. Aldehyde Ie (83 mg, 0.28 mmol) in THF (2 mL) at −78° C. was treated with a portion of the prepared ylide solution (ca. 0.33 M, 1.4 mL, ca. 1.5 equiv.) transferred via syringe. The reaction mixture was stiffed at room temperature for 90 min. The reaction was quenched (H$_2$O), extracted (Et$_2$O), washed (brine), dried (Na$_2$SO$_4$) and concentrated. The crude product was chromatographed on a flash silica gel column with 5–15% EtOAc/hexanes as eluent to give 80 mg of the desired products Z/E-VII-d as a yellow oil (0.19 mmol, 69%), Z.-E=1:4 (as determined by $^1$H NMR). The two isomers were separated by HPLC (Silica semipreparative column, 5% EtOAc/hexanes at 3 mL/min), Z $R_t$ 18 min, E $R_t$ 21 min. ZVII-d: yellow oil, $[\alpha]_D^{23}$ +105° (c 0.40, EtOAc); $^1$H NMR (CDCl$_3$) δ 0.98 (d, J=6.0 Hz, 3H), 1.06–1.32 (m, 2H), 1.39 (s, 3H), 1.40–1.76 (m, 4H), 1.50 (s, 3H), 1.84–2.10 (m, 4H), 2.36–2.46 (m, 1), 5.61 (s, 1H), 6.25 (d, J=12.0 Hz, 1H), 6.51 (d, J=12.0 Hz, 2H), 7.69 (d, J=8.8 Hz, 2H), 8.13 (d, J=8.8 Hz, 2H); $^{13}$C NMR (CDCl$_3$) δ 16.4, 20.2, 24.4, 25.8, 29.4, 34.0, 36.3, 37.6, 46.0, 51.2, 78.8, 90.1, 104.5, 108.2, 123.0, 125.7, 129.3, 13 0.1, 141.0, 144.1; HRMS calcd for C$_{23}$H$_{27}$NO$_6$: 413.1838, found: 413.1841. E-VII-d: yellow oil, $[\alpha]_D^{23}$ +53° (c 0.5 1, EtOAc); $^1$H NMR (CDC$_3$) δ 1.00 (d, J=6.0 Hz, 3H), 1.06–1.32 (m, 2H), 1.46 (s, 3H), 1.40–1.74 (m, 4H), 1.90 (s, 3H), 1.84–2.10 (m, 4H), 2.36–2.4 (m, 1), 5.73 (s, 1H), 7.02 (s, 2H), 7.55 (d, J=8.8 Hz, 2H), 8.17 (d, J=8.8 Hz, 2H); $^{13}$C NMR (CDCl$_3$) δ 16.2, 20.1, 24.4,25.8, 29.2, 34.0, 36.1, 37.5, 47.0, 50.8, 78.6, 90.1, 104.5, 112.2, 123.7, 123.9, 125.3, 126.8, 141.7, 144.4, 146.4; HRMS calcd for C$_{23}$H$_{27}$NO$_6$: 413.1838, found: 413.1845.

Example XI 10-(p-Chlorostyryl)anhydroartemisinin Z/E-(VII-e)-(p-Chlorobenzyl) triphenylphosphonium bromide (0.85 g, 2.0 mmol) was dried under vacuum overnight. The Wittig salt was suspended in THF (4 mL) and at 0° C. treated with n-BuLi (1.6 M in hexanes, 1.4 mL, 2.2 mmol). The solution was stirred at room temperature for 30 min. Aldehyde Ie (97 mg, 0.33 nmmol) in TBF (2 mL) at −78° C. was treated with a portion of the prepared ylide solution (ca. 0.33 M, 2.1 mL, ca. 0.69 mmol) transferred via syringe. The reaction mixture was stirred at −78° C. for 30 min, warmed to room temperature and stirred for 10 min. The reaction was quenched (H$_2$O), extracted (Et$_2$O), washed (brine), dried (Na$_2$SO$_4$) and concentrated. The crude product was chromatographed on a flash silica gel column with 5% EtOAc/hexanes as eluent to give 78 mg of the desired products ZIE-VII-e as an oil (0.19 mmol, 58%), Z:E=2.2:1 (as determined by $^1$H NMR). Upon storage at −15° C. in ca. 0.2 M solution of EtOAc:hexanes, 1:10, a 1:1 complex of Z:E crystallized out. The mother liquor was concentrated to give 30 mg of ZVII-e as an oil; $[\alpha]_D^{23}$ +119° (c 0.52, EtOAc); $^1$H NMR (CDCl$_3$) δ 0.98 (d, J=6.0 Hz, 3H), 1.02–1.28 (m, 2H), 1.41 (s, 3H), 1.44 (s, 3H), 1.40–1.74 (m, 5H), 1.88–2.08 (m, 3H), 2.36–2.46 (m, 1), 5.63 (s, 1H), 6.04 (d, J=12.0 Hz, 1H), 6.43 (d, J=12.0 Hz, 1H), 7.23 (d, J=8.4 Hz, 2H), 7.49 (d, J=8.4 Hz, 2H); $^{13}$C NMR (CDCl$_3$) δ 16.3, 20.3, 24.4, 25.8, 29.4, 34.1, 36.3, 37.6, 45.9, 51.2, 78.8, 90.0, 104.4, 106.2, 123.0, 127.9, 130.6, 13 0.8, 132.7, 13 5.6, 14 1.1. The remaining mixture of E/Z (1:1) resisted attempts at chromatographic separation by HPLC.

Example XII

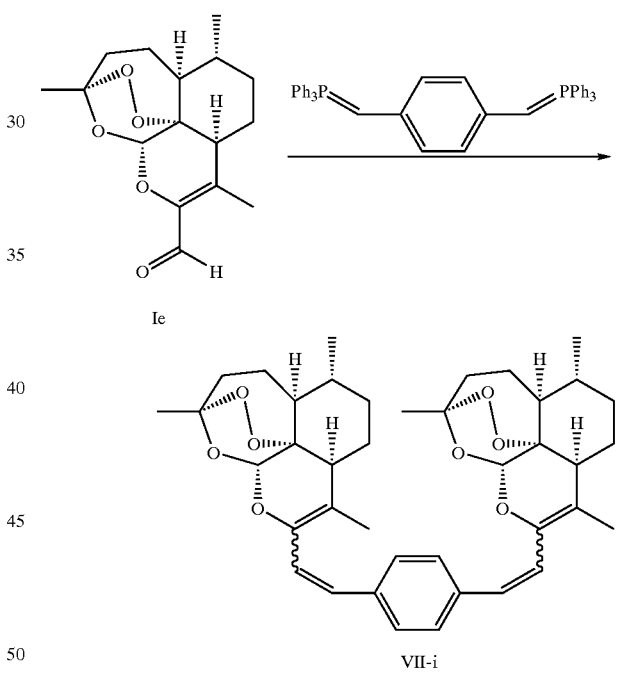

p-Xylylenebis(triphenylphosphonium bromide) (0.79 g, 1.0 mmol) was dried under vacuum/low heat for 3 h. The Wittig salt was suspended in THF (2 mL) and at 0° C. treated with n-BuLi (1.6 M in hexanes, 1.4 mL, 2.2 mmol). The solution was stirred at room temperature for 1 h to give a black solution. Aldehyde Ie (50 mg, 0. 17 mmol) in THF (1.0 mL) at −78° C. was treated with a portion of the prepared bis-ylide solution (ca. 0.25 M, 0.34 mL, ca. 0.085 mmol) transferred via syringe. The reaction mixture was stirred at −78° C. for 30 min then warmed to room temperature and stirred for 30 min. The reaction was quenched (H$_2$O), extracted (Et$_2$O), washed (brine), dried (Na$_2$SO$_4$) and concentrated. The crude product was chromatographed on a flash silica gel column with 8–15% EtOAc/hexanes as eluent to give 35 mg of the desired product VII-i as a mixture of all 3 possible Z/E isomers as an oil (53 gmol, 63%), EE:EZ:ZZ=3:2:1 (as determined by ¹H NMR). The three isomers were separated by HPLC: Silica semipreparative column, 10% EtOAc/hexanes at 3 mL/min, gave ZZ/EZ (mixture); $R_t$, 13 min, EE $R_t$, 15 min. Silica semipreparative column, 100% $CH_2Cl_2$ at 3 mL/min, gave separation of the ZZ/EZ: mixture; EZ$R_t$, 8 min, ZZ$R_t$, 13 min.; VII-i [EE] $[\alpha]_D^{23}$ +31° (c 0.47, EtOAc); ¹H NMR $CDCl_3$ δ0.98 (d, J=6.0 Hz, 6H), 1.02–1.28 (m, 6H), 1.45 (s, 6H), 1.45–1.72 (m, 6H), 1.86 (s, 6H), 1.80–2.08 (m, 8H), 2.36–2.46 (m, 2), 5.71 (s, 2H), 6.86 (d, J=15.6 Hz, 2H), 6.97 (d, J=15.6 Hz, 2H), 7.39 (s, 4H); ¹³C NMR $(CDCl_3)$ δ 16.1, 20.2, N.5, 25.8, 29.3, 34.1, 36.2, 37.6, 46.9, 50.9, 78.7, 90.1, 104.8, 108.5, 119.1, 126.7, 127.3, 136.7, 142.0; HRMS calcd for $C_{40}H_{50}O_8$: 658.3506, found: 658.3515; VII-i [EZ] $[\alpha]_D^{23}$ +144° (c 0.48, EtOAc); ¹H NMR $(CDCl_3)$ δ 0.98 (d, J=5.6 Hz, 3H), 0.99 (d, J=5.6 Hz, 3H), 1.02–1.28 (m, 6H), 1.42 (s, 6H), 1.45 (s, 3H), 1.45–1.76 (m, 6H), 1.86 (s, 3H), 1.80–2.08 (m, 8H), 2.35–2.48 (m, 2), 5.66 (s, 1H), 5.70 (s, 1H), 6.00 (d, J=12.0 Hz, 1H), 6.46 (d, J=12.0 Hz, 1H), 6.85 (d, J=16.0 Hz, 1H), 6.95 (d, J 16.0 Hz, 1H), 7.35 (d, J=8.0 Hz, 1H), 7.49 (d, J=8.0 Hz, 1H); ¹³C NMR $(CDCl_3)$ δ 16.1, 16.5, 20.2, 20.3, 24.5, 25.8, 29.3, 29.4, 34.10, 34.15, 36.2, 36.4, 37.6, 45.9, 47.0, 51.0, 51.2, 78.7, 78.8, 90.0, 90.1, 104.37, 104.40, 105.6, 108.4, 119.2, 122.2, 126.1, 127.5, 129.5, 132.0, 136.2, 136.5, 141.4,142.1; HRMS calcd for $C_{40}H_{50}O_8$: 658.3506, found: 658.3501; VII-i[ZZ] ¹H NMR $(CDCl_3)$ δ 0.98 (d, J=6.0 Hz, 6H), 1.02–1.28 (m, 6H), 1.39 (s, 6H), 1.42 (s, 6H), 1.38–1.72 (m, 8H), 1.86–2.08 (m, 6H), 2.36–2.46 (m, 2), 5.66 (s, 2H), 6.00 (d, J 12.0 Hz, 2H), 6.46 (d, J=12.0 Hz, 2H), 7.43 (s, 4H).

ZE:EE:ZZ=6:3:2 (as determined by ¹H NMR). The three isomers were separated by HPLC: Silica semipreparative column, 10% EtOAc/hexanes at 3 mL/min, gave ZZ $R_t$, 11 min, EE/EZ (mixture); $R_t$, 13 min. Silica semipreparative column, 80% $CH_2Cl_2$/hexanes at 3 mL/min, gave separation of the EE/EZ: mixture; EE $R_t$, 9 min, EZ $R_t$, 19 min.; VII-f [EE] $[\alpha]_D^{23}$ 0° (c 0.48, EtOAc); ¹H NMR $(CDCl_3)$ δ 0–99 (d, J=5.6 Hz, 6H), 1.02–1.32 (m, 6H), 1.46 (s, 6H), 1.40–1.72 (m, 8H), 1.87 (s, 6H), 1.80–2.08 (m, 6H), 2.36–2.46 (m, 2), 5.72 (s, 2H), 6.87 (d, J=15.6 Hz, 2H), 6.99 (d, J=15.6 Hz, 2H), 7.22 (m, 3H), 7.53 (s, br, 1H); ¹³C NMR $(CDCl_3)$ δ16.1, 20.2, 24.5, 25.8, 29.4, 34.2, 36.2, 37.6, 47.0, 51.0, 78.7, 90.1, 104.4, 108.5, 119.6, 125.1, 125.4, 127.6, 128.5, 137.9, 142.0; HRMS calcd for $C_{40}H_{50}O_4$: 658.3506, found: 658.3515; VII-g [EZ] $[\alpha]_D^{23}$+77° (c 0.49, EtOAc); ¹H NMR $(CDCl_3)$ δ 0.97 (d, J=6.0 Hz, 3H), 0.99 (d, J=5.6 Hz, 3H), 1.02–1.30 (m, 6H), 1.40 (s, 3H), 1.41 (s, 3H), 1.44 (s, 3H), 1.38–1.74 (m, 8H), 1.86 (s, 3H), 1.80–2.08 (m, 8H), 2.35–2.46 (m, 2), 5.65 (s, 1H), 5.70 (s, 1H), 6.05 (d, J=12.0 Hz, 1H), 6.50 (d, J=12.0 Hz, 1H), 6.85 (d, J=15.6 Hz, 1H), 6.96 (d, J=15.6 Hz, 1H), 7.19–7.24 (t, J=7.6 Hz, 1H), 7.27–7.31 (m, 1H), 7.42–7.45 (m, 1H), 7.49 (s, br, 1H), ¹³C NMR $(CDCl_3)$ δ 16.1, 16.5, 20.2, 20.5, 24.5, 25.8, 29.2, 29.4, 34.1, 34.2, 36.2, 36.3, 37.6, 45.9, 46.9, 51.0, 51.1, 78.695, 78.704, 89.9, 90.0, 104.3, 104.4, 105.5, 108.2, 119.3, 122.8, 125.4, 127.2, 127.8, 128.0, 128.2, 132.3, 137.2, 137.5, 141.3, 142.0; HRMS calcd for $C_{40}H_{50}O_4$: 658.3506, found: 658.3508; VII-h [ZZ][a]$_D^{23}$ +228° (c 0.49, EtOAc); ¹H NMR $(CDCl_3)$ δ 0.98 (d, J=5.6 Hz, 6H), 1.02–1.28 (m, 4H), 1.36 (s, 6H), 1.41 (s, 6H), 1.38–1.70 (m, 10H), 1.88–1.96 (m, 4H), 2.00–2.08 (m, 2H), 2.36–2.46 (m, 2), 5.66 (s, 2H), 5.99 (d, J=12.0 Hz, 2H), 6.48 (d, J=12.0 Hz, 2H), 7.15–7.20 (t, J=8.0 Hz, 1H), 7.39 (d, J=7.6 Hz, 1H), 7.43 (d, J=7.6 Hz, 1H), 7.50 (s, br, 1H); ¹³C NMR $(CDCl_3)$ δ 16.5, 20.3, 24.5, 25.9, 29.2, 34.1, 36.4, 37.6, 45.9, 51.2, 78.7, 89.9, 104.4, 105.0, 122.5, 127.6, 128.0, 129.8, 132.7, 136.8, 141.4; HRMS calcd for $C_{40}H_{50}O_8$: 658.3506, found: 658.3515.

Example XIII

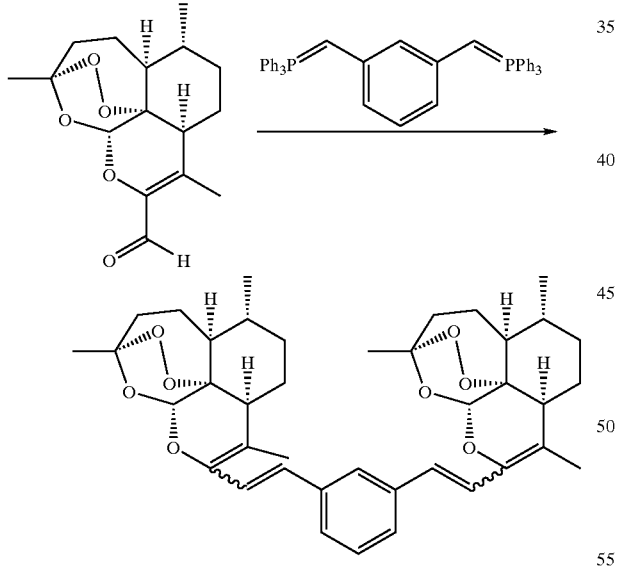

m-Xylylenebis(triphenylphosphonium bromide (0.13 g, 0.17 mmol), aldehyde Ie (0.10 g, 0.34 mmol) in EtOH (1.0 mL) at 0° C. was treated with lithium bis(trimethylsilyl)amide (1.0 M in THF, 0.68 niL, 4.0 equiv.). The reaction was stirred for 10 min at 0° C, then for 10 min at room temperature. The reaction was concentrated then diluted in ether, washed (brine), dried $(Na_2SO_4)$ and concentrated. The crude product was chromatographed on a flash silica gel column with 10% EtOAc/hexanes as eluent to give 111 mg of the desired product (VII-f,-g, and -h) as a mixture of all 3 possible Z/E isomers as an oil (0.17 mmol, 99%), Example XIV

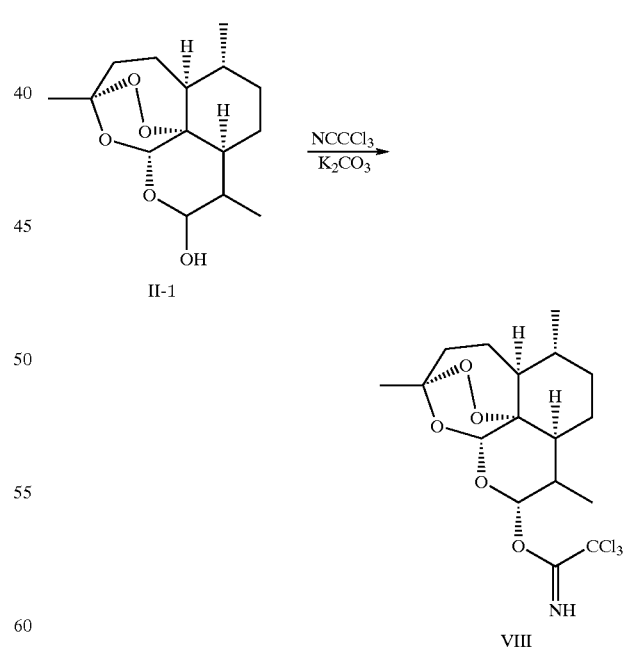

Dihydroartemisinin (II-1, 0.30 g, 1.1 mmol), potassium carbonate (600 mg, 4.4 mmol) in $CH_2Cl_2$ (6.0 mL) at room temperature were treated with trichloroacetonitrile (0.51 mL, 5.1 mmol). The reaction was stirred for 6 h, then filtered and concentrated to give the crude product VIII as a foamy solid (0.48 g, ca. 100%). The crude material was unstable to chromatography (silica gel/Florisil) and resisted attempts at recrystallization. NMR confirmed desired product VIII was formed in sufficient purity for further use; $^{1}$H NMR (CDCl$_3$) δ 0.97 (d, J=7.2 Hz, 3H), 0.98 (d, J=6.0 Hz, 3H), 1.0–2.0 (in, 8H), 1.43 (s, 3H), 2.0–2.2 (in, 2H), 2.3.–2.5 (in, 1), 2.6–2.8 (in, 1), 5.50 (s, 1H), 5.85 (d, J=9.6 Hz, 1H), 8.56 (s, br, 1H); $^{13}$C NMR (CDCl$_3$) δ 12.0, 20.1, 21.9, 24.5, 25.8, 32.1, 34.0, 36.1, 37.1, 45.2, 51.5, 79.9, 91.4, 96.3, 104.3, 161.5.

Example XV

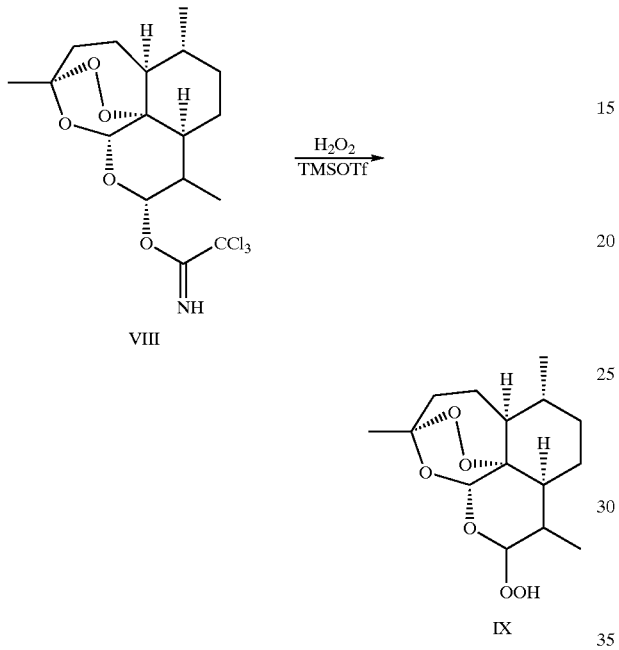

Imidate VIII (0.30 g, 0.70 mmol) in CH$_2$Cl$_2$ (10 mL) at −78° was treated with H$_2$O$_2$ (ca. 18 M in acetonitrile, 2.0 mL, 5 equiv.), followed by TMSOTf (100 μL, catalytic amount). The reaction was stirred for 20 min at −78° C., then for 10 min at room temperature. The reaction was diluted in ether, washed (sat. aq. NaHCO, brine), dried (Na$_2$SO$_4$) and concentrated. The crude product was chromatographed on a flash silica gel column with 25% EtOAc/petroleum ether as eluent to give 153 mg of the desired product IX as a solid (0.51 mmol, 73%); $^{1}$H NMR (CDCl$_3$) δ 0.97 (d, J=6.0 Hz, 3H), 0.99 (d, J=7.2 Hz, 3H), 1.18–1.56 (m, 6H), 1.46 (s, 3H), 1.60–1.80 (m, 2H), 1.88–1.98 (m, 1), 2.01–2.09 (m, 1), 2.35–2.45 (m, 1), 2.76–2.86 (m, 1), 5.33 (d, J=4.4 Hz, 1H), 5.62 (s, 1H), 9.77 (s, br, 1H); $^{1}$H NMR also shows broad singlets at δ 6.1 (1H) and 6.6 (1H) which slowly disappear under vacuum-product appears to be isolated as a monohydrate; $^{13}$C NMR (CDCl$_3$) δ 12.7, 20.2, 24.7, 24.8, 25.9, 30.9, 34.3, 36.2, 37.4, 43.8, 52.2, 80.7, 88.1, 104.5, 106.3.

Example XVI

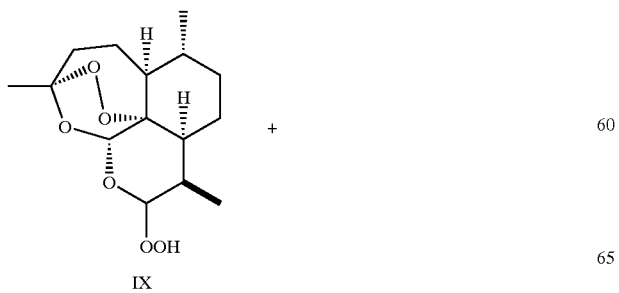

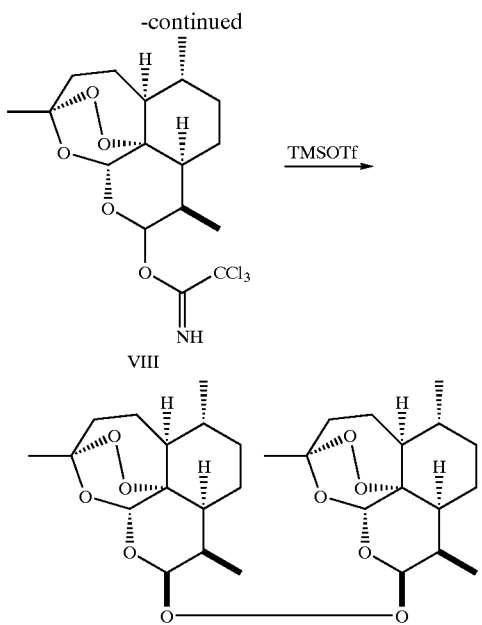

Imidate VIII (32 mg, 75 μmol), hydroperoxide IX (31 mg, 0.10 mmol, 1.3 equiv.) in CH$_2$Cl$_2$ (1.0 mL) at −78° C. was treated with TMSOTf (14 μL, 75 μymol, 1.0 equiv.). The reaction was stirred for 30 min at −78° C., then diluted in ether, washed (sat. aq. NaHCO$_3$, brine), dried (Na$_2$SO$_4$) and concentrated. The crude product was chromatographed on a flash silica gel column with 10% EtOAc/petroleum ether as eluent to give 22 mg of the desired product X as a solid (39 μmol, 52%); $^{1}$H NMR (CDCl$_3$) δ 0.94 (d, J=6.4 Hz, 6H), 0.95 (d, J=7.6 Hz, 6H), 1.18–1.28 (m, 2H), 1.36–1.74 (m, 14H), 1.43 (s, 6H), 1.82–1.92 (m, 2H), 2.00–2.08 (m, 2) 2.32–2.42(m,2),2.74–2.84(m,2),5.32(d, J=4.4 Hz, 2H)5.67 (s, 2H); $^{13}$CNMR (CDCl$_3$) δ 13.0, 20.2, 24.7, 24.9, 26.0, 31.2, 34.4, 36.4, 37.1, 44.0, 52.4, 81.0, 88.0, 103.76, 103.86.

The embodiments of the invention in which an exclusive property or privilege is claimed are defined as follows:

1. An artemisinin compound having the formula

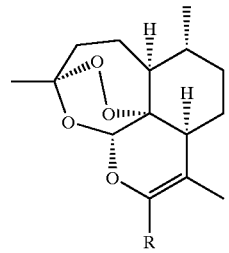

wherein R is
C(=)OX wherein X is hydrogen, alkyl, alkenyl, alkynyl, aryl or heteroaryl,
C(OH)X$_2$ wherein X is alkyl, alkenyl, alkynyl, aryl or heteroaryl,
alkyl,
alkyl comprising one or more substituents,
heteroalkyl,
alkenyl,
alkenyl comprising one or more substituents, alkynyl,
aryl,
aryl comprising one or more substituents,
heteroaryl, or
heteroaryl comprising one or more substituents,
wherein said substituents are selected from the group comprising halogen, nitro, amino, hydroxy, thiohydroxy, lower alkoxy, lower thioalkyl, lower alkyl, NHC(=O)R$_1$ wherein R$_1$ is aryl or lower alkyl, COOH, or COOR$_2$ wherein R$_2$ is aryl or lower alkyl.

2. The artemisinin compound according to claim 1 wherein R is 2'-thiazolyl.

3. The artemisinin compound according to claim 1 wherein R is 2'-benzothiazolyl.

4. The artemisinin compound according to claim 1 wherein R is CHO.

5. The artemisinin compound according to claim 1 wherein R is C(O)n-Bu.

6. The artemisinin compound according to claim 1 wherein R is C(O)Ph.

7. The artemisinin compound according to claim 1 wherein R is C(OH)Ph2.

8. The artemisinin compound according to claim 1 wherein R is CH=CH2.

9. The artemisinin compound according to claim 1 wherein R is CH=CHPh.

10. The artemisinin compound according to claim 9 wherein the compound is the [E,E] isomer.

11. The artemisinin compound according to claim 9 wherein the compound is the [Z,Z] isomer.

12. The artemisinin compound according to claim 1 wherein R is CH=CHPh-p-NO2.

13. The artemisinin compound according to claim 12 wherein the compound is the [E,E] isomer.

14. The artemisinin compound according to claim 12 wherein the compound is the [Z,Z] isomer.

15. A method of producing a novel artemisinin analogue comprising:
reacting artemisinin with an organolithium reagent that chemoselectively reacts at the C-10 position of artemisinin without disrupting the O—O bond to form a lithiated oxide at the C-10 position followed by adding a reagent that acetylates the C-10 oxide in situ to afford the intermediate (Ia) having the structure (Ia)

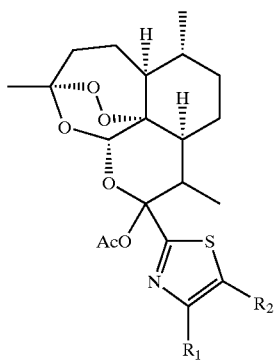

wherein R$_1$ and R$_2$ are hydrogen or together R$_1$ and R$_2$ form a benzene ring;
treating said intermediate (Ia) with a reagent which eliminates HOAc from (Ia) to form the 9,10 alkene (Ib) having the structure (Ib)

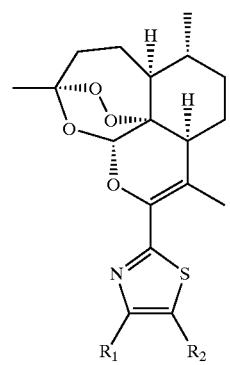

wherein R$_1$ and R$_2$ are hydrogen or together R$_1$ and R$_2$ form a benzene ring; and
converting said 9, 10 alkene (Ib) to enal (Ie) having the structure (Ie)

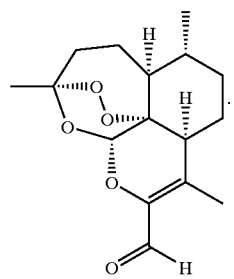

16. A method for treating malaria comprising administering an effective amount of an artemisinin analog having the structure

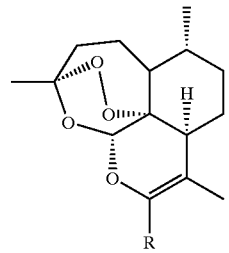

wherein R is
(C=)OX wherein X is hydrogen, alkyl, alkenyl, alkynyl, aryl or heteroaryl,
C(OH)X$_2$ wherein X is alkyl, alkenyl, alkynyl, aryl or heteroaryl,
alkyl,
alkyl comprising one or more substituents,
heteroalkyl,
alkenyl,
alkenyl comprising one or more substituents,
alkynyl,
aryl,
aryl comprising one or more substituents,
heteroaryl, or
heteroaryl comprising one or more substituents,
wherein said substituents are selected from a group comprising halogen, nitro, amino, hydroxy, thiohydroxy, lower alkoxy, lower thioalkyl, lower alkyl, NHC(=O)R$_1$ is aryl or lower alkyl, COOH, or COOR$_2$ wherein R$_2$ is aryl or lower alkyl.

* * * * *